United States Patent [19]
Devita et al.

[11] Patent Number: 5,438,136
[45] Date of Patent: Aug. 1, 1995

[54] BENZO-FUSED MACROCYCLES PROMOTE RELEASE OF GROWTH HORMONE

[75] Inventors: Robert J. Devita, Westfield; William R. Schoen, Edison; Alison J. Frontier, Rahway; Matthew J. Wyvratt, Jr., Mountainside, all of N.J.

[73] Assignee: Merck & Co., Inc., Rahway, N.J.

[21] Appl. No.: 146,245

[22] Filed: Nov. 2, 1993

[51] Int. Cl.$^6$ ............ A61K 31/395; C07D 513/06; C07D 498/06; C07D 487/06
[52] U.S. Cl. ........................................ 540/456
[58] Field of Search ............................... 540/456

[56] References Cited

U.S. PATENT DOCUMENTS

| | | | |
|---|---|---|---|
| 3,239,345 | 3/1966 | Hodge et al. | 99/2 |
| 4,036,979 | 7/1977 | Asato | 424/275 |
| 4,411,890 | 10/1983 | Momany | 424/177 |

FOREIGN PATENT DOCUMENTS

| | | | |
|---|---|---|---|
| 253310 | 7/1987 | European Pat. Off. | 548/253 |
| 291969 | 5/1988 | European Pat. Off. | 548/250 |
| 324377 | 1/1989 | European Pat. Off. | 548/254 |

OTHER PUBLICATIONS

Jones, et al J. Chem. Soc. pp. 2176–2181 (1969).
Davis, et al. Arch. Biochem. Biophys 102, pp. 48–51 (1963).
Wattley, et al J. Med. Chem. 28. pp. 1511–1516 (1985).
Slade, et al. J. Med. Chem 28, pp. 1517–1521 (1985).
Ott. Arch. Pharm. (Weinheim. Gen) 325 (9) pp. 601–603 (1990).
Huang, et al. Synthesis 10 p. 851 (1984).
Stewart, Autralia J. Chem. 33 pp. 633–640 (1980).
Still, et al J. Org. Chem. 43 p. 2923 (1978).

*Primary Examiner*—Robert T. Bond
*Attorney, Agent, or Firm*—J. Eric Thies; David L. Rose

[57] ABSTRACT

There are disclosed certain novel compounds identified as benzo-fused macrocycles which promote the release of growth hormone in humans and animals. This property can be utilized to promote the growth of food animals to render the production of edible meat products more efficient, and in humans, to increase the stature of those afflicted with a lack of a normal secretion of natural growth hormone. Growth promoting compositions containing such benzo-fused macrocycles as the active ingredient thereof are also disclosed.

6 Claims, No Drawings

BENZO-FUSED MACROCYCLES PROMOTE RELEASE OF GROWTH HORMONE

BACKGROUND OF THE INVENTION

Growth hormone, which is secreted from the pituitary, stimulates growth of all tissues of the body that are capable of growing. In addition, growth hormone is known to have the following basic effects on the metabolic process of the body:

1. Increased rate of protein synthesis in all cells of the body;
2. Decreased rate of carbohydrate utilization in cells of the body;
3. Increased mobilization of free fatty acids and use of fatty acids for energy.

A deficiency in growth hormone secretion can result in various medical disorders, such as dwarfism.

Various ways are known to release growth hormone. For example, chemicals such as arginine, L-3,4-dihydroxyphenylalanine (L-DOPA), glucagon, vasopressin, and insulin induced hypoglycemia, as well as activities such as sleep and exercise, indirectly cause growth hormone to be released from the pituitary by acting in some fashion on the hypothalamus perhaps either to decrease somatostatin secretion or to increase the secretion of the known secretagogue growth hormone releasing factor (GRF) or an unknown endogenous growth hormones releasing hormone or all of these.

In cases where increased levels of growth hormone were desired, the problem was generally solved by providing exogenous growth hormone or by administering an agent which stimulated growth hormone production and/or release. In either case the peptidyl nature of the compound necessitated that it be administered by injection. Initially the source of growth hormone was the extraction of the pituitary glands of cadavers. This resulted in a very expensive product and carried with it the risk that a disease associated with the source of the pituitary gland could be transmitted to the recipient of the growth hormone. Recently, recombinant growth hormone has become available which, while no longer carrying any risk of disease transmission, is still a very expensive product which must be given by injection or by a nasal spray.

Other compounds have been developed which stimulate the release of endogenous growth hormone such as analogous peptidyl compounds related to GRF or the peptides of U.S. Pat. No. 4,411,890. These peptides, while considerably smaller than growth hormones are still susceptible to various proteases. As with most peptides, their potential for oral bioavailability is low. The instant compounds are non-peptidyl agents for promoting the release of growth hormone which may be administered parenterally, nasally or by the oral route.

SUMMARY OF THE INVENTION

The instant invention covers certain benzo-fused macrocyclic compounds which have the ability to stimulate the release of natural or endogenous growth hormone. The compounds thus have the ability to be used to treat conditions which require the stimulation of growth hormone production or secretion such as in humans with a deficiency of natural growth hormone or in animals used for food production where the stimulation of growth hormone will result in a larger, more productive animal. Thus, it is an object of the instant invention to describe the benzo-fused macrocyclic compounds. It is a further object of this invention to describe procedures for the preparation of such compounds. A still further object is to describe the use of such compounds to increase the secretion of growth hormone in humans and animals. A still further object of this invention is to describe compositions containing the benzo-fused macrocyclic compounds for the use of treating humans and animals so as to increase the level of growth hormone secretions. Further objects will become apparent from a reading of the following description.

DESCRIPTION OF THE INVENTION

The novel benzo-fused macrocycles of the instant invention are best described in the following structural formula I:

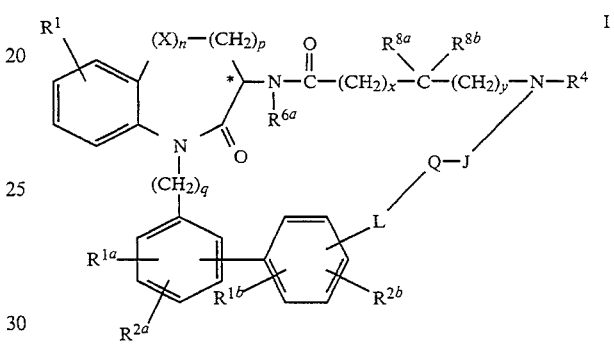

n is 0 or 1;
p is 0 to 3;
q is 0 to 4;
x is 0 to 3;
y is 0 to 3;

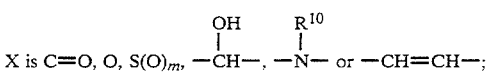

m is 0 to 2;

$R^1$, $R^2$, $R^{1a}$, $R^{2a}$, $R^{1b}$ and $R^{2b}$ are independently hydrogen, halogen, $C_1-C_7$ alkyl, $C_1-C_3$ perfluoroalkyl, $C_1-C_3$ perfluoroalkoxy, $-S(O)_m R^{7a}$, cyano, nitro, $R^{7b}O(CH_2)_v-$, $R^{7b}COO(CH_2)_v-$, $R^{7b}OCO(CH_2)_v-$, $R^{4a}R^{4b}N(CH_2)_v-$, $R^{7b}CON(R^{4b})(CH_2)_v-$, $R^{4a}R^{4b}NCO(CH_2)_v-$, phenyl or substituted phenyl where the phenyl substituents are from 1 to 3 of halogen, $C_1-C_6$ alkyl, $C_1-C_6$ alkoxy, or hydroxy; and v is 0 to 3; $R^{7a}$ and $R^{7b}$ are independently hydrogen, $C_1-C_3$ perfluoroalkyl, $C_1-C_6$ alkyl, substituted $C_1-C_6$ alkyl where the substituents am phenyl or substituted phenyl; phenyl or substituted phenyl where the phenyl substituents are from 1 to 3 of halogen, $C_1-C_6$ alkyl, $C_1-C_6$ alkoxy or hydroxy;

$R^4$, $R^{4a}$ and $R^{4b}$ are independently hydrogen, phenyl, substituted phenyl, $C_1-C_{10}$ alkyl, substituted $C_1-C_{10}$ alkyl, $C_3-C_{10}$ alkenyl, substituted $C_3-C_{10}$ alkenyl, $C_3-C_{10}$ alkynyl or substituted $C_3-C_{10}$ alkynyl where the substituents on the phenyl, alkyl, alkenyl or alkynyl are from 1 to 5 of hydroxy, $C_1-C_6$ alkoxy, $C_3-C_7$ cycloalkyl, fluoro, $R^1$, $R^2$ independently disubstituted phenyl, $R^1$, $R^2$ independently disubstimted phenyl $C_1-C_3$ alkoxy, $C_1-C_{20}$ alkanoyloxy, $C_1-C_5$ alkoxycarbonyl, carboxy, formyl or $-NR^{10}R^{11}$ where $R^1$ and $R^2$ are as defined above and $R^{10}$ and $R^{11}$ are independently hydrogen, $C_1$-$C_6$ alkyl, phenyl, phenyl $C_1$-$C_6$ alkyl, $C_1$-$C_5$ alkoxycarbonyl or $C_1$-$C_5$ alkanoyl-$C_1$-$C_6$ alkyl; or $R^{4a}$ and $R^{4b}$, or $R^{4b}$ and $R^{7b}$ can be taken together to form —$(CH_2)_r$—B—$(CH_2)_s$— where B is $CHR^1$, O, $S(O)_m$ or $NR^{10}$, m is 0, 1 or 2, r and s are independently 0 to 3 and $R^1$ and $R^{10}$ are as defined;

L is A or $C_1$-$C_6$ alkylene substituted with A;

A is

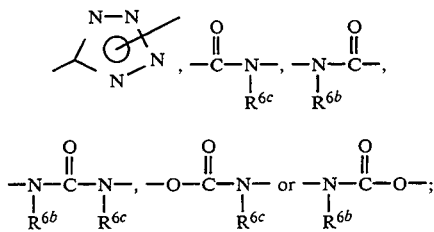

Q is a single bond or

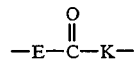

where K is O, S or N—$R^{6d}$;

E and J are independently $C_1$-$C_6$ alkylene or substituted $C_1$-$C_6$ alkylene where the substituents are from 1 to 5 of hydroxy, $C_1$-$C_6$ alkoxy, $C_3$-$C_7$ cycloalkyl, fluoro, $R^1$, $R^2$ independently disubstituted phenyl, $R^1$, $R^2$ independently disubstituted phenyl $C_1$-$C_3$ alkoxy, $C_1$-$C_{20}$ alkanoyloxy, $C_1$-$C_5$ alkoxycarbonyl, carboxy, formyl or —$NR^{10}R^{11}$ where $R^1$, $R^2$, $R^{10}$ and $R^{11}$ are as defined;

$R^{6a}$, $R^{6b}$, $R^{6c}$ and $R^{6d}$ are independently hydrogen, $C_1$-$C_{10}$ alkyl, phenyl or phenyl $C_1$-$C_{10}$ alkyl; and $R^{6b}$ and $R^{6c}$ can be taken together to form —$(CH_2)_t$— where t is 2 to 6;

$R^{8a}$ and $R^{8b}$ are independently hydrogen, trifluoromethyl, $R^1$, $R^2$ independently disubstituted phenyl, $C_1$-$C_{10}$ alkyl, substituted $C_1$-$C_{10}$ alkyl where the substituents are from 1 to 3 of imidazolyl, indolyl, hydroxy, fluoro, $S(O)_m R^{7a}$, $C_1$-$C_6$ alkoxy, $C_3$-$C_7$ cycloalkyl, $R^1$, $R^2$ independently disubstituted phenyl, $R^1$, $R^2$ independently disubstituted phenyl $C_1$-$C_3$ alkoxy, $C_1$-$C_5$ alkanoyloxy, $C_1$-$C_5$ alkoxycarbonyl, carboxy, formyl or —$NR^{10}R^{11}$ where $R^1$, $R^2$, $R^{7a}$, $R^{10}$, $R^{11}$ and m are as defined above; or $R^{8a}$ and $R^{8b}$ can be taken together to form —$(CH_2)_t$— where t is 2 to 6; and $R_{8a}$ and $R_{8b}$ can independently be joined to $R^4$ to form alkylene bridges wherein the bridge contains from one to five carbon atoms; and pharmaceutically acceptable salts thereof.

In the above structural formula and throughout the instant specification, the following terms have the indicated meanings:

The alkyl groups specified above are intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl, and the like.

The alkoxy groups specified above are intended to include those alkoxy groups of the designated length in either a straight or branched configuration. Exemplary of such alkoxy groups are methoxy, ethoxy, propoxy, isopropoxy, butoxy, isobutoxy, tertiary butoxy, pentoxy, isopentoxy, hexoxy, isohexoxy and the like.

The alkylene groups specified above are intended to include those divalent groups of the designated length in either a straight or branched configuration. Exemplary of such alkylene groups are methylene, ethylene, propa-1,3-diyl, propa-1,2-diyl, buta-1,4-diyl, penta-1,5-diyl, 2,2-dimethylethylene, 1,1,2,2-tetramethylethylene and the like.

The term "halogen" is intended to include the halogen atoms fluorine, chlorine, bromine and iodine.

Certain of the above defined terms may occur more than once in the above formula and upon such occurrence each term shall be defined independently of the other.

Preferred compounds of the instant invention are realized when in the above structural formula:

n is 0 or 1;
p is 0 to 3;
q is 0 to 2;
x is 0 to 2;
y is 0 to 2;

X is O, $S(O)_m$, —$\overset{R^{10}}{\underset{|}{N}}$— or —CH=CH—;

m is 0 to 2;

$R^1$, $R^2$, $R^{1a}$, $R^{2a}$, $R^{1b}$ and $R^{2b}$ are independently hydrogen, halogen, $C_1$-$C_7$ alkyl, $C_1$-$C_3$ perfluoroalkyl, —$S(O)_m R^{7a}$, $R^{7b}O(CH_2)_v$—, $R^{7b}COO(CH_2)_v$—, $R^{7b}OCO(CH_2)_v$—, phenyl or substituted phenyl where the phenyl substituents are from 1 to 3 of halogen, $C_1$-$C_6$ alkyl, $C_1$-$C_6$ alkoxy, or hydroxy; and v is 0 to 2;

$R^{7a}$ and $R^{7b}$ are independently hydrogen, $C_1$-$C_3$ perfluoroalkyl, $C_1$-$C_6$ alkyl, substituted $C_1$-$C_6$ alkyl where the substituents are phenyl; phenyl; $R^4$, $R^{4a}$ and $R^{4b}$ are independently hydrogen, phenyl, substituted phenyl, $C_1$-$C_{10}$ alkyl or substituted $C_1$-$C_{10}$ alkyl where the substituents on the phenyl or alkyl are from 1 to 5 of hydroxy, $C_1$-$C_6$ alkoxy, $C_3$-$C_7$ cycloalkyl, fluoro, $R^1$, $R^2$ independently disubstimted phenyl, $R^1$, $R^2$ independently disubstimted phenyl $C_1$-$C_3$ alkoxy, $C_1$-$C_{20}$ alkanoyloxy, $C_1$-$C_5$ alkoxycarbonyl, carboxy or formyl where $R^1$ and $R^2$ are as defined above;

L is A or $C_1$-$C_6$ alkylene substituted with A;

A is

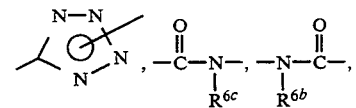

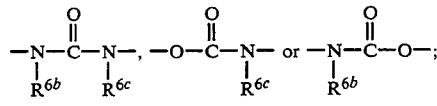

Q is a single bond or

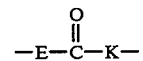

where K is O or N—$R^{6d}$;

E and J are independently $C_1$-$C_6$ alkylene or substituted $C_1$-$C_6$ alkylene where the substituents are from 1 to 3 of hydroxy, $C_1$-$C_3$ alkoxy, fluoro, $R^1$, $R^2$ independently disubstituted phenyl, $C_1$-$C_{10}$ alkanoyloxy, $C_1$–$C_5$ alkoxycarbonyl, carboxy or formyl where $R^1$ and $R^2$ are as defined;

$R^{6a}$, $R^{6b}$, $R^{6c}$ and $R^{6d}$ are independently hydrogen, $C_1$–$C_{10}$ alkyl or phenyl $C_1$–$C_{10}$ alkyl; and $R^{6b}$ and $R^{6c}$ can be taken together to form —$(CH_2)_t$— where t is 2 to 4;

$R^{8a}$ and $R^{8b}$ are independently hydrogen, $C_1$–$C_{10}$ alkyl, substituted $C_1$–$C_{10}$ alkyl where the substituents are from 1 to 3 of imidazolyl, indolyl, hydroxy, fluoro, —$S(O)_m R^{7a}$, $C_1$–$C_6$ alkoxy, $C_3$–$C_7$ cycloalkyl, $R^1$, $R^2$ independently disubstituted phenyl, $R^1$, $R^2$ independently disubstituted phenyl $C_1$–$C_3$ alkoxy, $C_1$–$C_5$ alkanoyloxy, $C_1$–$C_5$ alkoxycarbonyl, carboxy, formyl or —$NR^{10}R^{11}$ where $R^1$, $R^2$, $R^{7a}$, $R^{10}$, $R^{11}$ and m are as defined above; or $R^{8a}$ and $R^{8b}$ can be taken together to form —$(CH_2)_t$— where t is 2 to 4; and $R^{8a}$ and $R^{8b}$ can independently be joined to $R^4$ to form alkylene bridges wherein the bridge contains from one to five carbon atoms; and pharmaceutically acceptable salts thereof.

Additional preferred compounds are realized in the above structural formula when:

n is 0 or 1;
p is 0 to 2;
q is 0 to 2;
x is 0 to 2;
y is 0 to 2;
X is $S(O)_m$ or —CH=CH—; m is 0 or 1;
$R^1$, $R^2$, $R^{1a}$, $R^{2a}$, $R^{1b}$ and $R^{2b}$ are independently hydrogen, halogen, $C_1$–$C_7$ alkyl, $C_1$–$C_3$ perfluoroalkyl, —$S(O)_m R^{7a}$, $R^{7b}O(CH_2)_v$—, $R^{7b}COO(CH_2)_v$—, $R^{7b}OCO(CH_2)_v$—, phenyl or substituted phenyl where the phenyl substituents are from 1 to 3 of halogen, $C_1$–$C_6$ alkyl, $C_1$–$C_6$ alkoxy, or hydroxy; and v is 0 to 2;

$R^{7a}$ and $R^{7b}$ are independently hydrogen, $C_1$–$C_6$ alkyl or substituted $C_1$–$C_6$ alkyl where the substituents are phenyl;

$R^4$, $R^{4a}$ and $R^{4b}$ are independently hydrogen, $C_1$–$C_{10}$ alkyl or substituted $C_1$–$C_{10}$ alkyl where the substituents are from 1 to 5 of hydroxy, $C_1$–$C_6$ alkoxy, fluoro, $R^1$, $R^2$ independently disubstituted phenyl, $C_1$–$C_{20}$ alkanoyloxy, $C_1$–$C_5$ alkoxycarbonyl or carboxy where $R^1$ and $R^2$ are as defined above;

L is A or $C_1$–$C_6$ alkylene substituted with A;
A is

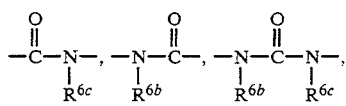

Q is a single bond or

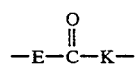

where K is O or N—$R^{6d}$;

E and J are independently $C_1$–$C_6$ alkylene or substituted $C_1$–$C_6$ alkylene where the substituents are from 1 to 3 of hydroxy, fluoro, $R^1$, $R^2$ independently disubstituted phenyl, $C_1$–$C_5$ alkanoyloxy, $C_1$–$C_5$ alkoxycarbonyl or carboxy where $R^1$ and $R^2$ are as defined;

$R^{6a}$, $R^{6b}$, $R^{6c}$ and $R^{6d}$ are independently hydrogen or $C_1$–$C_{10}$ alkyl;

$R^{8a}$ and $R^{8b}$ are independently hydrogen, $C_1$–$C_{10}$ alkyl, substituted $C_1$–$C_{10}$ alkyl where the substituents are from 1 to 3 of imidazolyl, indolyl, hydroxy, fluoro, —$S(O)_m R^{7a}$, $C_1$–$C_6$ alkoxy, $C_3$–$C_7$ cycloalkyl, $R^1$, $R^2$ independently disubstituted phenyl, $R^1$, $R^2$ independently disubstituted phenyl $C_1$–$C_3$ alkoxy, $C_1$–$C_5$ alkanoyloxy, $C_1$–$C_5$ alkoxycarbonyl, carboxy, formyl or —$NR^{10}R^{11}$ where $R^1$, $R^2$, $R^{7a}$, $R^{10}$, $R^{11}$ and m are as defined above; or $R^{8a}$ and $R^{8b}$ can be taken together to form —$(CH_2)_t$— where t is 2; and $R^{8a}$ and $R^{8b}$ can independently be joined to $R^4$ to form alkylene bridges wherein the bridge contains from one to five carbon atoms; and pharmaceutically acceptable salts thereof.

Still further preferred compounds of the instant invention are realized in the above structural formula when;

n is 0 or 1;
p is 0 to 2;
q is 1;
x is 0 or 1;
y is 0 or 1;
X is $S(O)_m$ or —CH=CH—; m is 0 or 1;
$R^1$, $R^2$, $R^{1a}$, $R^{2a}$, $R^{1b}$ and $R^{2b}$ are independently hydrogen, halogen, $C_1$–$C_7$ alkyl, $C_1$–$C_3$ perfluoroalkyl, —$S(O)_m R^{7a}$, $R^{7b}O(CH_2)_v$—, $R^{7b}COO(CH_2)_v$—, phenyl or substituted phenyl where the substituents are from 1 to 3 of halogen, $C_1$–$C_6$ alkyl, $C_1$–$C_6$ alkoxy or hydroxy and v is 0 or 1;

$R^{7a}$ and $R^{7b}$ are independently hydrogen, $C_1$–$C_6$ alkyl or substituted $C_1$–$C_6$ alkyl where the substituents are phenyl;

$R^4$, $R^{4a}$ and $R^{4b}$ are independently hydrogen, $C_1$–$C_{10}$ alkyl or substituted $C_1$–$C_{10}$ alkyl where the substituents are from 1 to 3 of hydroxy, $C_1$–$C_3$ alkoxy, fluoro, $R^1$, $R^2$ independently disubstituted phenyl, $C_1$–$C_{10}$ alkanoyloxy, $C_1$–$C_5$ alkoxycarbonyl or carboxy where $R^1$ and $R^2$ are as defined above;

L is A or $C_1$–$C_4$ alkylene substituted with A;
A is

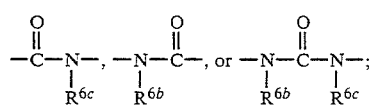

Q is

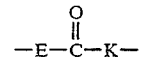

where K is O;

E and J are independently $C_1$–$C_4$ alkylene or substituted $C_1$–$C_4$ alkylene where the substituents are from 1 to 3 of hydroxy, fluoro, $R^1$, $R^2$ independently disubstituted phenyl, $C_1$–$C_5$ alkanoyloxy, $C_1$–$C_5$ alkoxycarbonyl or carboxy where $R^1$ and $R^2$ are as defined;

$R^{6a}$, $R^{6b}$, $R^{6c}$ and $R^{6d}$ are hydrogen;

$R^{8a}$ and $R^{8b}$ are independently hydrogen, $C_1$–$C_{10}$ alkyl, substituted $C_1$–$C_{10}$ alkyl where the substituents are from 1 to 3 of imidazolyl, indolyl, hydroxy, fluoro, —$S(O)_m R^{7a}$, $C_1$–$C_6$ alkoxy, $C_3$–$C_7$ cycloalkyl, $R^1$, $R^2$ independently disubstituted phenyl, $C_1$–$C_5$ alkanoyloxy, $C_1$–$C_5$ alkoxycarbonyl or carboxy, where $R^1$, $R^2$, $R^{7a}$, and m are as defined; or $R^{8a}$ and $R^{8b}$ can be taken together to form —$(CH_2)_t$— where t is 2; and $R^{8a}$ and $R^{8b}$

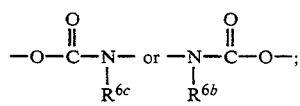

can independently be joined to R⁴ to form alkylene bridges wherein the bridge contains from one to five carbon atoms; and pharmaceutically acceptable salts thereof.

Representative preferred growth hormone releasing compounds of the present invention include the following:

1. (R)-8,9,10,11,13,14,15,16-Octahydro-10,10-dimethyl-6H-23,26-etheno-14,21-methanodibenzo[1,t][1,4,8,14]tetraazacyclodocosine-5,12,29(7H,22H)-trione;
2. (R)-8,9,10,11,13,14,15,16-Octahydro-10,10-dimethyl-18-fluoro-6H-23,26-etheno-14,21-methanodibenzo[1,t][1,4,8,14]tetraazacyclodocosine-5,12,29(7H,22H)-trione;
3. (R)-8,9,10,11,13,14,15,16-Octahydro-10,10-dimethyl-18-trifluoromethyl-6H-23,26-etheno-14,21-methanodibenzo[1,t][1,4,8,14]tetraazacyclodocosine-5,12,29(7H,22H)-trione;
4. (R)-8,9,10,11,13,14,15,16-Octahydro-10,10-dimethyl-18-methoxy-6H-23,26-etheno-14,21-methanodibenzo[1,t][1,4,8,14]tetraazacyclodocosine-5,12,29(7H,22H)-trione;
5. (R)-8,9,10,11,13,14,15,16-Octahydro-10,10-dimethyl-18-methylthio-6H-23,26-etheno-14,21-methanodibenzo[1,t][1,4,8,14]tetraazacyclodocosine-5,12,29(7H,22H)-trione;
6. (10R,17R)-11,12,13,14,16,17,18,19-Octahydro-10,13,13-trimethyl-6H-26,29-etheno-17,24-methanodibenz[1,t][1,4,8,14,23]oxatetraazacyclopentacosine-5,8,15,32(7H,10H,25H)-tetrone;
7. (10R,17R)-11,12,13,14,16,17,18,19-Octahydro-10,13,13-trimethyl-21-methylthio-6H-26,29-etheno-17,24-methanodibenz[1,t][1,4,8,14,23]oxatetraazacyclopentacosine-5,8,15,32(7H,10H,25H)-tetrone;
8. (10R,17R)-11,12,13,14,16,17,18,19-Octahydro-10,13,13-trimethyl-21-methoxy-6H-26,29-etheno-17,24-methanodibenz[1,t][1,4,8,14,23]oxatetraazacyclopentacosine-5,8,15,32(7H,10H,25H)-tetrone;
9. (10R,17R)-11,12,13,14,16,17,18,19-Octahydro-10,13,13-trimethyl-21-fluoro-6H-26,29-etheno-17,24-methanodibenz[1,t][1,4,8,14,23]oxatetraazacyclopentacosine-5,8,15,32(7H,10H,25H)-tetrone;
10. (10R,17R)-11,12,13,14,16,17,18,19-Octahydro-10,13,13-trimethyl-21-trifluoromethyl-6H-26,29-etheno-17,24-methanodibenz[1,t][1,4,8,14,23]oxatetraazacyclopentacosine-5,8,15,32(7H,10H,25H)-tetrone;
11. (10R,17R)-11,12,13,14,16,17,18,19-Octahydro-13,13-dimethyl-6H-26,29-etheno-17,24-methanodibenz[1,t][1,4,8,14,23]oxatetraazacyclopentacosine-5,8,15,32(7H,10H,25H)-tetrone;
12. (10R,17R)-11,12,13,14,16,17,18,19-Octahydro-13,13-dimethyl-21-methylthio-6H-26,29-etheno-17,24-methanodibenz[1,t][1,4,8,14,23]oxatetraazacyclopentacosine-5,8,15,32(7H,10H,25H)-tetrone;
13. (10R,17R)-11,12,13,14,16,17,18,19-Octahydro-13,13-dimethyl-21-methoxy-6H-26,29-etheno-17,24-methanodibenz[1,t][1,4,8,14,23]oxatetraazacyclopentacosine-5,8,15,32(7H,10H,25H)-tetrone;
14. (10R,17R)-11,12,13,14,16,17,18,19-Octahydro-13,13-dimethyl-21-fluoro-6H-26,29-etheno-17,24-methanodibenz[1,t][1,4,8,14,23]oxatetraazacyclopentacosine-5,8,15,32(7H,10H,25H)-tetrone;
15. (10R,17R)-11,12,13,14,16,17,18,19-Octahydro-13,13-dimethyl-21-trifluoromethyl-6H-26,29-etheno-17,24-methanodibenz[1,t][1,4,8,14,23]oxatetraazacyclopentacosine-5,8,15,32(7H,10H,25H)-tetrone;
16. (11R,18R)-7,8,12,13,14,15,17,18,19,20-Decahydro-11,14,14-trimethyl-27,30-etheno-18,25-methano-25H-dibenz[1,t][1,4,8,14,23]oxatetraazacyclohexacosine-5,9,16,33(6H,11H,26H)-tetrone;
17. (11R,18R)-7,8,12,13,14,15,17,18,19,20-Decahydro-22-methoxy-11,14,14-trimethyl-27,30-etheno-18,25-methano-25H:dibenz[1,t][1,4,8,14,23]oxatetraazacyclohexacosine-5,9,16,33(6H,11H,26H)-tetrone;
18. (11R,18R)-7,8,12,13,14,15,17,18,19,20-Decahydro-22-methylthio-11,14,14-trimethyl-27,30-etheno-18,25-methano-25H-dibenz[1,t][1,4,8,14,23]oxatetraazacyclohexacosine-5,9,16,33(6H,11H,26H)-tetrone;
19. (11R,18R)-7,8,12,13,14,15,17,18,19,20-Decahydro-22-fluoro-11,14,14-trimethyl-27,30-etheno-18,25-methano-25H-dibenz[1,t][1,4,8,14,23]oxatetraazacyclohexacosine-5,9,16,33(6H,11H,26H)-tetrone;
20. (11R,18R)-7,8,12,13,14,15,17,18,19,20-Decahydro-22-trifluoromethyl-11,14,14-trimethyl-27,30-etheno-18,25-methano-25H-dibenz[1,t][1,4,8,14,23]oxatetraazacyclohexacosine-5,9,16,33(6H,11H,26H)-tetrone;
21. (11R,18R)-7,8,12,13,14,15,17,18,19,20-Decahydro-14,14-dimethyl-27,30-etheno-18,25-methano-25H-dibenz[1,t[1,4,8,14,23]oxatetraazacyclohexacosine-5,9,16,33(6H,11H,26H)-tetrone;
22. (11R,18R)-7,8,12,13,14,15,17,18,19,20-Decahydro-22-methoxy-14,14-dimethyl-27,30-etheno-18,25-methano-25H-dibenz[1,t][1,4,8,14,23]oxatetraazacyclohexacosine-5,9,16,33(6H,11H,26H)-tetrone;
23. (11R,18R)-7,8,12,13,14,15,17,18,19,20-Decahydro-22-methylthio-14,14-dimethyl-27,30-etheno-18,25-methano-25H-dibenz[1,t][1,4,8,14,23]oxatetraazacyclohexacosine-5,9,16,33(6H,11H,26H)-tetrone;
24. (11R,18R)-7,8,12,13,14,15,17,18,19,20-Decahydro-22-fluoro-14,14-dimethyl-27,30-etheno-18,25-methano-25H-dibenz[1,t][1,4,8,14,23]oxatetraazacyclohexacosine-5,9,16,33(6H,11H,26H)-tetrone;
25. (11R,18R )-7,8,12,13,14,15,17,18,19,20-Decahydro-22-trifluoromethyl-14,14-dimethyl-27,30-etheno-18,25-methano-25H-dibenz-[1,t][1,4,8,14,23]oxatetraazacyclohexacosine-5,9,16,33(6H,11H,26H)-tetrone;
26. (12R,19R)-8,9,13,14,15,16,18,19,20,21-Decahydro-12,15,15-trimethyl-6H-28,31-etheno-19,26-methanodibenz[1,t][1,4,8,14,23]oxatetraazacycloheptacosine-5,10,17,34-(7H,12H,27H)-tetrone;
27. (12R,19R)-8,9,13,14,15,16,18,19,20,21-Decahydro-23-fluoro-12,15,15-trimethyl-6H-28,31-etheno-19,26-methanodibenz[1,t][1,4,8,14,23]oxatetraazacycloheptacosine-5,10,17,34(7H,12H,27H)-tetrone;
28. (12R,19R)-8,9,13,14,15,16,18,19,20,21-Decahydro-23-trifluoromethyl-12,15,15-trimethyl-6H-28,31-etheno-19,26methanodibenz[1,t][1,4,8,14,2-

29. (12R,19R)-8,9,13,14,15,16,18,19,20,21-Decahydro-23-methoxy12,15,15-trimethyl-6H-28,31-etheno-19,26-methanodibenz[1,t][1,4,8,14,23]oxatetraazacycloheptacosine-5,10,17,34(7H,12H,27H)-tetrone;

30. (12R,19R)-8,9,13,14,15,16,18,19,20,21-Decahydro-23-methylthio-12,15,15-trimethyl-6H-28,31-etheno-19,26-methanodibenz[1,t][1,4,8, 14,23]oxatetraazacycloheptacosine-5,10,17,34(7H,12H,27H)-tetrone;

31. (12R,19R)-8,9,13,14,15,16,18,19,20,21-Decahydro-15,15-dimethyl-6H-28,31-etheno-19,26-methanodibenz[1,t][1,4,8,14,23]oxatetraazacycloheptacosine-5,10,17,34(7H,12H,27H)-tetrone;

32. (12R,19R)-8,9,13,14,15,16,18,19,20,21-Decahydro-23-fluoro-15,15-dimethyl-6H-28,31-etheno-19,26-methanodibenz[1,t][1,4,8,14,23]oxatetraazacycloheptacosine-5,10,17,34(7H,12H,27H)-tetrone;

33. (12R,19R)-8,9,13,14,15,16,18,19,20,21-Decahydro-23-trifluoromethyl-15,15-dimethyl-6H-28,31-etheno-19,26methanodibenz[1,t][1,4,8,14,23]oxatetraazacycloheptacosine-5,10,17,34(7H,12H,27H)-tetrone;

34. (12R, 19R)-8,9,13,14,15,16,18,19,20,21-Decahydro-23-methoxy-15,15-dimethyl-6H-28,31-etheno-19,26-methanodibenz[1,t][1,4,8,14,23]oxatetraazacycloheptacosine-5,10,17,34(7H,12H,27H)-tetrone;

35. (12R,19R )-8,9,13,14,15,16,18,19,20,21-Decahydro-23-methylthio-15,15-dimethyl-6H-28,31-etheno-19,26-methanodibenz[1,t][1,4,8,14,23]oxatetraazacycloheptacosine-5,10,17,34(7H,12H,27H)-tetrone;

36. (R)-11,12,13,14,15,16,18,19,20,21-Decahydro-15,15-dimethyl-9H,27H-28,31-etheno-19,26-methano-8,5-nitrilo-5H-dibenzo[q,y][1,2,3,6,9,13,19]heptaazacycloheptacosine-10,17,34-trione;

37. (R)-11,12, 13,14,15,16,18,19,20,21-Decahydro-15,15-dimethyl-23-fluoro-9H,27H-28,31-etheno-19,26-methano-8,5-nitrilo-5H-dibenzo[q,y][1,2,3,6,9,13,19]heptaazacycloheptacosine-10,17,34-trione;

38. (R)-11,12,13,14,15,16,18,19,20,21-Decahydro-15,15-dimethyl-23-trifluoromethyl-9H,27H-28,31-etheno-19,26-methano-8,5-nitrilo-5H-dibenzo[q,y][1,2,3,6,9,13,19]heptaazacycloheptacosine-10,17,34-trione;

39. (R)-11,12,13,14,15,16,18,19,20,21-Decahydro-15,15-dimethyl-23-methoxy-9H,27H-28,31-etheno-19,26-methano-8,5-nitrilo-5H-dibenzo[q,y][1,2,3,6,9,13,19]heptaazacycloheptacosine-10,17,34-trione;

40. (R)-11,12,13,14,15,16,18,19,20,21-Decahydro-15,15-dimethyl-23-methylthio-9H,27H-28,31-etheno-19,26-methano-8,5-nitrilo-5H-dibenzo[q,y][1,2,3,6,9,13,19]heptaazacycloheptacosine-10,17,34-trione;

41. (12R,19R ) -5,8,9,13,14,15,16,18,19,20,21,27-Dodecahydro-12,15,15-trimethyl-6H-28,31-etheno-19,26-methanodibenz[1,t][1,4,8,14,23,25]oxapentaazacycloheptacosine-7,10,17,34(7H,12H)-tetrone;

42. (12R,19R)-5,8,9,13,14,15,16,18,19,20,21,27-Dodecahydro-23-methylthio-12,15,15-trimethyl-6H-28,31-etheno-19,26-methanodibenz[1,t][1,4,8,14,23,25]oxapentaazacycloheptacosine-7,10,17,34(7H,12H)-tetrone;

43. (12R,19R)-5,8,9,13,14,15,16,18,19,20,21,27-Dodecahydro-23methoxy-12,15,15-trimethyl-6H-28,31-etheno-19,26-methanodibenz[1,t][1,4,8,14,23,25]oxapentaazacycloheptacosine-7,10,17,34(7H,12H)-tetrone;

44. (12R,19R)-5,8,9,13,14,15,16,18,19,20,21,27-Dodecahydro-23-trifluoromethyl-12,15,15-trimethyl-6H-28,31-etheno-19,26methanodibenz[1,t][1,4,8,14,23,25]oxapentaazacycloheptacosine-7,10,17,34(7H,12H)-tetrone;

45. (12R, 19R )-5,8,9,13,14,15,16,18,19,20,21,27-Dodecahydro-15,15-dimethyl-6H-28,31-etheno-19,26-methanodibenz[1,t][1,4,8,14,23,25]oxapentaazacycloheptacosine-7,10,17,34(7H,12H)-tetrone;

46. (12R,19R)-5,8,9,13,14,15,16,18,19,20,21,27-Dodecahydro-23-methylthio-15,15-dimethyl-6H-28,31-etheno-19,26-methanodibenz[1,t][1,4,8,14,23,25]oxapentaazacycloheptacosine-7,10,17,34(7H,12H)-tetrone;

47. (12R,19R)-5,8,9,13,14,15,16,18,19,20,21,27-Dodecahydro-23-methoxy-15,15-dimethyl-6H-28,31-etheno-19,26-methanodibenz[1,t][1,4,8,14,23,25]oxapentaazacycloheptacosine-7,10,17,34(7H,12H)-tetrone;

48. (12R,19R)-5,8,9,13,14,15,16,18,19,20,21,27-Dodecahydro-23-fluoro-15,15-dimethyl-6H-28,31-etheno-19,26-methanodibenz[1,t][1,4,8,14,23,25]oxapentaazacycloheptacosine-7,10,17,34(7H,12H)-tetrone;

49. (13R,20R )-5,9,10,14,15,16,17,19,20,21,22,28-Dodecahydro-13,16,16-trimethyl-29,32-etheno-20,27-methano-27H-dibenz[1,t][1,4,8,14,23,25]oxapentaazacyclooctacosine-7,11,18,35(6H,8H,13H)-tetrone;

50. (13R,20R)-5,9,10,14,15,16,17,19,20,21,22,28-Dodecahydro-24-fluoro-13,16,16-trimethyl-29,32-etheno-20,27-methano-27H-dibenz[1,t][1,4,8,14,23,25]oxapentaazacyclooctacosine-7,11,18,35(6H,8H,13H)-tetrone;

51. (13R,20R)-5,9,10,14,15,16,17,19,20,21,22,28-Dodecahydro-24-trifluoromethyl-13,16,16-trimethyl-29,32-etheno-20,27-methano-27H-dibenz[1,t][1,4,8,14,23,25]oxapentaazacyclooctacosine-7,11,18,35(6H,8H,13H)-tetrone;

52. (13R,20R)-5,9,10,14,15,16,17,1,9,20,21,22,28-Dodecahydro-24-methoxy-13,16,16-trimethyl-29,32-etheno-20,27-methano-27H-dibenz[1,t][1,4,8,14,23,25]oxapentaazacyclooctacosine-7,11,18,35(6H,8H,13H)-tetrone;

53. (13R,20R )-5,9,10,14,15,16,17,19,20,21,22,28-Dodecahydro-24-methylthio-13,16,16-trimethyl-29,32-etheno-20,27-methano-27H-dibenz[1,t[1,4,8,14,23,25]oxapentaazacyclooctacosine-7,11,18,35(6H,8H,13H)-tetrone;

54. (13R,20R)-5,9,10,14,15,16,17,19,20,21,22,28-Dodecahydro-16,16-dimethyl-29,32-etheno-20,27-methano-27H-dibenz[1t][1,4,8,14,23,25]oxapentaazacyclooctacosine-7,11,18,35(6H,8H,13H)-tetrone;

55. (13R,20R)-5,9,10,14,15,16,17,19,20,21,22,28-Dodecahydro-24-fluoro-16,16-dimethyl-29,3 2-etheno-20,27-methano-27H-dibenz[1,t][1,4,8,14,23,25]oxapentaazacyclooctacosine-7,11,18,35(6H,8H,13H)-tetrone;

56. (13R,20R)-5,9,10,14,15,16,17,19,20,21,22,28-Dodecahydro-24-trifluoromethyl-16,16-dimethyl-29,3 2-etheno-20,27-methano-27H-dibenz[1,t][1,4,8,14,23,25]oxapentaazacyclooctacosine-7,11,18,35(6H,8H,13H)-tetrone;

57. (13R,20R)-5,9,10,14,15,16,17,19,20,21,22,28-Dodecahydro-24-methoxy-16,16-dimethyl-29,32-etheno-20,27-methano-27H-dibenz[1,t][1,4,8,14,23,25]oxapentaazacyclooctacosine-7,11,18,35(6H,8H,13H)-tetrone;

58. (13R,20R)-5,9,10,14,15,16,17,19,20,21,22,28--Dodecahydro-24-methylthio-16,16-dimethyl-29,32-etheno-20,27-methano-27H-dibenz[1,t][1,4,8,14,23,25]oxapentaazacyclooctacosine-7,11,18,35(6H,8H,13H)-tetrone;

59. (12R,19S)-8,9,13,14,15,16, 19,20-Octahydro-12,15,15-trimethyl-6H,12H-28,31-etheno-19,26-methanodibenz[1,t][1,11,4,8,14,23]-oxathiatetraazacycloheptacosine-5,10,17,34(7H,18H,27H)-tetrone;

60. (12R, 19 S )-8,9,13,14,15,16, 19,20-Octahydro-23-methoxy-12,15,15-trimethyl-6H,12H-28,31-etheno-19,26-methanodibenz[1,t][1,11,4,8,14,23]oxathiatetraazacycloheptacosine-5,10,17,34(7H,18H,27H)-tetrone;

61. (12R,19S)-8,9,13,14,15,16,19,20-Octahydro-23--trifluoromethyl-12,15,15-trimethyl-6H,12H-28,31-etheno-19,26-methanodibenz[1,t][1,11,4,8,14,23]oxathiatetraazacycloheptacosine-5,10,17,34(7H,18H,27H)-tetrone;

62. (12R,19S)-8,9,13,14,15,16, 19,20-Octahydro-23-methylthio-12,15,15-trimethyl-6H,12H-28,31-etheno-19,26-methanodibenz[1,t][1,11,4,8,14,23]oxathiatetraazacycloheptacosine-5,10,17,34(7H,18H,27H)-tetrone;

63. (12R,19S)-8,9,13,14,15,16,19,20-Octahydro-15,15-dimethyl-6H,12H-28,31-etheno-19,26-methanodibenz[1,t][1,11,4,8,14,23]-oxathiatetraazacycloheptacosine-5,10,17,34(7H,18H,27H)-tetrone;

64. (12R,19S)-8,9,13,14,15,16,19,20-Octahydro-23-fluoro-15,15-dimethyl-6H,12H-28,31-etheno-19,26-methanodibenz[1,t][1,11,4,8,14,23]oxathiatetraazacycloheptacosine-5,10,17,34(7H,18H,27H)-tetrone;

65. (12R,19S)-8,9,13,14,15,16,19,20-Octahydro-23-methoxy-15,15-dimethyl-6H,12H-28,31-etheno-19,26-methanodibenz[l,t][1,11,4,8,14,23 ]oxathiatetraazacycloheptacosine-5,10,17,34(7H,18H,27H)-tetrone;

66. (12R,19S)-8,9,13,14,15,16,19,20-Octahydro-23-methylthio-15,15-dimethyl-6H,12H-28,31-etheno-19,26-methanodibenz[1,t][1,11,4,8,14,23]oxathiatetraazacycloheptacosine-5,10,17,34(7H,18H,27H)-tetrone;

67. (12R,19S)-5,8,9,13,14,15,16,19,20,27-Decahydro-12,15,15-trimethyl-6H,12H-28,31-etheno-19,26-methanodibenz[1,t][1,11,4,8,14,23,25]oxathiapentaazacycloheptacosine-7,10,17,34(7 H,18 H)-tetrone;

68. (12R,19S)-5,8,9,13,14,15,16,19,20,27-Decahydro-23-trifluoromethyl-12,15,15-trimethyl-6H,12H-28,31-etheno-19,26-methanodibenz [1,t][1,11,4,8,14,23,25]oxathiapentaazacycloheptacosine-7,10,17,34(7H,18H)-tetrone;

69. (12R,19S)-5,8,9,13,14,15,16,19,20,27-Decahydro-23-methoxy-12,15,15-trimethyl-6H,12H-28,31-etheno-19,26-methanodibenz[1,t][1,11,4,8,14,23,2-5]oxathiapentaazacycloheptacosine-7,10,17,34(7H,18H)-tetrone;

70. (12R,19S)-5,8,9,13,14,15,16,19,20,27-Decahydro-23-methylthio 12,15,15-trimethyl-6H,12H-28,31-etheno-19,26-methanodibenz[1,t][1,11,4,8,14,23,25]oxathiapentaazacycloheptacosine-7,10,17,34(7H,18H)-tetrone;

71. (12R, 19 S )-5,8,9,13,14,15,16,19,20,27-Decahydro-15,15-dimethyl-6H,12H-28,31-etheno-19,26-methanodibenz[1,t][1,11,4,8,14,23,25]oxathiapentaazacycloheptacosine-7,10,17,34(7H,18H)-tetrone;

72. (12R,19S)-5,8,9,13,14,15,16,19,20,27-Decahydro-23-fluoro-15,15-dimethyl-6H,12H-28,31-etheno-19,26-methanodibenz[1,t] [1,11,4,8,14,23,25]oxathiapentaazacycloheptacosine-7,10,17,34(7H,18H)-tetrone;

73. (12R,19S)-5,8,9,13,14,15,16,19,20,27-Decahydro-23-methoxy-15,15-dimethyl-6H,12H-28,31-etheno-19,26-methanodibenz[1,t][1,11,4,8,14,23,25]oxathiapentaazacycloheptacosine-7,10,17,34(7H,18H)-tetrone; and 74. (12R, 19S)-5,8,9,13,14,15,16, 19,20,27-Decahydro-23-methylthio-15,15-dimethyl-6H,12H-28,31-etheno-19,26-methanodibenz[1,t][1,11,4,8,14,23,2-5]oxathiapentaazacycloheptacosine-7,10,17,34(7H,18H)-tetrone.

Representative examples of the nomenclature employed are given below:

(R)-8,9,10,11,13,14,15,16-Octahydro-19-methyl-10,10-diphenyl-6H-23,26-etheno-14,21-methanodibenzo[1,t][1,4,8,14]tetraazacyclodocosine-5,12,29(7 H,22H)-trione

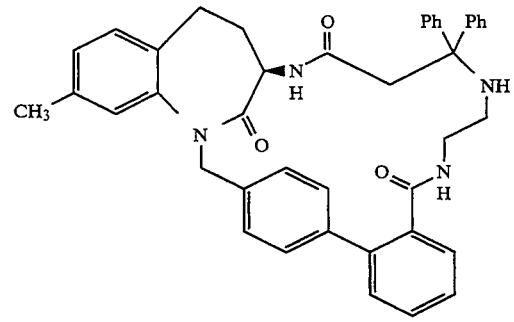

(R)-11,12,13,14,16,17,18,19-Octahydro-20-chloro-14,14-dimethyl-6H-26,29-etheno-17,24-methanodibenz[1,t][1,4,8,14,23]oxatetraazacyclopentacosine-5,8,15,32(7H,10H,25H)-tetrone

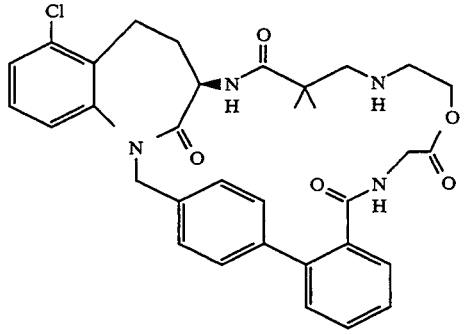

(R)-7,8,12,13,14,15,17,18,19,20-Decahydro-22-
methylsulfonyl-12,12-dimethyl-27,30-etheno-18,25-
methano-25H-dibenz[1,t][1,4,8,14,23]oxatet-
raazacyclohexacosine-5,9,16,33(6H,11H,26H)-
tetrone

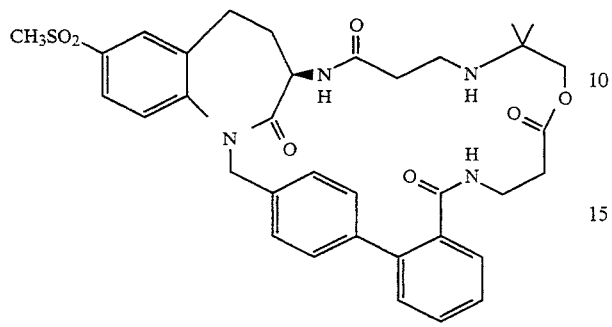

(R)-8,9,13,14,15,16,18,19,20,21-Decahydro-24-
bromo-16,16-dimethyl-6H-28,31-etheno-19,26-
methanodibenz[1,t][1,4,8,14,23]oxatetraazacy-
cloheptacosine-5,10,17,34(7H,12H,27H)-tetrone g

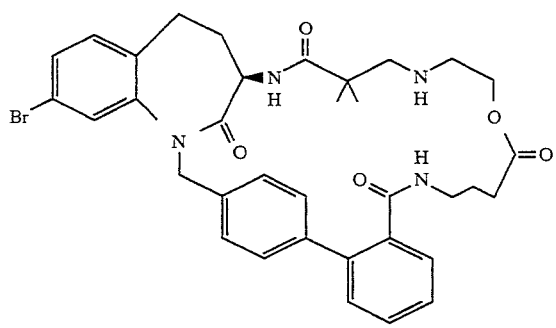

(R)-11,12,13,14,15,16,18,19,20,21-Decahydro-25-
fluoro-13,13-dimethyl-9H,27H-28,31-etheno-19,26-
methano-8,5-nitrilo-5H-dibenzo[q-
,y]1,2,3,6,9,13,19]heptaazacycloheptacosine-
10,17,34-trione

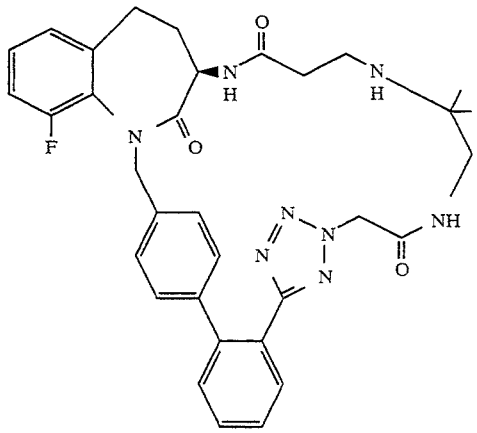

(R)-5,9,10,14,15,16,17,19,20,21,22,28-Dodecahydro-
25-iodo-13,13-dimethyl-29,32-etheno-20,27-
methano-27H-dibenz[1,t][1,4,8,14,23,25]-oxapen-
taazacyclooctacosine-7,11,18,35(6H,8H,13H)-
tetrone

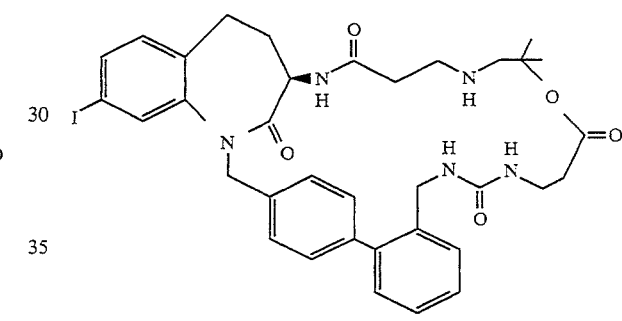

(S)-5,8,9,13,14,15,16,19,20,27-Decahydro-24-ethyl-
13,13-dimethyl-6H,12H-28,31-etheno-19,26-
methanodibenz[1,t][1,11,4,8,14,23,25]-oxathiapen-
taazacycloheptacosine-7,10,17,34(7H,18H)-tetrone

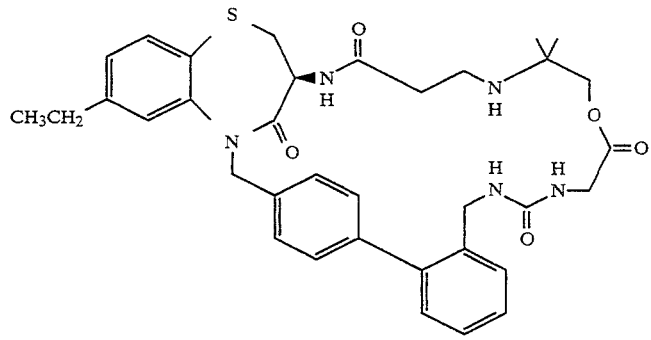

(R)-9,10,11,12,13,14,16,17,18,19-Decahydro-
7,7,14,14-tetramethyl-7H,25H-26,29-etheno-17,24-
methano-6,5-triazino-5H-dibenz[o,w][1,4,7,11,17-
]pentaazacyclopentacosine-8,15,32-trione

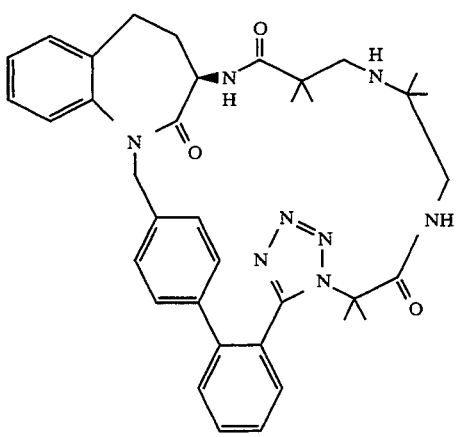

The compounds of the instant invention all have at least one asymmetric center as noted by the asterisk in the structural Formula I above. Additional asymmetric centers may be present on the molecule depending upon the nature of the various substituents on the molecule. Each such asymmetric center will produce two optical isomers and it is intended that all such optical isomers, as separated, pure or partially purified optical isomers or racemic mixtures thereof, be included within the ambit of the instant invention. In the case of the asymmetric center represented by the asterisk in Formula I, it has been found that the compound in which the amino substituent α to the carbonyl of the benzo-fused macrocycle is above the plane of the structure, as seen in Formula Ia, is more active and thus more preferred over the compound in which said substituent is below the plane of the structure. In the substituent $(X)_n$, when $n=0$, the asymmetric center is designated as the R-isomer. When $n=1$, this center will be designated according to the R/S rules as either R or S depending upon the value of X.

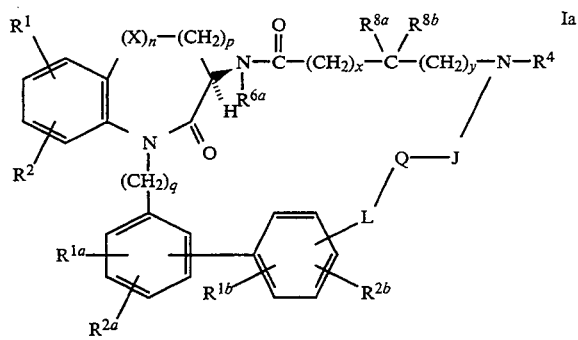

The instant compounds are generally isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, malonic and the like. In addition, certain compounds containing an acidic function such as a carboxy can be isolated in the form of their inorganic salt in which the counterion can be selected from sodium, potassium, lithium, calcium, magnesium and the like, as well as from organic bases.

The compounds (I) of the present invention are prepared from aminolactam intermediates such as those of formula II. The preparation of these intermediates is described by Fisher, et al, in U.S. Pat. No. 5,206,235 and references cited therein. Preparation of the compounds (I) of the present invention from the intermediates of formula II is described in the following Schemes.

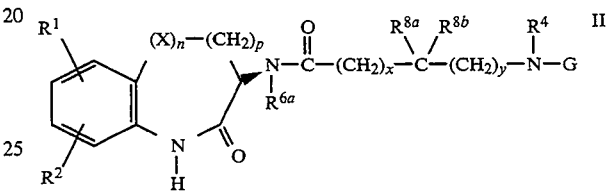

Elaboration of the compounds of formula II is described as shown in Scheme 1. Removal of the protecting group G is carried out by a number of methods known in the art to give intermediate 1. Removal of benzyloxycarbonyl groups is achieved, for example, by catalytic hydrogenation with hydrogen in the presence of a platinum or palladium catalyst in a protic solvent such as methanol or ethanol. In cases where catalytic hydrogenation is contraindicated by the presence of other potentially reactive functionality, removal of benzyloxycarbonyl groups is also achieved by treatment with a solution of hydrogen bromide in acetic acid. Removal of the t-butoxycarbonyl (BOC) protecting group is carried out by treatment of a solution in a solvent such as methylene chloride or methanol, with a strong acid, such as hydrochloric acid or trifluoroacetic acid. Conditions required to remove other protecting groups which may be present can be found in *Protective Groups in Organic Synthesis*, T. W. Greene, P. G. M. Wuts, John Wiley and Sons, New York, 1991.

SCHEME 1

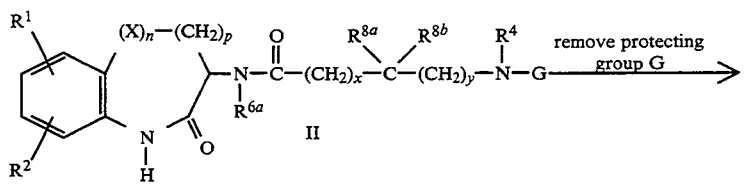

SCHEME 1 -continued

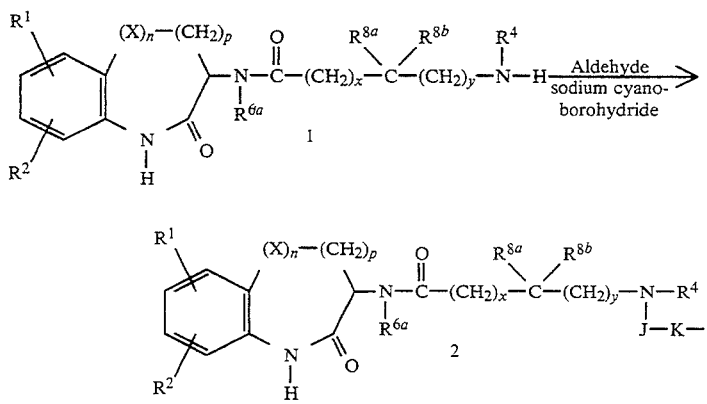

Intermediate 1 can be further elaborated to a new intermediate (2) which is substituted on the amino group. Reductive alkylation of 1 with an aldehyde is carried out under conditions known in the art; for example, by catalytic hydrogenation with hydrogen in the presence of platinum, palladium or nickel catalysts or with chemical reducing agents such as sodium cyanoborohydride in an inert solvent such as methanol or ethanol to give compound 2.

As shown in Scheme 2, intermediate 4 is prepared by treatment of the desired lactam intermediate 2 with an alkylating agent 3, wherein Y is a leaving group such as Cl, Br, I, O-methanesulfonyl or O-(p-toluenesulfonyl) and G'' is a protecting group. A description of such protecting groups may be found in *Protective Groups in Organic Synthesis*. Preparation of the alkylating agent 3 is described by Fisher, et al, in U.S. Pat. No. 5,206,235 and references cited therein. Alkylation of lactam 2 is conveniently carried out in anhydrous N,N-dimethylformamide (DMF) in the presence of a strong base such as sodium hydride or potassium t-butoxide for a period of 0.5 to 24 hours at temperatures of −5°–100° C. Substituents on the alkylating agent 3 may need to be protected during alkylation. Separation of unwanted side products and purification of the alkylated product 4 is achieved by chromatography on silica gel, employing flash chromatography (W. C. Still, M. Kahn, A. Mitra, *J. Org. Chem.* 1978, 43, 2923).

SCHEME 2

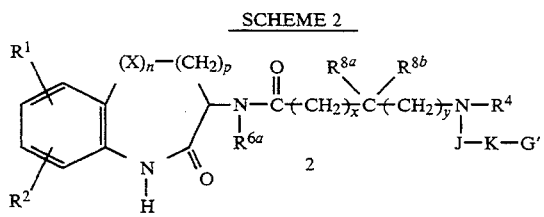

-continued
SCHEME 2

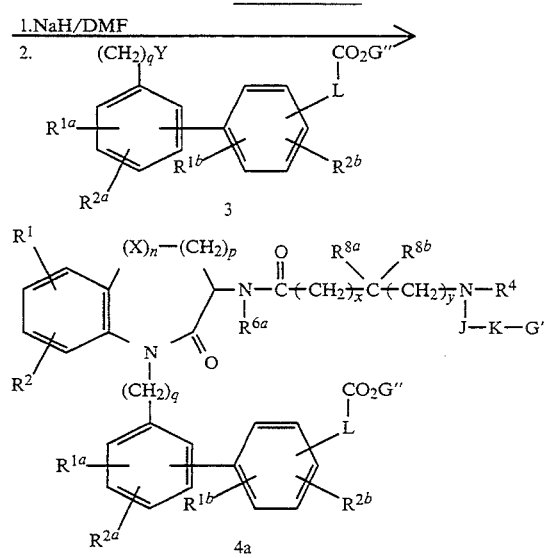

The formation of benzyl esters of alkylene amino acid 5 (wherein E is $C_1$–$C_6$ alkylene or substituted $C_1$–$C_6$ alkylene) is carried out as illustrated in Scheme 3. Treatment of amino acid 5 with oxalyl chloride and a catalytic amount of DMF in an inert solvent such as methylene chloride at room temperature for several hours followed by removal of solvent and treatment with benzyl alcohol affords the product which is isolated as its hydrochloride salt by precipitation with ether or another appropriate solvent. Further substitution on the amine to give ester 6 is achieved by the aforementioned reductive alkylation procedure. Intermediate 4 is further elaborated at the carboxyl group by removal of the protective group G'' followed by reaction with a coupling reagent such as benzotriazol-1-yloxytris(pyrrolidino)phosphonium hexafluorophosphate ("PyBOP") and ester 6 to afford the coupled product 7.

SCHEME 3

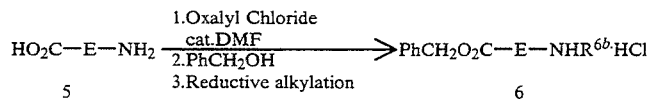

SCHEME 3

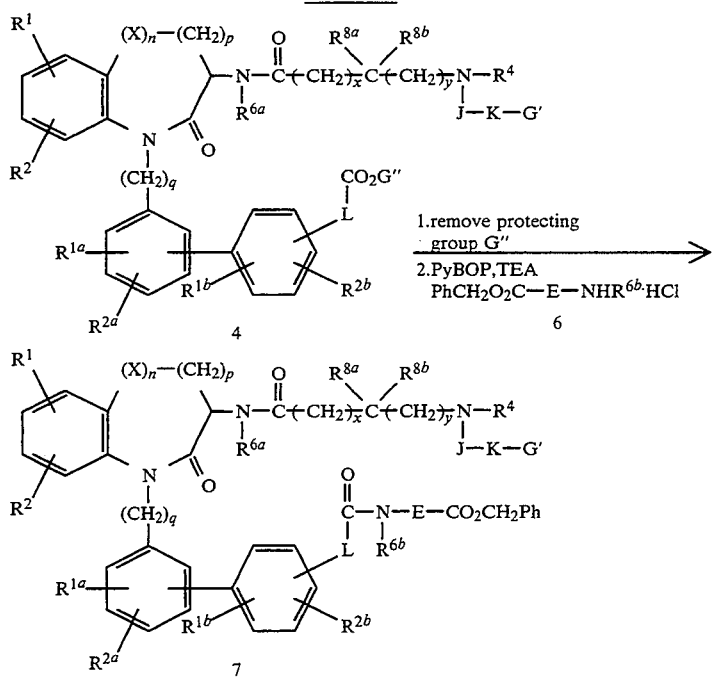

The subset of compounds of formula I described by formula III are prepared from intermediate 7 as illustrated in Scheme 4. Following removal of protecting group G' and cleavage of the benzyl ester by hydrogenolysis of intermediate 7, the resulting intermediate is cyclized using the conditions of Keck and Boden (*J. Org. Chem.*, 1985, 50, 2394–2395) to give compounds of formula III. For example, addition of the intermediate to a dilute refluxing chloroform solution of N-3-dimethylaminopropyl-N-ethylcarbodiimide (EDAC), 4-dimethylaminopyridine (DMAP) and 4-dimethylaminopyridine hydrochloride results in the formation of the macrocyclic compound of formula III. Purification and removal of unwanted by-products from compounds of formula III is performed by methods known to those skilled in the art, such as reverse phase high performance liquid chromatography (HPLC), silica gel flash column chromatography or size exclusion chromatography.

SCHEME 4

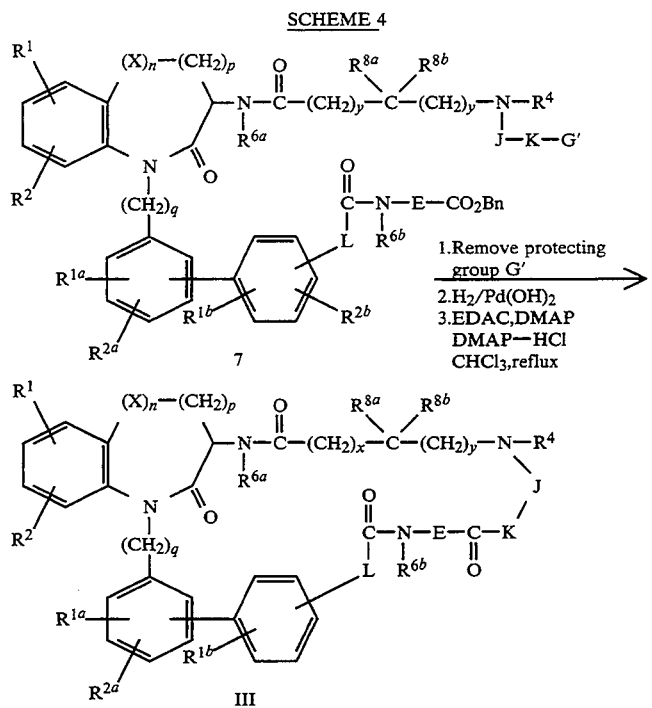

The subset of compounds of formula I described by formula IV is also prepared from intermediate 4 as illustrated in Scheme 5. Compounds of formula IV wherein K is N-R$^{6c}$ are prepared from intermediate 4 by sequential or simultaneous removal of both protecting groups followed by macrocyclization using the aforementioned conditions of Keck, et al.

Intermediates of formula V are prepared by the method of Fisher, et al, U.S. Pat. No. 5,206,235 and references cited therein. Intermediate V may be elaborated to a new intermediate (8) as illustrated in Scheme 6 by reductive alkylation with an aldehyde, as previously described in Scheme 1.

SCHEME 5

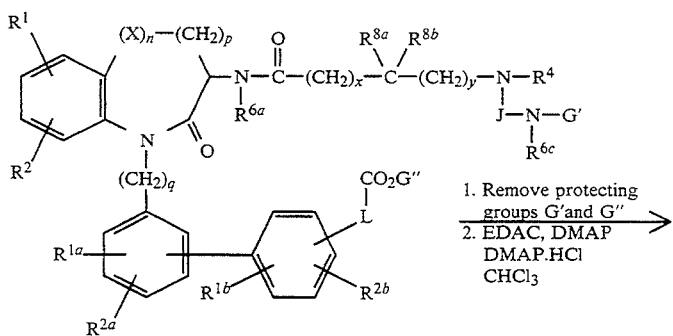

SCHEME 6

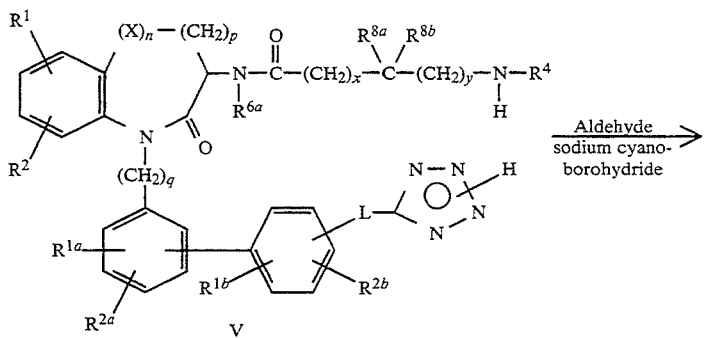

SCHEME 6

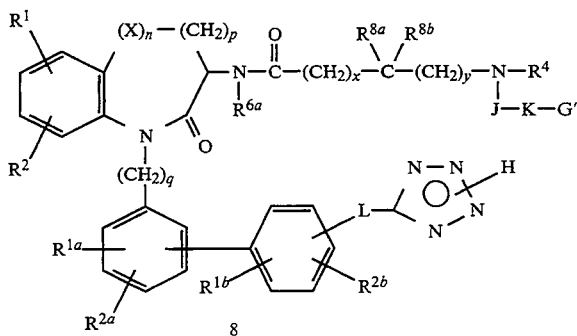

8

As illustrated in Scheme 7, elaboration of the tetrazolyl moiety of 8 is carried out by reaction with alkylating agent 9, wherein Y and E are as previously defined. Reagents such as 9 may be commercially available or are easily prepared from commercially available intermediates by those skilled in the art. Alkylation of intermediate 8 is conveniently carried out by treatment with the alkylating agent 9 in an inert solvent, such as methylene chloride, in the presence of a base, such as triethylamine or diisopropylethylamine. The product 10 is isolated and purified by the aforementioned methods of chromatography.

The subset of compounds of formula I that are described by formula VI is prepared from intermediate 10 as illustrated in Scheme 8. Removal of all protecting groups leads to the formation of an intermediate which is cyclized by the method of T. Jones, et al, *J. Am. Chem. Soc.* 1990, 112, 2998–3017. Thus, treatment of 10 with 2-chloro-N-methylpyridinium iodide and an trialkylamine base followed by removal of any protecting groups gives macrocyclic compounds of formula VI. It should be noted that for removal of acid-sensitive protecting groups from intermediate 10, use of trifluoroacetic acid should be avoided due to competing reaction of the trifluoroacetate anion during the subsequent macrocyclization step.

SCHEME 7

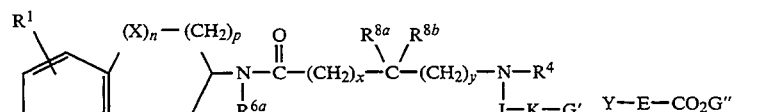

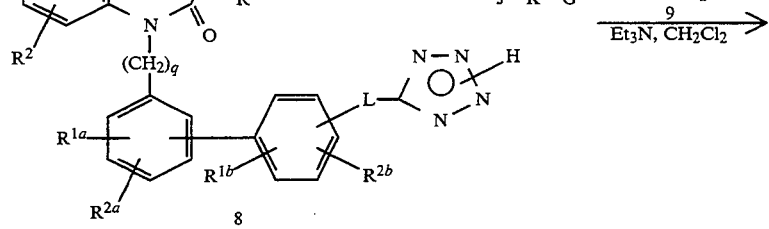

8

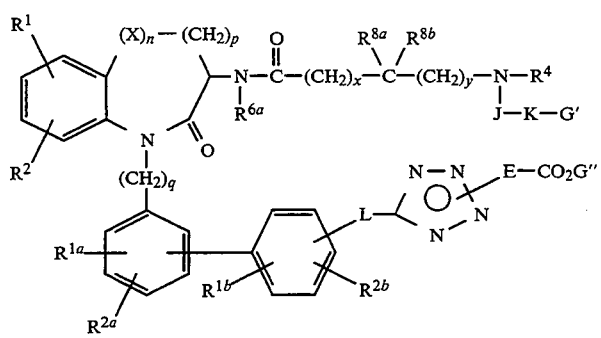

10

SCHEME 8

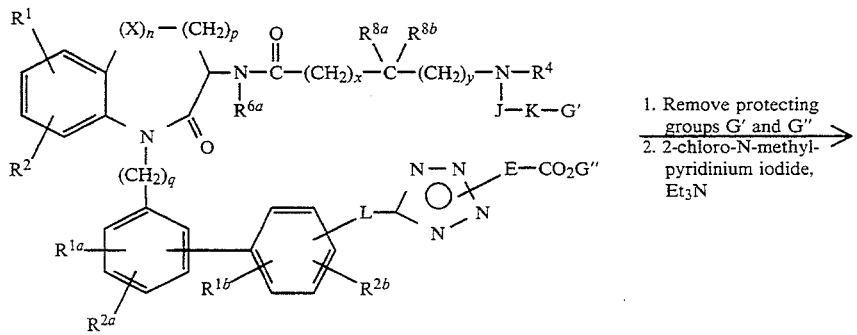

1. Remove protecting groups G' and G"
2. 2-chloro-N-methyl-pyridinium iodide, Et₃N

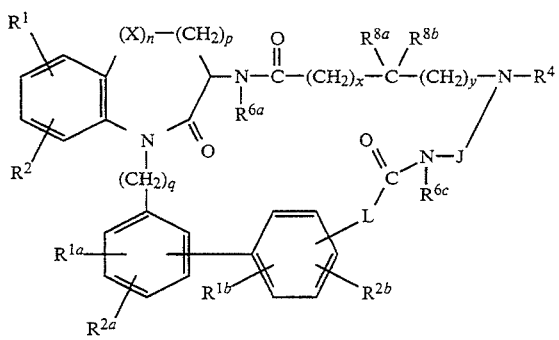

The subset of compounds of formula I described by formula VII is prepared from intermediate 8 as illustrated in Scheme 9. Protection of the tetrazole moiety as the trityl (triphenylmethyl), benzyl or 2-cyanoethyl derivative is carried out by methods known to those skilled in the art or as described in *Protective Groups in Organic Synthesis*. The resulting intermediate can then be selectively deprotected at the functional group K by removal of the protecting group G'. Transformation of the unmasked functional group K to a leaving group such as Y as previously defined can be achieved by several methods known to those skilled in the art. For example, conversion to the O-methanesulfonate ester is carried out by reaction with methanesulfonyl chloride and triethylamine in methylene chloride. Alternatively, treatment with carbon tetrabromide and triphenylphosphine converts hydroxyl groups into the corresponding bromides. The resulting intermediate can then be further elaborated by cleavage of the tetrazole protecting group. The new intermediate thus obtained can be cyclized to compounds of formula VII by treatment of a very dilute solution, in a polar solvent such as methanol, ethanol, methylene chloride, DMF or tetrahydrofuran, with a base such as potassium carbonate or triethylamine in an appropriate co-solvent.

SCHEME 9

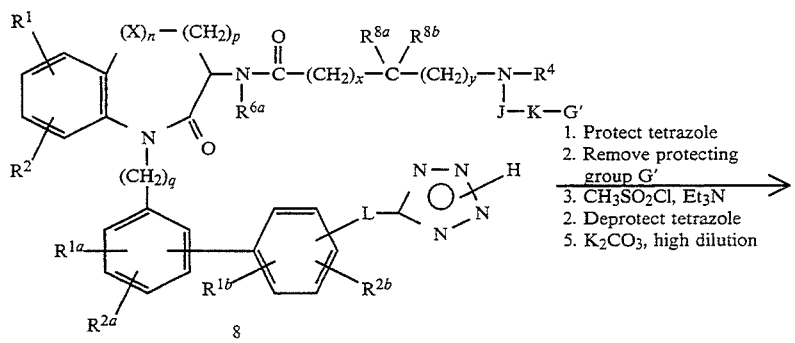

1. Protect tetrazole
2. Remove protecting group G'
3. CH₃SO₂Cl, Et₃N
2. Deprotect tetrazole
5. K₂CO₃, high dilution

SCHEME 9

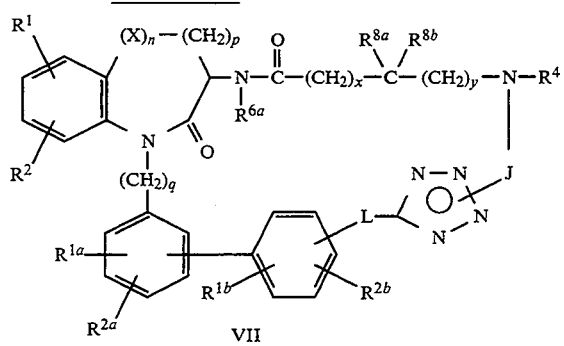

A general preparation of alkylating agent 15 is illustrated in Scheme 10. Protection of the substituted bromophenyl alcohol 11 as the t-butyldimethylsilyl ether is achieved by treatment with t-butyldimethylsilyl chloride and a base such as imidazole or triethylamine. Halogen metal exchange of 11 using an alkyl lithium base such as n-butyllithium followed by treatment with triisopropyl borate and workup with dilute aqueous acid affords the aryl boronic acid 12.

SCHEME 10

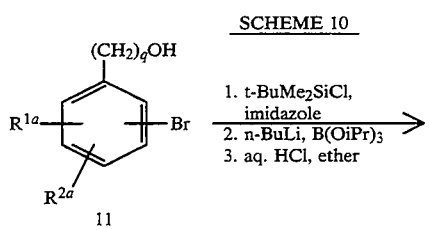

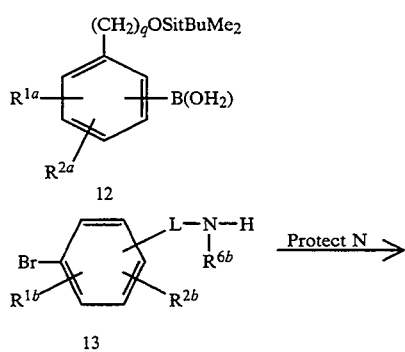

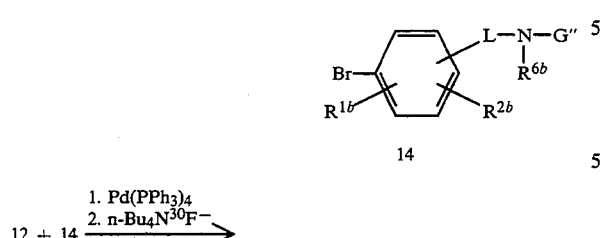

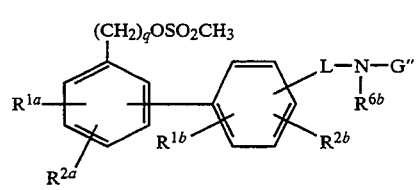

Compounds such as 13 are, in many cases, commercially available or can be prepared from commercially available intermediates by methods known to those skilled in the art. Intermediate 13 is protected with a protecting group G" such as benzyloxycarbonyl or t-butoxycarbonyl by methods known to those skilled in the art or as described in Protective Groups in Organic Synthesis to afford intermediate 14. Reaction of 12 and 14 in the presence of a palladium catalyst, such as tetrakis(triphenylphosphine)palladium (O) at elevated temperatures in a mixed solvent system containing an aqueous base, such as sodium hydroxide, results in coupling to give a biphenyl product. The product thus obtained is selectively deprotected at the oxygen functionality, then derivatived with methanesulfonyl chloride to afford the O-methanesulfonate ester 15.

A useful preparation of the protected benzylamine intermediate 20 is shown in Scheme 11. Metallation of 4-bromobenzyl t-butyldiphenylsilylether 16 with n-butyllithium followed by treatment with triisopropyl borate gives the aryl boronic acid 17. Reaction of 17 with 2-bromo-N-(t-butoxycarbonyl)benzylamine 18 in the presence of tetrakis(triphenylphosphine)palladium(O) and sodium hydroxide in a mixed solvent system at elevated temperature gives the coupled product 19. in good yield. Desilylation and conversion to the O-methanesulfonate 20 is achieved by treatment with tetrabutylammonium fluoride followed by methanesulfonyl chloride.

SCHEME 11

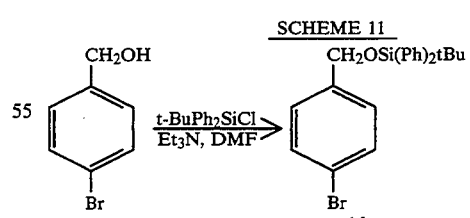

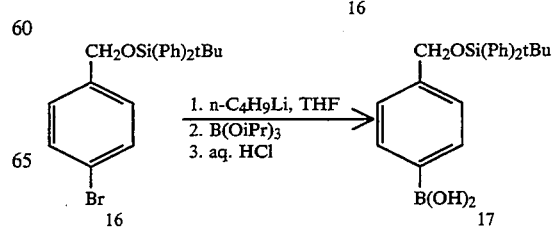

-continued
SCHEME 11

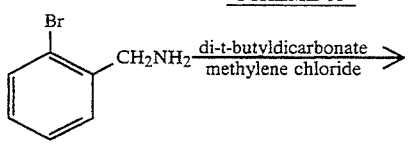

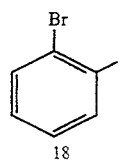
18

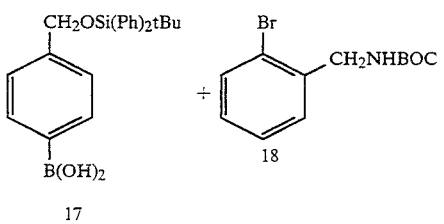

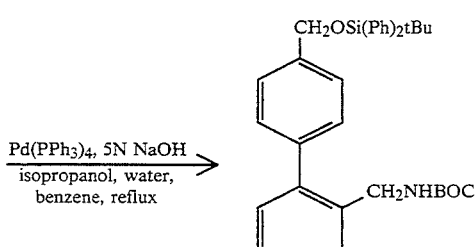
19

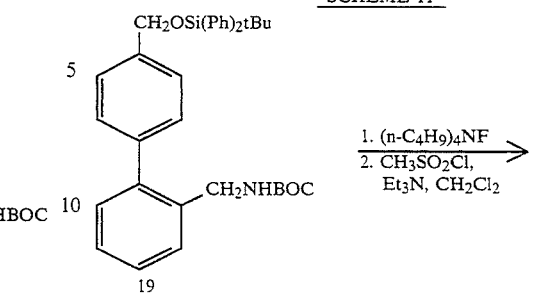
19

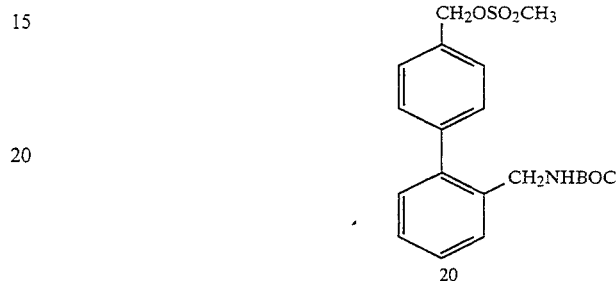
20

Reaction of 15 (or 20) with compounds of formula II is carried out using the alkylation conditions previously described in Scheme 2 and illustrated again in Scheme 12 for the preparation of lactam 21. from intermediate 15.

SCHEME 12

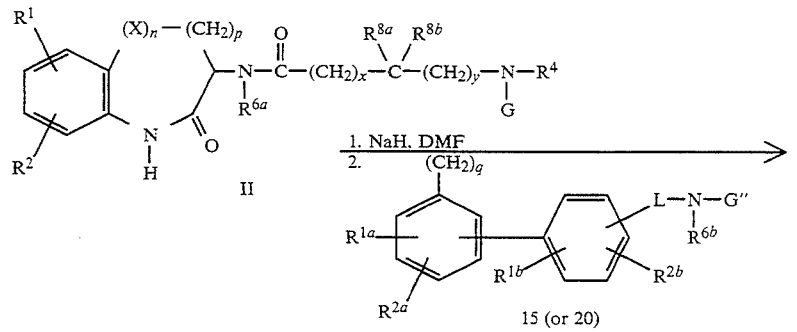

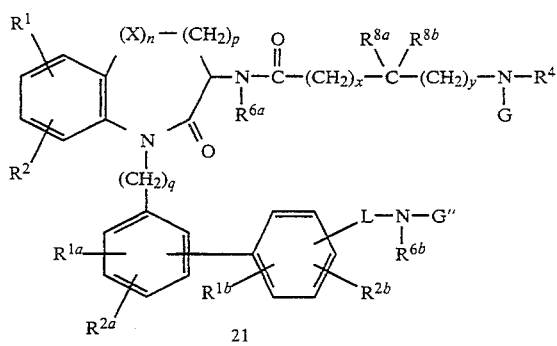

Further elaboration of 21 is carried out as outlined in Scheme 13. Selective removal of protecting group G'' is followed by treatment of the amine thus liberated with the reagent prepared by reaction of the substituted amino acid ester 22 with 1,1'-carbonyldiimidazole (CDI). Removal of protecting group G from the resulting intermediate followed by reductive amination of the unmasked amine as described in Scheme 1 gives the urea product 23.

SCHEME 13

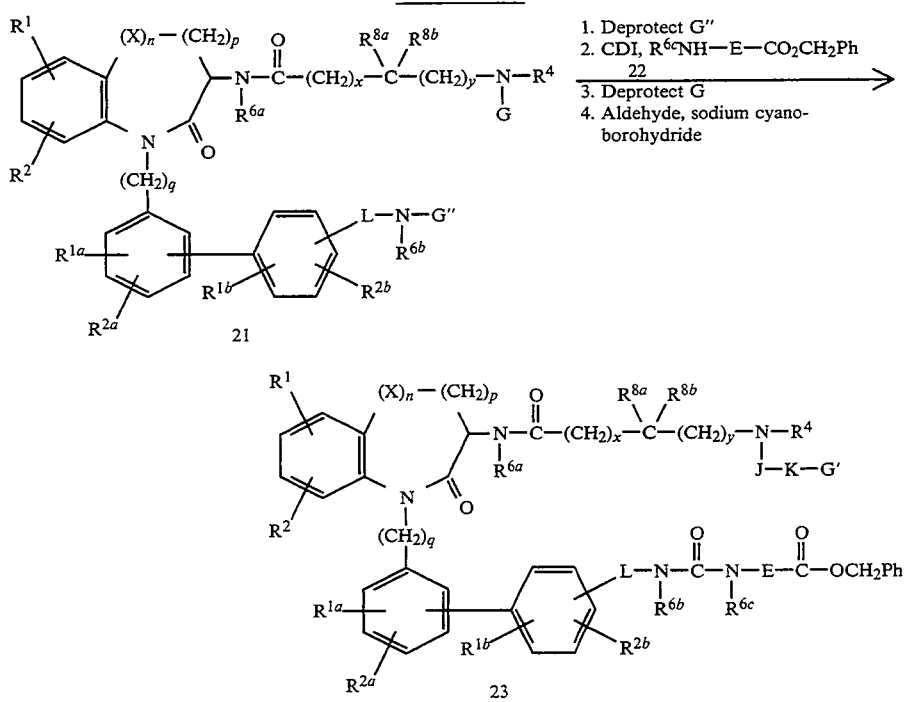

1. Deprotect G"
2. CDI, R$^{6c}$NH—E—CO$_2$CH$_2$Ph
   22
3. Deprotect G
4. Aldehyde, sodium cyanoborohydride The subset of compounds of formula I described by formula VIII is prepared from intermediate 23 as illustrated in Scheme 14. Following removal of the protecting group G' and hydrogenolysis of the benzyl ester, macrocyclization using the previously described conditions of Keck, et al, affords the product VIII.

under the conditions previously described in Scheme 2 gives intermediate 24. Intermediate 24 is further elaborated by removal of the protective group G' and coupling of the unmasked functional group K with the N-protected amino acid derivative 25 in the presence of EDAC and DMAP, as described earlier. Removal of

SCHEME 14

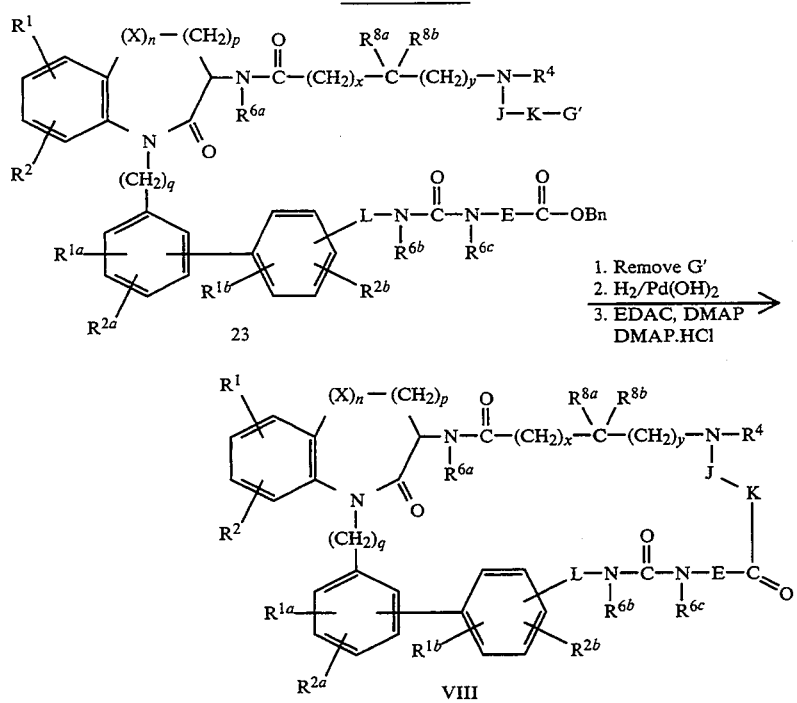

1. Remove G'
2. H$_2$/Pd(OH)$_2$
3. EDAC, DMAP
   DMAP.HCl

Alternatively, compounds of formula VIII are also prepared from intermediate 2 as described in Scheme 15. Reaction of lactam 2 with alkylating agent 15 (or 20)

protecting groups G" and G'", followed by cyclization by treatment with an amine base, such as triethylamine, then slow addition of CDI at room temperature or elevated temperature as needed, in an appropriate solvent such as methylene chloride, chloroform or THF, gives the product VIII.

group, the amino acid derivative thus obtained is cyclized by the previously described conditions of Keck, et al, to afford compounds of formula IX. It will be recognized by one skilled in the art that the reverse of

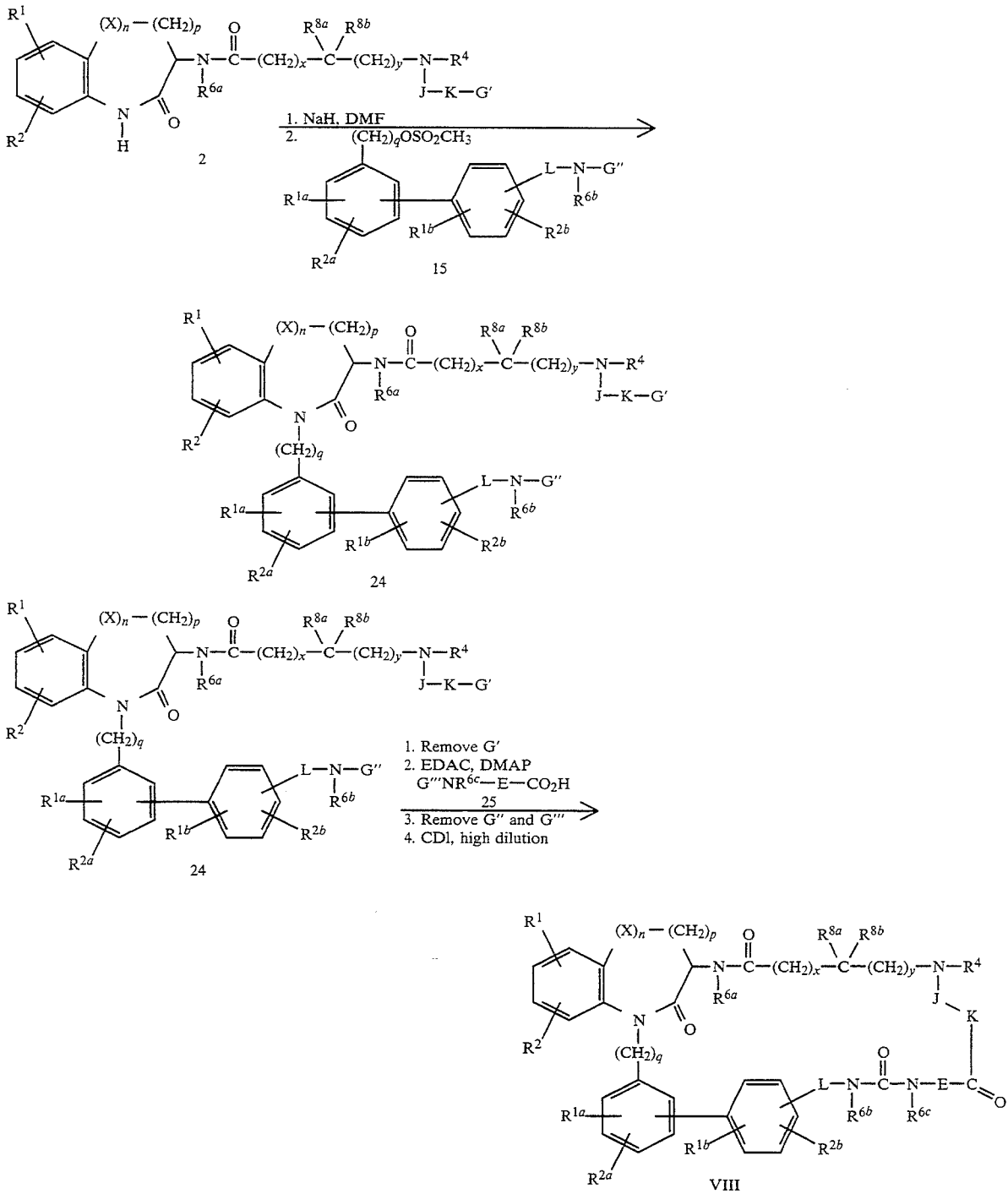

Compounds of formula I that can be described by formula IX are prepared from intermediate 24 as described in Scheme 16. Selective deprotection of the G" group of 24 is followed by reaction with anhydride 26 in the presence of DMAP. Following removal of the G' the above described sequence can also be used to prepare compounds of formula IX. Thus, initial deprotection of group G', reaction with 26, removal of group G", then cyclization as described above will also give compounds of formula IX.

SCHEME 16

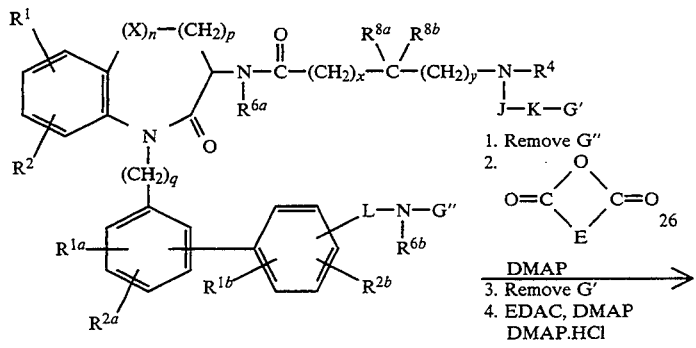

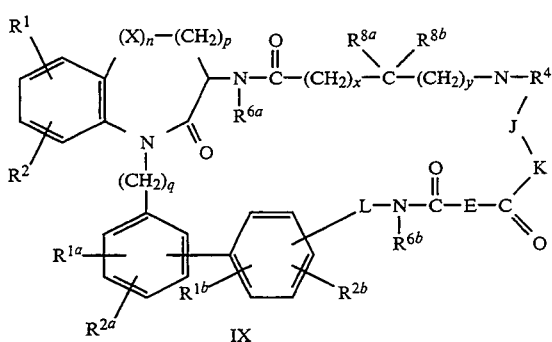

Preparation of alkylating agent 29 is achieved as described in Scheme 17. Intermediate 28 is prepared by protection of the oxygen atom of 27 with an appropriate group G" as described in *Protective Groups in Organic Synthesis*. Coupling of 28 with the arylboronic acid 12 in the presence of a palladium catalyst as described previously, followed by silyl ether removal and reaction with methanesulfonyl chloride gives the O-methanesulfonate ester 29.

SCHEME 17

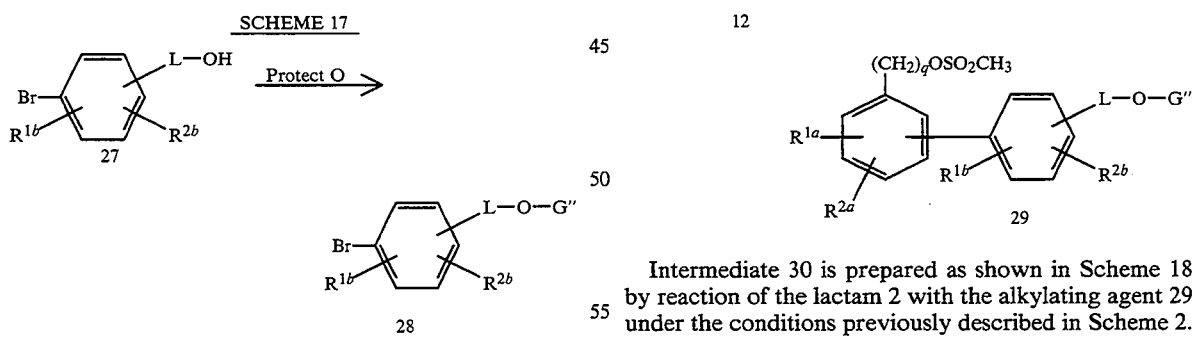

Intermediate 30 is prepared as shown in Scheme 18 by reaction of the lactam 2 with the alkylating agent 29 under the conditions previously described in Scheme 2.

SCHEME 18

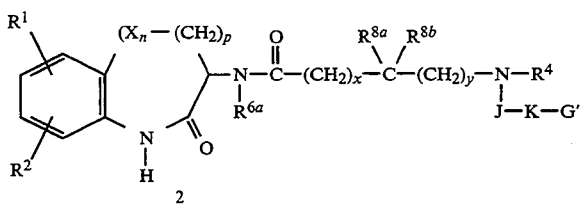

SCHEME 18

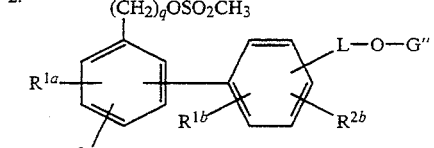

29

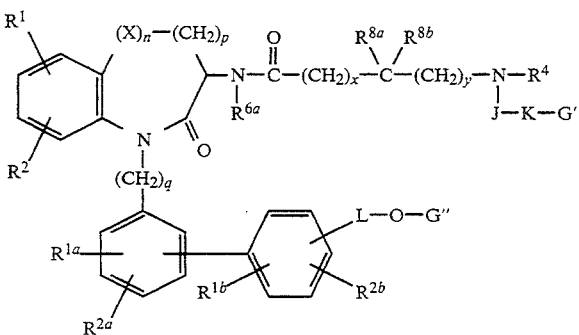

30

The subset of compounds of formula I that can be described by formula X is prepared from intermediate 30 as described in Scheme 19. Selective removal of protective group G' from 29 is followed by coupling at the unmasked functional group with the N-protected amino acid derivative 25 as previously described. Removal of the remaining protecting groups G" and G''', followed by cyclization with CDI as previously described in Scheme 14, results in formation of macrocyclic compounds of formula X.

SCHEME 19

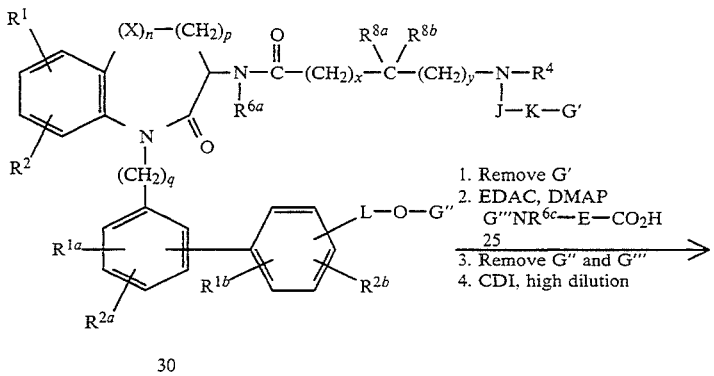

30

1. Remove G'
2. EDAC, DMAP
   G'''NR$^{6c}$—E—CO$_2$H
   25
3. Remove G" and G'''
4. CDI, high dilution

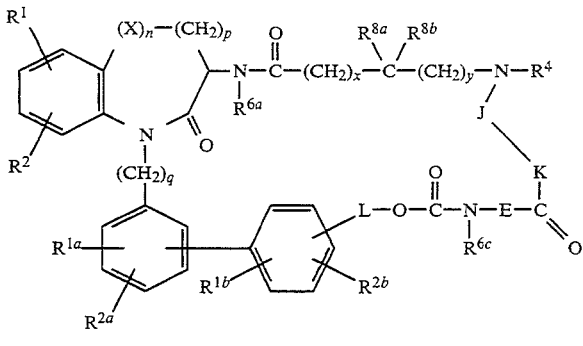

X

Compounds of formula I that can be described by formula XI are prepared from intermediate 24 as described in Scheme 20. Intermediate 24 is selectively deprotected by removal of protective group G' and the resulting intermediate coupled with the O-protected ω-hydroxy acid 31 in the presence of EDAC and DMAP. Removal of protecting groups G" and G''' affords an intermediate hydroxy-amine which is cyclized with CDI (Scheme 14) to give the macrocyclic carbamate compounds of formula XI.

e.g., thyroxine and triiodothyronine. The compounds of Formula I can also be employed to investigate the possible negative or positive feedback effects of some of the pituitary hormones, e.g., growth hormone and endorphin peptides, on the pituitary to modify growth hormone release. Of particular scientific importance is the use of these compounds to elucidate the subcellular mechanisms mediating the release of growth hormone.

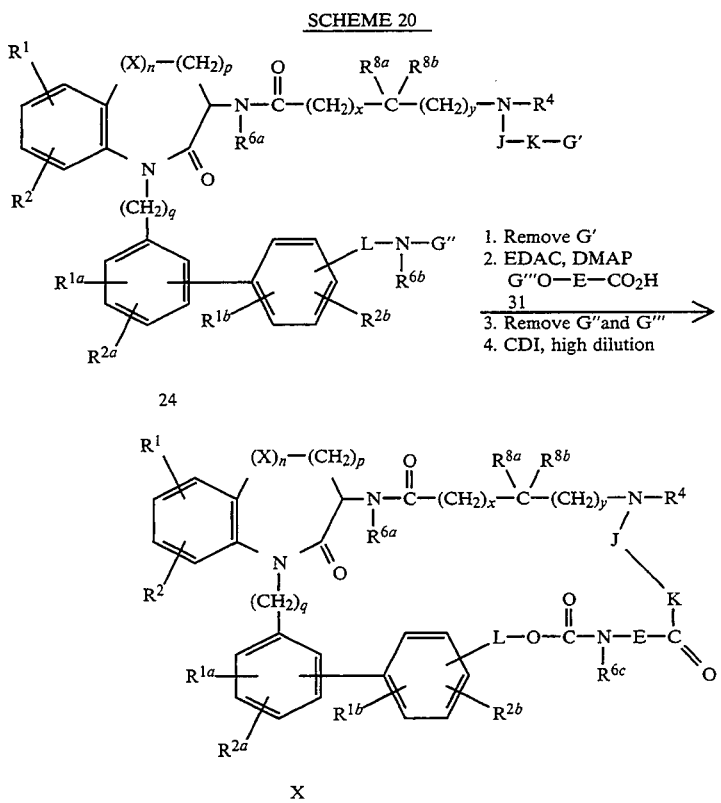

Conversion to the final products of formula I is carried out by simultaneous or sequential removal of all remaining protecting groups from the various intermediates described in the above Schemes. Final products, obtained as hydrochloride or trifluoroacetate salts, are conveniently purified by reverse phase high performance liquid chromatography (HPLC) or by recrystallization.

It is noted that the order of carrying out the foregoing reaction schemes is not significant and it is within the skill of one skilled in the art to vary the order of reactions to facilitate the reaction or to avoid unwanted reaction products.

The growth hormone releasing compounds of Formula I are useful in vitro as unique tools for understanding how growth hormone secretion is regulated-at the pituitary level. This includes use in the evaluation of many factors thought or known to influence growth hormone secretion such as age, sex, nutritional factors, glucose, amino acids, fatty acids, as well as fasting and non-fasting states. In addition, the compounds of this invention can be used in the evaluation of how other hormones modify growth hormone releasing activity. For example, it has already been established that somatostatin inhibits growth hormone release. Other hormones that are important and in need of study as to their effect on growth hormone release include the gonadal hormones, e.g., testosterone, estradiol, and progesterone; the adrenal hormones, e.g., cortisol and other corticoids, epinephrine and norepinephrine; the pancreatic and gastrointestinal hormones, e.g., insulin, glucagon, gastrin, secretin; the vasoactive intestinal peptides, e.g., bombesin; and the thyroid hormones, The compounds of Formula I can be administered to animals, including man, to release growth hormone in vivo. For example, the compounds can be administered to commercially important animals such as swine, cattle, sheep and the like to accelerate and increase their rate and extent of growth, and to increase milk production in such animals. In addition, these compounds can be administered to humans in vivo as a diagnostic tool to directly determine whether the pituitary is capable of releasing growth hormone. For example, the compounds of Formula I can be administered in vivo to children. Serum samples taken before and after such administration can be assayed for growth hormone. Comparison of the amounts of growth hormone in each of these samples would be a means for directly determining the ability of the patient's pituitary to release growth hormone.

Accordingly, the present invention includes within its scope pharmaceutical compositions comprising, as an active ingredient, at least one of the compounds of Formula I in association with a pharmaceutical carder or diluent. Optionally, the active ingredient of the pharmaceutical compositions can comprise a growth promoting agent in addition to at least one of the compounds of Formula I or another composition which exhibits a different activity, e.g., an antibiotic or other pharmaceutically active material.

Growth promoting agents include, but are not limited to, TRH, diethylstilbesterol, theophylline, enkephalins, E series prostaglandins, compounds disclosed in U.S. Pat. No. 3,239,345, e.g., zeranol, and compounds disclosed in U.S. Pat. No. 4,036,979, e.g., sulbenox or peptides disclosed in U.S. Pat. No. 4,411,890.

A still further use of the disclosed novel benzo-fused macrocyclic growth hormone secretagogues is in combination with other growth hormone secretagogues such as GHRP-6, GHRP-1 or GHRP-2 as described in U.S. Pat. No. 4,411,890; and publications WO 89/07110, WO 89/07 111 and WO 93/04081 or B-HT 920 or in combination with growth hormone releasing factor and its analogs or growth hormone and its analogs. A still further use of the disclosed novel benzo-fused macrocyclic growth hormone secretagogues is in combination with $\alpha_2$ adrenergic agonists or $\beta_3$ adrenergic agonists in the treatment of obesity or in combination with parathyroid hormone or bisphosphonates, such as MK-217 (alendronate), in the treatment of osteoporosis. A still further use of the disclosed novel benzo-fused macrocyclic growth hormone secretagogues is in combination with IGF-1 to reverse the catabolic effects of nitrogen wasting as described by Kupfer, et al, *J. Clin. Invest.*, 91, 391 (1993).

As is well known to those skilled in the art, the known and potential uses of growth hormone are varied and multitudinous. Thus, the administration of the compounds of this invention for purposes of stimulating the release of endogenous growth hormone can have the same effects or uses as growth hormone itself. These varied uses of growth hormone may be summarized as follows: stimulating growth hormone release in elderly humans; prevention of catabolic side effects of glucocorticoids; treatment of osteoporosis; stimulation of the immune system; treatment of retardation; acceleration of wound healing; accelerating bone fracture repair; treatment of growth retardation, treating renal failure or insufficiency resulting in growth retardation; treatment of physiological short stature, including growth hormone deficient children; treating short stature associated with chronic illness; treatment of obesity and growth retardation associated with obesity; treating growth retardation associated with Prader-Willi syndrome and Turner's syndrome; accelerating the recovery and reducing hospitalization of burn patients; treatment of intrauterine growth retardation, skeletal dysplasia, hypercortisolism and Cushings syndrome; induction of pulsatile growth hormone release; replacement of growth hormone in stressed patients; treatment of osteochondrodysplasias, Noonans syndrome, schizophrenia, depression, Alzheimer's disease, delayed wound healing, and psychosocial deprivation; treatment of pulmonary dysfunction and ventilator dependency; attenuation of protein catabolic response after a major operation; reducing cachexia and protein loss due to chronic illness such as cancer or AIDS. Treatment of hyperinsulinemia including nesidioblastosis; adjuvant treatment for ovulation induction; to stimulate thymic development and prevent the age-related decline of thymic function; treatment of immunosuppressed patients; improvement in muscle strength, mobility, maintenance of skin thickness, metabolic homeostasis, renal hemeostasis in the frail elderly; stimulation of osteoblasts, bone remodelling, and cartilage growth; stimulation of the immune system in companion animals and treatment of disorders of aging in companion animals; growth promotant in livestock and stimulation of wool growth in sheep.

The compounds of this invention can be administered by oral, parenteral (e.g., intramuscular, intraperitoneal, intravenous or subcutaneous injection or implant), nasal, vaginal, rectal, sublingual, or topical routes of administration and can be formulated in dosage forms appropriate for each mute of administration.

Solid dosage forms for oral administration include capsules, tablets, pills, powders and granules. In such solid dosage forms, the active compound is admixed with at least one inert pharmaceutically acceptable carder such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, s suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as cocoa butter or a suppository wax.

Compositions for nasal or sublingual administration are also prepared with standard excipients well known in the art.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 0.0001 to 100 mg/Kg of body weight daily are administered to patients and animals, e.g., mammals, to obtain effective release of growth hormone.

The following examples are provided for the purpose of further illustration only and are not intended to be limitations on the disclosed invention.

EXAMPLE 1

(12R,19R)-8,9,13,14,15,16,18,19,20,21-Decahydro-12,15,15-trimethyl-6H-28,31-etheno-19,26-methanodibenz[1,t][1,4,8,14,23]oxatetraazacycloheptacosine-5,10,17,34(7H,12H,27H)-tetrone, trifluoroacetate

Step A:
3-Amino-3-methyl-N-[2,3,4,5-tetrahydro-2-oxo-1H-1-benzazepin-3(R)-yl]butanamide, trifluoroacetate To a solution of 150 mg (0.40 mmol) of 3-t-butoxycarbonylamino-3-methyl-N-[2,3,4,5-tetrahydro-2-oxo-1H-1-benzazepin-3(R)-yl]butanamide (prepared by the method of Fisher et. al., U.S. Pat. No. 5,206,235) in 2 mL of methylene chloride at 0° C. was added 2-mL of trifluoroacetic acid and the mixture stirred at room temperature for 1 hour. All volatiles were removed under vacuum to give 130 mg (0.33 mmol, 84%) of the product. $^1$H NMR (200MHz, CD$_3$OD): $\delta$1.33 (s, 3H), 1.37 (s, 3H), 2.12 (m, 1H), 2.3–2.6 (m, 3H), 2.6–3.0 (m, 2H), 4.37 (dd; 8, 12 Hz; 1H), 7.02 (d, 8 Hz, 1H), 7.1–7.3 (m, 3H). FAB-MS: calculated for C$_{15}$H$_{21}$N$_3$O$_2$ 275; found 276 (M+H,100%).

Step B:
3-[2(R)-Benzyloxypropyl]amino-3-methyl-N-[2,3,4,5-tetrahydro-2-oxo-1 H-1-benzazepin-3(R)-yl]butanamide, trifluoroacetate To a solution of 1.0 g (2.57 mmol) of 3-amino-3-methyl-N-[2,3,4,5-tetrahydro-2-oxo-1H-1-benzazepin-3(R)-yl]butanamide, trifluoroacetate (Step A) in 25 mL of dry methanol was added 3.0 g of dry 3 Å powdered molecular sieves followed by a solution of 2.5 g (17 mmol) of (R)-2-benzyloxypropanal (prepared from ethyl D-lactate according to the procedure of Hanessian and Kloss, *Tetrahedron Lett.* 1985 26, 1261–1264) in 5 mL of dry methanol. The pH of the mixture was carefully adjusted to 6 by the addition of trifluoroacetic acid and triethylamine. The reaction was stirred for 2 hours at room temperature at which time 15.4 mL (15.4 mmol) of a 1.0M solution of sodium cyanoborohydride in tetrahydrofuran was added by syringe. The reaction was stirred for 72 hours then filtered through a pad of Celite. To the filtrate was added 5 mL of trifluoroacetic acid (CAUTION! evolution of hydrogen cyanide gas) and the resulting mixture was stirred for three hours. The solvent was removed under vacuum to afford a clear oil which was purified by reverse phase medium pressure liquid chromatography on C-8, eluting with methanol/0.1% aqueous trifluoroacetic acid (60:40), to afford 1.27 g (2.36 mmol, 92%) of the product as a white solid. $^1$H NMR (200 MHz, CD$_3$OD): $\delta$1.31 (d, 6 Hz, 3H), 1.40 (s, 3H), 1.43 (s, 3H), 2.17 (m, 1H), 2.30 (m, 1H), 2.6–3.1 (m, 5H), 3.22 (dd; 3, 12 Hz; 1H), 3.86 (m, 1H), 4.48 (dd; J, 12 Hz; 1H), 4.50 (d, 12 Hz, 1H), 4.70 (d, 12 Hz, 1H), 7.11 (d, 8 Hz, 1H), 7.15–7.45 (m, 8H). FAB-MS: calculated for C$_{25}$H$_{33}$N$_3$O$_3$ 423; found 424 (M+H,100%).

Step C:
3-[2(R)-Benzyloxypropyl]amino-3-methyl-N-[2,3,4,5-tetrahydro-2-oxo-1H-1-benzazepin-3(R)-yl]butanamide To a solution of 2.034 g (3.788 mmol) of the intermediate obtained in Step B in 40 mL of methylene chloride was added 40 mL of water. The mixture was stirred vigorously while sufficient solid potassium carbonate was added to adjust the pH of the aqueous layer to 10–11. Stirring was discontinued and the layers allowed m separate. The organic layer was removed and the aqueous layer extracted twice more with methylene chloride. The combined extracts were dried over potassium carbonate, filtered and solvents removed under vacuum to afford 1.53 g (3.62 mmol, 95%) of the product as a white solid.

Step D: t-Butyl
4'-[[3(R)-[[3-[2(R)-benzyloxypropyl]amino-3-methyl-1-oxobutyl]amino]-2,3,4,5-tetrahydro-2-oxo-1H-1-benzazepin-1-yl]methyl][1,1'-biphenyl]-2-carboxylate To a solution of 600 mg(1.42 mmol) of 3-[2(R)-benzyloxypropyl]amino-3-methyl-N-[2,3,4,5-tetrahydro-2-oxo-1H-1-benzazepin-3(R)-yl]butanamide (Step C) in 10 mL of N,N-dimethylformamide at 0° C. under nitrogen was added 59.5 mg(1.49 mmol) of 60% sodium hydride/oil dispersion. After stirring for 5 minutes, a solution of 450 mg (1.49 mmol) of t-butyl 4-bromomethyl-1,1'-biphenyl-2-carboxylate (prepared according to the procedure of D. J. Carini, et. al. EPO publication 324,377) in 4 mL of dimethylformamide was added dropwise via cannula. The flask originally containing the t-butyl 4-bromomethyl-1,1'-biphenyl-2-carboxylate was rinsed with 2 mL dimethylformamide which was added to the reaction mixture. The mixture was warmed to room temperature and stirred for 1.5 hours. The reaction mixture was diluted with 300 mL of ethyl acetate and washed with 50 mL of water, 50 mL of saturated aqueous sodium bicarbonate and 50 mL of brine, dried over magnesium sulfate, filtered and the solvents removed under vacuum. The residue was purified by column flash chromatography on silica gel eluting with chloroform/10% ammonium hydroxide in methanol (93/7) to give 900 mg (92%) of the product. $^1$H NMR (200MHz, CD$_3$OD): $\delta$1.10 (s, 3H), 1.12 (s, 9H), 1.15 (s, 3H), 1.25 (d, 7 Hz, 3H), 2.15–2.70 (m, 7H), 3.84 (q, 6 Hz, 1H), 4.48–4.68 (m, 3H), 4.82 (d, 15 Hz, 1H), 5.31 (d, 15 Hz, 1H), 7.08–7.48 (m, 16H), 7.7 (dd; 2, 7 Hz; 1H). FAB-MS: calculated for C$_{43}$H$_{51}$N$_3$O$_5$ 689; found 690 (M+H,70%).

Step E:
4'-[[3(R)-[[3-[2(R)-Benzyloxypropyl]amino-3-methyl-1-oxobutyl]amino]-2,3,4,5-tetrahydro-2-oxo-1 H-1-benzazepin-1-yl]methyl][1,1'-biphenyl]-2-carboxylic acid To a solution of 900 mg (1.31 mmol) of the intermediate obtained in Step D in 16 mL of dry methylene chloride was added 10 drops of anisole followed by 10 mL of trifluoroacetic acid. The reaction mixture was stirred for 1.5 hours at room temperature at which time the solvent was removed under vacuum. The resulting oil was dissolved in 10 mL of carbon tetrachloride and the solvent was removed under vacuum. The process was repeated with 10 mL of chloroform followed by 10 mL of methylene chloride to give 959 mg (98% of the product containing minor amount of anisole) as an off-white foam. $^1$H NMR (200 MHz, CDCl$_3$): $\delta$1.20 (d, 7 Hz, 3H), 1.31 (s, 3H), 1.37 (s, 3H), 1.6–1.8 (m, 2H), 2.08–2.43 (m, 4H), 2.55–3.29 (m, 4H), 3.84–4.01 (m, 1H), 4.36–4.59 (m, 3H), 4.69 (d, 15 Hz, 1H), 5.21 (d, 15 Hz, 1H), 6.97–7.61 (m, 16H), 7.95 (d, 8 Hz, 1H), 8.23 (d, 8 Hz, 1H). FAB-MS: calculated for C$_{39}$H$_{43}$N$_3$O$_5$ 633; found 634 (M+H,65%).

Step F: Benzyl 4-aminobutanoate, hydrochloride

To a solution of 1.0 g of 4-aminobutanoic acid in 25 mL of methylene chloride at 0° C. under nitrogen was added 55.5 mL (0.72 mmol) of N,N-dimethylformamide, followed by 1.57 mL (18.0 mmol) of oxalyl chloride. The reaction was warmed to room temperature and after 5 hours the solvent was removed under vacuum and the residue was dissolved in 25 mL of benzyl alcohol. The solution was stirred until it turned clear yellow and then 25 mL of diethyl ether was added. The desired product crystallized and was filtered and triturated with a minimum of ethanol, giving 1.85 g (>100%) of the product as a white crystalline compound. $^1$H NMR (200 MHz, CD$_3$OD): δ1.96 (dt, 8 Hz, 2H), 2.51 (t, 8 Hz, 2H), 2.97 (t, 8 Hz, 2H), 5.12 (s, 2H), 7.27–7.37 (m, 5FAB-MS: calculated for C$_{11}$H$_{15}$NO$_2$193; found 194 (M+H,100%).

Step G:
N-(3-Benzyloxycarbonyl)propyl-4'-[[3(R)-[[3-[2(R)-benzyloxypropyl]amino-3-methyl-1-oxobutyl]amino]-2,3,4,5-tetrahydro-2-oxo-1 H-1-benzazepin-1-yl]methyl][1,1'-biphenyl]-2-carboxamide, hydrochloride To a solution of 274 mg (0.367 mmol) of the intermediate obtained in Step E in 4 mL of methylene chloride was added 0.169 mL (1.21 mmol, 3.3 eq.) of triethylamine and 210 mg of benzotriazol-1-yloxy-tripyrrolidinophosphonium hexafluorophosphate (0.404 mmol, 0.1 eq). The mixture was stirred 10 minutes and 92.6 mg (0.404 mmol, 1.1 eq.) of benzyl 4-aminobutanoate hydrochloride (Step F) was added and the mixture stirred at room temperature for 2 hours. The reaction mixture was added to 150 mL of ethyl acetate and washed with 50 mL of water, 50 mL of saturated aqueous sodium bicarbonate and 50 mL of saturated aqueous sodium chloride. The organic layer was removed, dried over magnesium sulfate, filtered and the filtrate concentrated under vacuum. The residue was purified by flash chromatography on silica gel, eluting with chloroform/10% ammonium hydroxide in methanol (93:7), to give 421 mg (>100%) of a mixture of the product and a by-product, trispyrrolidinophosphoramide, which co-eluted with the product on silica. The mixture was dissolved in 5 mL of 6N hydrochloric acid and the solvent was removed under high vacuum, and this process was repeated with 5 mL more 6N hydrochloric acid to give 312 mg of the hydrochloride salt for use in the next step. $^1$H NMR (200 MHz, CDCl$_3$): δ1.23 (d, 7 Hz, 3H), 1.3–1.72 (m, 11H), 1.8 (m)*, 2.21 (t, 2H), 2.4–2.6 (m, 2H), 2.7–3.0 (m, 4H), 3.13 (m)*, 4.15–4.35 (m, 1H), 4.35–4.55 (m, 1H), 4.54 (d, 12 Hz, 1H), 4.66 (d, 12 Hz, 1H), 4.84 (d, 15 Hz, 1H), 5.03 (s, 2H), 5.09 (d, 15 Hz, 1H), 5.22–5.38 (m, 1H), 7.08–7.43 (m, 23H), 7.59 (dd, 7, 2 Hz; 1H), 7.77 (m, 1H). FAB-MS: calculated for C$_{50}$H$_{56}$N$_4$O$_6$ 808; found 809 (M+H,50%). *Residual trispyrrolidinophosphoramide by-product.

Step H:
N-(3-Carboxypropyl)-4'-[[3(R)-[[3-[2(R)-hydroxypropyl]amino-3-methyl-1-oxobutyl]amino]-2,3,4,5-tetrahydro-2-oxo-1H-1-benzazepin-1-yl]methyl][1,1'-biphenyl]-2-carboxamide, hydrochloride A solution of 312 mg (0.369 mol) of the intermediate obtained in Step G in 5 mL of 1:1 acetonitrile/water was hydrogenated at room temperature and 40 psi over 62.4 mg of 30% palladium on carbon for 24 hours. The reaction mixture was filtered through Celite, rinsed with acetonitrile and the filtrate concentrated to dryness under vacuum. The residue was purified by reverse phase medium pressure liquid chromatography on C-18, eluting with 0.1% trifluoroacetic acid in acetonitrile/0.1% aqueous trifluoroacetic acid (40:60), to give 183 mg (0.246 mmol, 67% combined for Steps G and H) of the product as a white solid. The compound was dissolved in 5mL of 6N hydrochloric acid and the solvent was removed under high vacuum, and this process was repeated with an additional 5 mL of hydrochloric acid to give 126.5 mg of the hydrochloride salt for use in the next step. $^1$H NMR (400 MHz, CDCl$_3$): δ1.22 (d, 8 Hz, 3H), 1.37 (s, 3H), 1.38 (s, 3H), 1.59 (t, 8 Hz, 2H), 1.99–2.2 (m, 3H), 2.38–3.05 (m, 7H), 3.23 (d, 8 Hz, 2H), 4.09–4.2 ( 1H), 4.39–4.5 (m, 1H), 4.81 (d, 16 Hz, 1H), 5.2 (d,16 Hz, 1H), 5.99–6.06 (m, 1H), 7.13–7.8 (m, 13H), 8.0–8.05 (m, 1H), 8.69–8.8 (m, 1H), 8.94–9.1 (m, 1H). FAB-MS: calculated for C$_{36}$H$_{44}$N$_4$O$_6$628; found 629 (M+H, 100%).

Step I:
(12R,19R)-8,9,13,14,15,16,18,19,20,21-Decahydro-12,15,15-trimethyl-6H-28,31-etheno-19,26-methanodibenz[1,t][1,4,8,14,23]oxatetraazacycloheptacosine-5,10,17,34(7H,12H,27H)-tetrone, trifluoroacetate A solution of 69.8 mg of 4-dimethylaminopyridine (0.571 mmol), 60.3 mg of 4-dimethylaminopyridine hydrochloride (0.380 mmol) and 78.4 mg of dicyclohexylcarbodiimide (0.380 mmol) in 6.3 mL of chloroform (ethanol free, purified as described by Perfin, Perfin and Armarego, *Purification of Laboratory Chemicals*, p. 167–168, 2ND Edition, Pergamon Press) was heated to reflux while stirring. In a separate flask, 127 mg (0.19 mmol) of the intermediate obtained in Step H was dissolved in 1.8 mL of chloroform and treated with 46.4 mg (0.380 mmol) of 4-dimethylaminopyridine. This solution was placed in a 5 mL gas-tight syringe and added to the refluxing chloroform solution via syringe pump over 20 hours. The syringe and the flask originally containing the intermediate of Step H and 4-dimethylaminopyridine mixture was rinsed with an additional 1.8 mL of chloroform which was added to the reaction mixture via syringe pump over 2 hours. The reaction mixture was stirred at reflux 2 hours more, cooled to room temperature, then dissolved in 75 mL of ethyl acetate. The resulting solution was washed with 30 mL of water, 30 mL of saturated aqueous sodium bicarbonate and 30 mL of saturated aqueous sodium chloride; the organic layer was dried over magnesium sulfate, filtered and the solvent removed under vacuum. The residue was purified by reverse phase medium pressure liquid chromatography on C-18, eluting with 0.1% trifluoroacetic acid in acetonitrile/0.1% aqueous trifluoroacetic acid (45:55), to give 77.2 mg (56%) of the title compound as a white solid. $^1$H NMR (400 MHz, CD$_3$OD): δ1.3–1.4 (m, 3H), 1.39–1.45 (m, 6H), 1.55–1.68 (m, 1H), 2.19–2.35 (m, 3H), 2.37–2.48 (m, 1H), 2.51 (d,16 Hz, 1H), 2.77–2.84 (m, 2H), 2.9–3.05 (m, 2H), 3.18–3.3 (m, 2H), 3.5–3.6 (m, 1H), 3.99 (d, 16 Hz, 1H), 4.42 (dd; 4, 14 Hz; 1H), 5.09–5.14 (m, 1H), 5.98 (d, 16 Hz, 1H), 6.81 (d, 9 Hz, 1H), 7.14 (t, 9 Hz, 1H), 7.25 (t, 7 Hz, 1H), 7.32 (d, 9 Hz, 2H), 7.4–7.53 (m, 8H), 8.02 (t, 7 Hz, 1H). FAB-MS: calculated for C$_{36}$H$_{42}$N$_4$O$_5$610; found 611 (M+H,100%).

EXAMPLE 2

(10R,17R)-11,12,13,14,16,17,18,19-Octahydro-10,13,13-trimethyl-6H-26,29-etheno-17,24-methanodibenz[1,t][1,4,8,14,23]oxatetraazacyclopentacosine-5,8,15,32(7H,10H,25H)-tetrone, trifluoroacetate

Step A:
N-(3-Benzyloxycarbonyl)methyl-4'-[[3(R)-[[3-[2(R)-benzyloxypropyl]amino-3-methyl-1-oxobutyl]amino]-2,3,4,5-tetrahydro-2-oxo-1H-1-benzazepin-1-yl]methyl][1,1'-biphenyl]-2-carboxamide, hydrochloride Prepared from 4'-[[3(R)-[[3-[2(R)-benzyloxypropyl]amino-3-methyl-1-oxobutyl]amino]-2,3,4,5-tetrahydro-2-oxo-1 H-1-benzazepin-1-yl]methyl][1,1'-biphenyl]-2-carboxylic acid (Example 1, Step E) and glycine benzyl ester hydrochloride by the procedure described in Example 1, Step G. $^1$H NMR (200 MHz, CDCl$_3$): δ1.21 (d, 11 Hz, 3H), 1.2 (s, 3H), 1.22 (s, 3H), 1.72–1.88 (m, 1H), 2.08–2.7 (m, 7H), 3.75–3.92 (m, 3H), 4.48–4.67 (m, 3H), 4.82 (d, 20 Hz, 1H), 5.1 (s, 2H), 5.22 (d, 20 Hz, 1H), 5.72 (t, 1H), 7.0–7.5 (m, 23H), 7.64 (dd; 2, 7 Hz; 1H), 9.1–9.3 (m, 1H). FAB-MS: calculated for C$_{48}$H$_{52}$N$_4$O$_6$780; found 781 (M+H,75%).

Step B:
N-(3-Carboxymethyl)-4'-[[3(R)-[[3-[2(R)-hydroxypropyl]amino-3-methyl-1-oxobutyl]amino]-2,3,4,5-tetrahydro-2 oxo-1 H-1-benzazepin-1-yl]methyl][1,1'-biphenyl]-2-carboxamide, hydrochloride Prepared from the intermediate obtained in Step A by the procedure described in Example 1, Step H. $^1$H NMR (200 MHz, CDCl$_3$): δ1.37 (d, 7 Hz, 3H), 1.41 (s, 3H), 1.49 (s, 3H), 1.88–2.02 (m), 2.2–2.45 (m, 6H), 2.49–2.6 (m, 2H), 2.7–3.2 (m)*, 3.3–3.5 (m)*, 3.79 (dd; 4, 20 Hz; 1H), 3.95 (dd; 4, 20 Hz; 1H), 4.28–4.5 (m, 2H), 4.64 (d, 15 Hz, 1H), 5.16 (d, 15 Hz, 1H), 5.83–5.91 (m, 1H), 7.09 (d, 8 Hz, 1H), 7.21–7.5 (m, 11H), 7.7 (dd, 2, 7 Hz; 1H), 8.65–8.9 (m, 2H), 9.876 (m, 1H). FAB-MS: calculated for C$_{34}$H$_{40}$N$_4$O$_6$ 600; found 601 (M+H,75%).
*Residual trispyrrolidinophosphoramide by-product.

Step C:
(10R,17R)-11,12,13,14,16,17,18,19-Octahydro-10,13,13-trimethyl-6H-26,29-etheno-17,24-methanodibenz[1,t][1,4,8,14,23]oxatetraazacyclopentacosine-5,8,15,32(7H,10H,25H)-tetrone, trifluoroacetate The title compound was prepared from the intermediate obtained in Step B by the procedure described in Example 1, Step I, substituting 1-(3-dimethylaminopropyl)-3-ethylcarbodiimide hydrochloride for dicyclohexylcarbodiimide. $^1$H NMR (400 MHz, CD$_3$OD): δ1.29–1.40 (m, 6H), 1.34 (s, 3H), 2.2–2.31 (m, 1H), 2.32–2.43 (m, 1H), 2.49 (d, 16 Hz, 1H), 2.77 (d, 16 Hz, 1H), 2.78–2.85 (m, 1H), 2.9–3.01 (m, 1H), 3.1–3.2 (m, 1H), 3.29–3.41 (m, 2H), 3.96 (d, 17 Hz, 1H), 4.22 (d, 16 Hz, 1H), 4.39 (dd; 4, 14 Hz; 1H), 4.42, (d, 17 Hz, 1H), 5.42–5.51 (m, 1H), 5.88 (d, 16 Hz, 1H), 7.09 (d, 8 Hz, 1H), 7.16–7.26 (m, 2H), 7.32 (d, 7 Hz, 1H), 7.41 (d, 8 Hz, 1H), 7.52 (d, 8 Hz, 1H), 7.56–7.6 (m, 2H), 7.81 (d, 9 Hz, 2H). FAB-MS: calculated for C$_{34}$H$_{38}$N$_4$O$_5$ 582; found 583 (M+H,100%).

EXAMPLE 3

(11R,18R)-7,8,12,13,14,15,17,18,19,20-Decahydro-11,14,14-trimethyl-27,30-etheno-18,25-methano-25H-dibenz[1,t][1,4,8,14,23]oxatetraazacyclohexacosine-5,9,16,33(6H,11H.,26H)-tetrone, trifluoroacetate

Step A:
N-(3-Benzyloxycarbonyl)ethyl-4'-[[3(R)-[[3-[2(R)-benzyloxypropyl]amino-3-methyl-1-oxobutyl]amino]-2,3,4,5-tetrahydro-2-oxo-1H-1-benzazepin-1-yl]methyl][1,1'-biphenyl]-2-carboxamide, hydrochloride Prepared from the intermediate obtained in Example 1, Step E and benzyl 3-aminopropionate hydrochloride according to the procedure described in Example 1, Step G. $^1$H NMR (200 MHz, CDCl$_3$): δ1.11 (s, 3H), 1.17 (s, 3H), 1.22 (d, 7 Hz, 3H), 1.76–1.9 (m)*, 2.19–2.67 (m, 10H), 2.5–3.1 (m, 1H), 3.1–3.22 (m)*, 3.32 (q, 7 Hz, 2H), 3.49 (q, 7 Hz, 1H), 3.82 (q, 7 Hz, 1H), 4.48–4.66 (m, 3H), 4.79 (d, 20 Hz, 1H), 5.01 (s, 1H), 5.12 (s, 1H), 5.22 (d, 20 Hz, 1H), 5.72 (t, 6 Hz, 1H), 7.04–7.47 (m, 22H), 7.53 (dd; 2, 7 Hz; 1H), 9.1–9.21 (m, 1H).
*Residual trispyrrolidinophosphoramide by-product.

Step. B:
N-(3-Carboxyethyl)-4'-[[3(R)-[[3-[2(R)-hydroxypropyl]amino-3-methyl-1-oxobutyl]amino ]-2,3,4,5-tetrahydro-2-oxo-1H-1-benzazepin-1-yl]methyl][1,1 '-biphenyl]-2-carboxamide, hydrochloride Prepared from the intermediate obtained in Step A by the procedure described in Example 1, Step H. $^1$H NMR (400 MHz, CDCl$_3$): δ1.18–1.32 (m, 3H), 1.3–1.6 (m, 6H), 2.2–3.3 (m, 10H), 3.35–3.55 (m, 2H), 4.18–4.31 (m, 1H), 4.4–4.55 (m, 1H), 4.63 (d, 15 Hz, 1H), 5.34 (d, 15 Hz, 1H), 6.18–6.27 (m, 1H), 6.9–7.42 (m, 12H), 7.48 (t, 7 Hz, 1H), 7.61 (d, 8 Hz, 1H), 8.8–9.0 (m, 1H), 9.3–9.45 (m, 1H). FAB-MS: calculated for C$_{35}$H$_{42}$N$_4$O$_6$ 614; found 615 (M+H,100%).

Step C:
(11R,18R)-7,8,12,13,14,15,17,18,19,20-Decahydro-11,14,14-trimethyl-27,30-etheno-18,25-methano-25H-dibenz[1,t][1,4,8,14,23]oxatetraazacyclohexacosine-5,9,16,33(6H,11H,26H)-tetrone, trifluoroacetate The title compound was prepared from the intermediate obtained in Step B by the procedure described in Example 1, Step I, substituting 1-(3-dimethylaminopropyl)-3-ethylcarbodiimide hydrochloride for dicyclohexylcarbodiimide. $^1$H NMR (400 MHz, CD$_3$OD): δ1.28 (d, 7 Hz, 1H), 1.32–1.41 (m, 6H), 1.42 (s, 3H), 2.1–2.4 (m, 2H), 2.4–2.51 (m, 1H), 2.52–2.68 (m, 2H), 2.7–2.82 (m, 2H), 2.9–3.0 (m, 1H), 3.13–3.22 (m, 1H), 3.25–3.32 (m, 1H), 3.51–3.59 (m, 1H), 4.03 (d, 8 Hz, 1H), 4.33–4.41 (m, 1H), 4.42–4.65 (m, 1H), 5.12–5.21 (m, 1H), 5.99 (d, 8 Hz, 1H), 6.88 (d, 8 Hz, 1H), 7.12–7.27 (m, 3H), 7.27–7.38 (m, 2H), 7.38–7.52 (m, 6H). FAB-MS: calculated for C$_{35}$H$_{40}$N$_4$O$_5$596; found 597 (M+H,75%).

EXAMPLE 4

(13R,20R)-7,8,9,10,14,15,16,17,19,20,21,22-Dodecahydro-13,16,16'-trimethyl-29,32-etheno-20,27-methano-27H-dibenz[1,t][1,4,8,14,23]-oxatetraazacyclooctacosine-5,11,18,35(6H,13H,28H)-tetrone, trifluoroacetate

Step A: Benzyl 5-aminovaleratehydrochloride

Prepared from 5-aminovaleric acid (5-aminopentanoic acid) according to the procedure described in Example 1, Step F. $^1$H NMR (200 MHz, CDCl$_3$):

δ1.6–1.8 (m, 4H), 2.3–2.42 (m, 2H), 2.9–3.1 (m, 2H), 5.4 (s, 2H), 7.2–7.38 (m, 5H), 8.0–8.4 (s, 2H). FAB-MS: calculated for $C_{12}H_{17}NO_2$ 207; found 208 (M+H,100%).

Step B: N-(4-Benzyloxycarbonyl)butyl-4'-[[3(R)-[[3-[2(R)-benzyloxypropyl]amino-3-methyl-1-oxobutyl]amino]-2,3,4,5-tetrahydro-2-oxo-1 H-1-benzazepin-1-yl]methyl][1,1'-biphenyl]-2-carboxamide, hydrochloride Prepared from the intermediate obtained in Example 1, Step E and benzyl 5-aminovalerate hydrochloride (Step A) according to the procedure described in Example 1, Step G. Partial $^1$H NMR * (200 MHz, $CDCl_3$): δ1.10 (s, 3H), 1.17 (s, 3H), 1.23 (d, 7 Hz, 3H), 3.72–3.92 (m, 1H), 4.48–4.69 (m, 3H), 4.84 (d, 15 Hz, 1H), 5.05 (s, 2H), 5.11 (d, 15 Hz, 1H), 5.22 (t, 7 Hz, 1H), 7.07 (m, 23H), 7.61 (dd; 2, 7 Hz; 1H), 9.15 (m, 1H). FAB-MS: calculated for $C_{51}H_{58}N_4O_6$ 822; found 823 (M+H,85%). *Region of spectrum between δ1.30 and δ3.30 very complex and difficult to interpret due to signals from residual trispyrrolidinophosphoramide by-product.

Step C: N-(3-Carboxybutyl)-4'-[[3(R)-[[3-[2(R)-hydroxypropyl]amino-3-methyl-1-oxobutyl]amino ]-2,3,4,5'-tetrahydro-2-oxo-1 H-1-benzazepin-1-yl]methyl][1,1'-biphenyl]-2-carboxamide, hydrochloride Prepared from the intermediate obtained in Step B according to the procedure described in Example 1, Step H. $^1$H NMR (400 MHz, $CD_3OD$): δ1.05–1.45 (m, 12H), 2.09 (m, 1H), 2.17–2.27 (m, 2H), 2.37–2.5 (m, 1H), 2.5–2.7 (m, 3H), 2.7–2.9 (m, 2H), 2.92–3.06 (m, 1H), 3.12–3.3 (m, 2H), 4.07–4.2 (m, 1H), 4.4–4.5 (m, 1H), 4.9 (d, 15 Hz, 1H), 5.14 (d, 15 Hz, 1H), 5.93 (m, 1H), 7.1–7.42, (m, 10H), 7.46 (t, 9 Hz, 1H), 7.54 (d, 9 Hz, 1H), 7.9–8.02 (m, 1H), 8.6–8.85 (m, 1H), 8.85–9.3 (m, 3H).

Step D: (13R,20R)-7,8,9,10,14,15,16,17,19,20,21,22-Dodecahydro-13,16,16-trimethyl-29,32-etheno-20,27-methano-27H-dibenz[1,t][1,4,8,14,23]oxatetraazacyclooctacosine-5,11,18,35(6H,13H,28H)-tetrone, trifluoroacetate The title compound was prepared from the intermediate obtained in Step C by the procedure described in Example 1, Step I, substituting 1-(3-dimethylaminopropyl)-3-ethylcarbodiimide hydrochloride for dicyclohexylcarbodiimide. $^1$H NMR (400 MHz, $CD_3OD$): δ1.33 (d, 8 Hz, 3H), 1.38 (s, 3H), 1.4 (s, 3H), 1.51–1.62 (m, 2H), 2.18–2.42 (m, 4H), 2.52 (d, 17 Hz, 1H), 2.7–2.9 (m, 3H), 3.15–3.32 (m, 6H), 4.39–4.5 (m, 2H), 4.78–5.2 (m, 1H), 5.68 (d, 16 Hz, 1H), 7.06 (d, 8 Hz, 1H), 7.02–7.52 (m, 11H). FAB-MS: calculated for $C_{37}H_{44}N_4O_5$ 624; found 625 (M+H,100%).

EXAMPLE 5

(R)-8,9,10,11,13,14,15,16-Octahydro-10,10-dimethyl-6H-23,26-etheno-14,21-methanodibenzo[1,t][1,4,8,14-]tetraazacyclodocosine-5,12,29(7H,22H)-trione, trifluoroacetate Step A: t-Butyl 4'-[[3(R)-[[3-amino-3-methyl-1-oxobutyl]amino]-2,3,4,5-tetrahydro-2-oxo-1H-1-benzazepin-1-yl]methyl][1,1'-biphenyl]-2-carboxylate acetate To a solution of 400 mg (0.592 mmol) of t-butyl 4'-[[3(R)[[3-benzyloxycarbonylamino-3-methyl-1-oxobutyl]amino]-2,3,4,5-tetrahydro-2-oxo-1H-1-benzazepin-1-yl]methyl][1,1'-biphenyl]-2-carboxylate (prepared according to the procedure of Fisher et al, U.S. Pat. No. 5,206,235) in 10 mL of methanol was added 0.034 mL (0.59 mmol) of acetic acid and 80 mg (20% w/w) palladium hydroxide. The resulting mixture was stirred under a hydrogen atmosphere for 4 hours. Catalyst was removed by filtration through Celite and the solvent removed under vacuum to afford 345 mg (97%) of the product as a white solid. $^1$H NMR (400 MHz, $CD_3OD$): δ1.17 (s, 9H), 1.37 (s, 3H), 1.41 (s, 3H), 1.92 (s, 3H), 2.17 (m, 1H), 2.35 (m, 1H), 2.45–2.75 (m, 4H), 4.41 (dd; 12, 8 Hz; 1H), 4.93 (d, 15 Hz, 1H), 5.37 (d, 16 Hz, 1H), 7.12–7.52 (m, 11H), 7.66 (d, 8 Hz, 1H). FAB-MS: calculated for $C_{33}H_{39}N_3O_4$ 541; found 542 (M+H,100%).

Step B: 2-(t-Butoxycarbonylamino)ethanol

To a solution of 2.8 g (33 mmol) of sodium bicarbonate and 3.65 g (16.7 mmol) of di-t-butyl dicarbonate in 32 mL of a mixture of tetrahydrofuran and water (3:1) was added dropwise via syringe 1.0 mL (17 mmol) of 2-aminoethanol. The reaction mixture was stirred at room temperature for 4 hours then poured into 100 mL of ethyl acetate. The mixture was washed with 100 mL of water, 100 mL of saturated aqueous ammonium chloride and 100 mL of brine. The organic layer was removed, dried over magnesium sulfate, filtered and the solvent removed under vaccum. The residue was purified by flash column chromatography on silica gel, eluting with ethyl acetate/hexanes (65:35) to afford 2.27g (85%) of the product as a clear oil. $^1$H NMR (200 MHz, $CDCl_3$): δ1.52 (s, 9H), 3.34 (t, 4 Hz, 2H), 3.76 (t, 4 Hz, 2H).

Step C: N-(t-Butoxycarbonyl)glycinal

To a solution of 700 mg (4.34 mmol) of 2-(t-butoxycarbonylamino)ethanol in 35 mL of dry methylene chloride was added 4.8 mL (35 mmol) of triethylamine and 4.0 mL of dry dimethylsulfoxide. To the resulting solution was added in portions 2.8 g (17 mmol) of pyridine-sulfur trioxide complex. The resulting brown solution was s stirred at room temperature for 3 hours. The mixture was diluted with 500 mL of ether and transferred to a separatory funnel. The mixture was washed with 1N aqueous hydrochloric acid (2×50 mL), saturated aqueous sodium bicarbonate (100 mL) and brine (100 mL). The organic layer was removed, dried over magnesium sulfate, filtered and the solvent removed under vacuum to afford 550 mg (80%) of the product as an oil. $^1$H NMR (200 MHz, $CDCl_3$): δ1.42 (s, 9H), 4.04 (d, 4 Hz, 2H), 5.18 (s, 1H), 9.62 (s, 1H).

Step D:
4'-[[3(R)-[[3-(2-Aminoethyl)amino-3-methyl-1-oxobutyl]amino]-2,3,4,5-tetrahydro-2-oxo-1H-1-benzazepin-1-yl]methyl][1,1'-biphenyl]-2-carboxylic acid dihydrochloride To a solution of 345 mg (0.573 mmol) of the intermediate obtained in Step A in 10 mL of dry methanol was added 0.088 mL (0.63 mmol) of triethylamine followed by 3.4 g (10% w/w) of powdered 4 Å molecular sieves. To this mixture was added a solution of 540 mg (3.4 mmol) of N-(t-butoxycarbonyl)glycinal in 5 mL of methanol. The pH of the reaction mixture was adjusted to 6.5 by the addition of 4 drops of acetic acid. The resulting mixture was stirred at room temperature for 3 hours at which time 3.4 mL (3.4 mmol) of a 1.0M solution of sodium cyanoborohydride in tetrahydrofuran was added dropwise via syringe. The reaction mixture was stirred at room temperature for 16 hours then filtered through Celite. To the filtrate was added 2 mL of acetic acid (Caution! evolution of hydrogen cyanide gas). After stirring for 3 hours, the solvent was removed under vacuum. The residue was dissolved in 5 mL of methylene chloride. To the resulting solution was added 5 drops of anisole followed by 5 mL of trifluoroacetic acid. The reaction mixture was stirred at room temperature for 4 hours then the solvent was removed under vacuum. The residue was purified by reverse phase medium pressure liquid chromatography on C-8, eluting with methanol/0.1% aqueous trifluoroacetic acid (55:45). The resulting purified trifluoroacetate salt was dissolved in 10 mL of 6N hydrochloric acid and the solvent was removed under vacuum. This was repeated twice more to afford 273 mg (73%) of the product as a white solid. $^1$H NMR (200 MHz, CD$_3$OD): δ1.44 (s, 3H), 1.49 (s, 3H), 2.05–2.45 (m, 2H), 2.52–2.80 (m, 4H), 3.35 (m, 4H), 4.40 (dd; 11, 7 Hz; 1H), 4.99 (d, 15 Hz, 1H), 5.23 (d, 15 Hz, 1H), 7.20–7.60 (m, 11H), 7.80 (d, 8 Hz, 1H). FAB-MS: calculated for C$_{31}$H$_{36}$N$_4$O$_4$528; found 529 (M+H,100%).

Step E:
(R)-8,9,10,11,13,14,15,16-Octahydro-10,10-dimethyl-6H-23,26-etheno-14,21-methanodibenzo[1,t][1,4,8,14]tetraazacyclodocosine-5,12,29(7H,22H)-trione, trifluoroacetate The title compound was prepared from the intermediate obtained in Step D by the procedure described in Example 1, Step I, substituting 1-(3-dimethylaminopropyl)-3-ethylcarbodiimide hydrochloride for dicyclohexylcarbodiimide. $^1$H NMR (200 MHz, CD$_3$OD): δ1.39 (s, 3H), 1.42 (s, 3H), 2.13–2.45 (m, 2H), 2.50 (d, 16 Hz, 1H), 2.64 (d, 16 Hz, 1H), 2.75–3.08 (m, 2H), 3.13 (m, 2H), 3.50 (t, 6 Hz, 2H), 4.39 (dd; 12, 8 Hz; 1H), 4.51 (d, 16 Hz, 1H), 5.60 (d, 16 Hz, 1H), 7.15–7.62 (m, 12H). FAB-MS: calculated for C$_{31}$H$_{34}$N$_4$O$_3$ 510; found 518 (M+Li,100%).

EXAMPLE 6
(R)-9,10,11,12,13,14,16,17,18,19-Decahydro-13,13-dimethyl-7H,25H-26,29-etheno-17,24-methano-6,5-triazino-5H-dibenz[o,w][1,4,7,11,17]pentaazacyclopentacosine-8,15,32-trione, trifluoroacetate

Step A:
3-[[2-(t-Butoxycarbonylamino)ethyl]amino]-3-methyl-N-[2,3,4,5-tetrahydro-2-oxo-1-[[2'-[1-(carboxymethyl)-tetrazol-5-yl][1,1'-biphenyl]-4-yl]methyl]-1 H-1-benzazepin-3(R)-yl]butanamide, t-butyl ester, trifluoroacetate; and
3-[[2-(t-Butoxycarbonylamino)ethyl]amino]-3-methyl-N-[2,3,4,5-tetrahydro-2-oxo-1-[[2'-[2-(carboxymethyl)-tetrazol-5-yl][1,1'-biphenyl]-4-yl]methyl]-1H-1-benzazepin-3(R)-yl]butanamide, t-butyl ester, trifluoroacetate To a solution of 124 mg (0.162 mmol) of 3-[[2-(t-butoxycarbonylamino)ethyl]amino]-3-methyl-N-[2,3,4,5-tetrahydro-2-oxo-1-[[2'-(1H-tetrazol-5-yl)[1,1'-biphenyl]-4-yl]methyl]-1H-1-benzazepin-3(R)-yl]butanamide, trifluoroacetate (prepared by the procedure of Fisher et. al. U.S. Pat. No. 5,206,235) in 1 mL of acetone was added 0.068 mL (0.49 mmol) of triethylamine followed by dropwise addition of 0.040 mL (0.24 mmol) of t-butyl bromoacetate. The reaction mixture was stirred at room temperature for 4 hours then the solvent was removed under vacuum. The residue was dissolved in 70 mL of ethyl acetate, washed with water (25 mL), then saturated aqueous sodium chloride, dried over magnesium sulfate and filtered. The filtrate was evaporated under vacuum and the residue was purified by reverse phase high pressure liquid chromatography on C-18 eluting with methanol/0.1% aqueous trifluoroacetic acid to afford 39 mg (39%) of the N-2 tetrazole isomer and 78 mg (55%) of the N-1 tetrazole isomer. $^1$H NMR of N-2 isomer (200MHz, CDCl$_3$): δ1.37 (s, 15H), 1.44 (s, 9H), 2.18 (m, 1H), 2.3–2.7 (m, 4H), 2.90 (m, 1H), 3.15 (m, 2H), 3.50 (m, 2H), 4.43 (m, 1H), 4.92 (d, 15 Hz, 1H), 5.10 (d, 15 Hz, 1H), 5.20 (s, 2H), 6.20 (s, 1H), 7.10 (s, 3H), 7.14–7.35 (m, 5H), 7.40–7.60 (m, 3H), 7.80 (m, 1H), 8.55 (s, 3H). FAB-MS: calculated for C$_{42}$H$_{54}$N$_8$O$_6$ 766; found 767 (M+H,60%). $^1$H NMR of N-1 isomer (200MHz, CDCl$_3$): 15 1.24 (s, 9H), 1.39 (s, 15H), 2.18 (m, 1H), 2.3–2.75 (m, 4H), 2.90 (m, 1H), 3.17 (m, 2H), 3.52 (m, 2H), 4.10 (d, 16 Hz, 1H), 4.20 (d, 16 Hz, 1H), 4.42 (m, 1H), 4.87 (d, 15 Hz, 1H), 5.19 (d, 15 Hz, 1H), 6.15 (s, 1H), 7.10–7.35 (m, 4H), 7.40–7.70 (m, 4H), 8.50 (m, 2H), 8.95 (s, 2H). FAB-MS: calculated for C$_{42}$H$_{54}$N$_8$O$_6$ 766; found 767 (M+H,60%).

Step B:
3-[(2-Aminoethyl)amino]-3-methyl-N-[2,3,4,5-tetrahydro-2-oxo-1-[[2'-[1-(carboxymethyl)tetrazol-5-yl][1,1'-biphenyl]4-yl]methyl]-1 H-1-benzazepin-3(R)-yl]butanamide, di(trifluoroacetate)

To a solution of 78 mg (0.089 mmol) of the N-1 isomeric product from Step A in. 2 mL of dry methylene chloride was added 10 drops of anisole followed by 2 mL of trifluoroacetic acid. The reaction mixture was stirred at room temperature for 3 hours, then the solvent removed under vacuum. The residue was purified by reverse phase medium pressure liquid chromatography on C-8, eluting with methanol/0.1% aqueous trifluoroacetic acid (50:50), to afford 45 mg (63%) of the product as a white solid. $^1$H NMR (200MHz, CD$_3$OD):

δ1.38 (s, 3H), 1.42 (s, 3H), 2.0–2.7 (m, 6H), 3.32 (m, 4H), 4.37 (dd; 10, 8 Hz; 1H), 4.48 (s, 2H), 4.79(d, 15 Hz, 1H), 5.32 (d, 15 Hz, 1H), 7.05 (d, 8 Hz, 2H), 7.15–7.35 (m, 6H), 7.55 (m,3H), 7.68 (m, 1H). FAB-MS: calculated for $C_{33}H_{38}N_8O_4$ 610; found 612 (M+H,20%).

Step C:
3-[(2-Aminoethyl)amino]-3-methyl-N-[2,3,4,5-tetrahydro-2-oxo-1-[[2'-[1-(carboxymethyl)tetrazol-5-yl][1,1'-biphenyl]4-yl]methyl]-1 H-1-benzazepin-3 (R)-yl]butanamide, dihydrochloride To a solution of 41 mg (0.05 mmol) of the intermediate obtained in Step B in 1 mL methanol was added 2 mL of 6N aqueous hydropchloric acid. The solvent was removed under vacuum to afford 34 mg(100% ) of the product which was used in the next step without further purification.

Step D:
(R)-9,10,11,12,13,14,16,17,18,19-Decahydro-13,13-dimethyl-7H,25H-26,29-etheno-17,24-methano-6,5-triazino-5H-dibenz[o,w][1,4,7,11,17]pentaazacyclopentacosine-8,15,32-trione, trifluoroacetate To a solution of 7.3 mg (0.028 mmol) of 2-chloro-1-methylpyridinium iodide in 18 mL of dry methylene chloride under nitrogen was added 0.006 mL (0.044 mmol) of triethylamine. To the resulting solution was added by syringe over 3 hours a solution of 15 mg (0.022 mmol) of the intermediate obtained in Step C and 0.012 mL (0.088 mmol) of triethylamine in 3 mL of dry methylene chloride. After the addition was completed, the syringe was rinsed with 1 mL of dry methylene chloride and the resulting solution was added by syringe to the reaction mixture. The reaction mixture was stirred at room temperature for 24 hours. The reaction was quenched with 10 mL of water and the layers were separated. The aqueous layer was re-extracted with methylene chloride. The organic extracts were combined, washed with brine (25 mL), dried over sodium sulfate and filtered. The solvent was removed under vacuum and the residue was purified by reverse phase high pressure liquid chromatography on C-18, eluting with methanol/0.1% aqueous trifluoroacetic acid (60:40), to afford 6.9 mg (44%) of the title compound as a white solid. $^1$H NMR (200MHz, CD$_3$OD): δ1.35 (m, 6H), 2.2–2.50 (m, 2H), 2.53–2.75 (m, 2H), 2.76–3.20 (m, 3H), 3.35 (m, 2H), 3.65 (m, 1H), 4.37 (m, 2H), 5.18 (s, 2H), 5.79 (m, 1H), 7.00 (m, 1H), 7.20–7.80 (m, 11H). FAB-MS: calculated for $C_{33}H_{36}N_8O_3$ 592; found 593 (M+H,100%).

EXAMPLE 7

(R)-11,12,13,14,15,16,18,19,20,21-Decahydro-15,15-dimethyl-9H,27H-28,31-etheno-19,26-methano-8,5-nitrilo-5H-dibenzo[q,y][1,2,3,6,9,13,19]heptaazacycloheptacosine-10,17,34-trione, trifluoroacetate Step A:
3-[(2-Aminoethyl)amino]-3-methyl-N-[2,3,4,5-tetrahydro-2-oxo-1-[[2'-[2-(carboxymethyl)tetrazol-5-yl][1,1'-biphenyl]-4-yl]methyl]-1 H-1-benzazepin-3(R)-yl]butanamide, di(trifluoroacetate)

Prepared from the intermediate obtained in Example 6, Step A by the procedure described in Example 6, Step B. $^1$H NMR (200MHz, CD$_3$OD): 1.38 (s, 3H), 1.42 (s, 3H), 2.0–2.6 (m, 6H), 3.32 (m, 4H), 4.39 (dd; 7, 11 Hz; 1H), 4.92 (d, 16 Hz, 1H), 5.22 (d, 16 Hz, 1H), 5.42 (s, 2H), 7.04 (d, 8 Hz, 2H), 7.17 (d, 8 Hz, 2H), 7.2–7.4 (m, 4H), 7.41–7.62 (m, 3H), 7.75 (m, 1H). FAB-MS: calculated for $C_{33}H_{38}N_8O_4$ 610; found 611 (M+H,100%).

Step B:
(R)-11,12,13,14,15,16,18,19,20,21-Decahydro-15,15-dimethyl-9H,27H-28,31-etheno-19,26-methano-8,5-nitrilo-5H-dibenzo[q,y][1,2,3,6,9,13,19]heptaazacycloheptacosine-10,17,34-trione, trifluoroacetate To a solution of 8 mg (0.031 mmol) of 2-chloro-1-methylpyridinium iodide in 20 mL of dry methylene chloride under nitrogen was added 0.007 mL (0.048 mmol) of triethylamine. To the resulting solution was added by syringe over 3 hours a solution of 19 mg (0.022 mmol) of the intermediate obtained in Step A and 0.017 mL (0.088mmol) of triethylamine in 4 mL of dry methylene chloride. After the addition was completed the syringe was rinsed with 1 mL of dry methylene chloride and the resulting solution was added by syringe to the reaction mixture. The reaction mixture was stirred at room temperature for 24 hours. The reaction was quenched with 10 mL of water and the layers were separated. The aqueous layer was extracted with methylene chloride. The organic extracts were combined, washed with brine (25 mL), dried over sodium sulfate and filtered. The solvent was removed under vacuum and the residue was purified by chromatography on silica gel eluting with ethyl acetate to afford 6 mg of a white solid.

The solid was dissolved in 1 mL of methanol and to this solution was added 0.5 mL of saturated aqueous sodium carbonate. The mixture was stirred at room temperature for 3 days. The solvent was removed under vacuum and the residue was dissolved in saturated aqueous sodium chloride. The aqueous solution was extracted with ethyl acetate (3×30 mL) and the organic layers were combined, dried over magnesium sulfate and filtered. The solvent was removed under vacuum and the residue was purified by reverse phase high pressure liquid chromatography on C-18, eluting with methanol/0.1% aqueous trifluoroacetic acid (60:40), to afford 4.1 mg (26%) of the title compound as a white solid. $^1$H NMR (200MHz, CD$_3$OD): δ1.32 (s, 3H), 1.40 (s, 3H), 2.15–2.42 (m, 2H), 2.65 (m, 2H), 2.70–3.00 (m, 2H), 3.20 (m, 2H), 3.45 (m, 1H), 3.70 (m, 1H), 4.10 (d, 16 Hz, 1H), 4.39 (m, 1H), 5.50 (s, 2H), 5.90 (d, 16 Hz, 1H), 6.90 (m, 1H), 7.10–7.40 (m, 8H), 7.52 (m, 1H), 7.65 (m, 2H). FAB-MS: calculated for $C_{33}H_{36}N_8O_3$ 592; found 593 (M+H,100%).

EXAMPLE 8

(13R,20R)-5,9,10,14,15,16,17,19,20,21,22,28-Dodecahydro-13,16,16-trimethyl-29,32-etheno-20,27-methano-27H-dibenz[1,t][1,4,8,14,23,25]oxapentaazacyclooctacosine-7,11,18,35(6H,8H,13H)-tetrone, trifluoroacetate Step A: 4-Bromobenzyl-t-butyldiphenylsilyl ether To a solution of 28.2 g (0.150 mol) of 4-bromobenzylalcohol in 470 mL of dry dimethylformamide under nitrogen atmosphere was added 31.4 mL (0.225 mol) of triethylamine. The reaction mixture was cooled to 0° C. and 43 mL (0.17 mol) of t-butylchlorodiphenylsilane was added dropwise by addition funnel. The reaction mixture was stirred at ambient temperature overnight then poured into a separatory funnel containing 1L of diethyl ether and 500 mL of water. To this mixture was added 125 mL of 2N aqueous hydrochloric acid. The layers were separated and the aqueous layer was extracted with diethyl ether (2×350 mL). The organic extracts were combined, washed with water (2×250 mL) and dried over magnesium sulfate. The solids were removed by filtration and the solvent removed under vacuum to give an oil which crystallized on standing. The flask containing the crude product was placed in the freezer overnight then triturated with a minimal amount of methanol and filtered. The solid was air dried for several hours then dried under vacuum overnight to afford 59.5 g (93%) of product as an off-white solid (mp 44°–47° C.). $^1$H NMR (200 MHz, CDCl$_3$): δ1.15 (s, 9H), 4.76 (s, 2H), 7.25 (d, 8 Hz, 2H), 7.45 (m, 8H), 7.75 (m, 4H). FAB-MS: calculated for C$_{23}$H$_{25}$BrOSi 424; found 425 (M+H,7%).

Step B: 4-(t-Butyldiphenylsiloxymethyl)phenylboronic acid

To a solution of 20 g (47 mmol) of 4-bromobenzyl-t-butyldiphenyl silyl ether (Step A) in 200 mL of dry tetrahydrofuran under a nitrogen atmosphere at −78° C. was added dropwise by syringe 19.74 mL (49.35 mmol) of a 2.5M solution of n-butyl lithium in hexanes over twenty minutes. The resulting mixture was stirred for thirty minutes, then 11.6 mL (50.3 mmol) of triisopropyl borate was added by syringe. The reaction mixture was stirred at −78° C. for thirty minutes then slowly warmed to room temperature and stirred for an additional two hours. The reaction mixture was then quenched by the addition of 750 mL of water containing 100 mL of concentrated hydrochloric acid and 500 mL of diethyl ether. The mixture was stirred for one hour and then the organic layer was separated. The aqueous layer was extracted with diethyl ether (2×400 mL). The combined ether extracts were washed with saturated aqueous sodium chloride (4×100 mL), dried over magnesium sulfate and filtered. The solvent was removed under vacuum to give an oil which was crystallized by dissolving in hexanes and evaporation of the solvent under vacuum to afford 15.6 g (85%) of product as a white solid (mp 171°–174° C.). $^1$H NMR (200 MHz, CDCl$_3$): δ1.11 (s, 9H), 4.86 (s, 2H), 7.40 (m, 6H), 7.58 (d, 8 Hz, 2H), 7.70 (m, 4H), 8.22 (d, 8 Hz, 2H). FAB-MS: calculated for C$_{23}$H$_{27}$BrO$_3$Si 390; found 372 (M-H$_2$O).

Step C: N-(t-Butoxycarbonyl)-2-bromobenzylamine

To a slurry of 8.88 g (39.9 mmol) of 2-bromobenzylamine hydrochloride in 100 mL of dry methylene chloride under a nitrogen atmosphere was added by syringe 12.24 mL (87.80 mmol) of triethylamine. The resulting solution was stirred at 0° C. for five minutes then treated with 9.6 g (44 mmol) of di-t-butyldicarbonate. The reaction was stirred at room temperature for two hours then diluted with 350 mL of methylene chloride. The solution was washed with water (2×150 mL), saturated aqueous ammonium chloride (150 mL), saturated aqueous sodium bicarbonate (4×150 mL) and saturated aqueous sodium chloride (150 mL), dried over sodium sulfate and filtered. The solvent was removed under vacuum to give an oil which was crystallized by dissolving in hot hexanes, filtering and cooling the solution. The product was filtered and dried under vacuum to afford 8.66 g (90%) of the product as a white solid (mp 51°–53° C.). $^1$H NMR (200 MHz, CDCl$_3$): δ1.41 (s, 9H), 4.37 (d, 5 Hz, 2H), 5.00 (s, 1H), 7.10 (m, 1H), 7.25 (m, 1H), 7.35 (m, 1H), 7.40 (d, 6 Hz, 1H). FAB-MS: calculated for C$_{12}$H$_{16}$BrNO$_2$ 285; found 286 (M+H), Step D: 2'-[(t-Butoxycarbonylamino)methyl]-4-[(t-butyldiphenylsiloxy)methyl]-1,1,1'-biphenyl To a solution of 3.2 g (8.2 mmol) of 4-(t-butyldiphenylsilyoxymethyl)phenylboronic acid (Step B) in 64 mL of benzene was added 2.2 mL of water, 6.4 mL of 5N aqueous sodium hydroxide, and 8.3 mL of isopropanol. To this mixture was added 180 mg (0.16 mmol) of tetrakis(triphenylphosphine) palladium and 2.20 g (7.81 mmol) of N-(t-butoxycarbonyl)-2-bromobenzylamine (Step C). The resulting mixture was heated under nitrogen at reflux for 2 hours then cooled to room temperature. The reaction mixture was diluted with 100 mL of water, transferred to a separatory funnel and extracted with ether (3×150 mL). The combined ether extracts were washed with saturated aqueous sodium bicarbonate (100 mL) and saturated aqueous sodium chloride (100 mL), dried over magnesium sulfate and filtered. The solvent was removed under vacuum to give a crude product which was purified by column chromatography on silica gel eluting with hexanes/ethyl acetate (9:1) to afford 4.31 g (100%) of the product as a clear oil. $^1$H NMR (200 MHz, CDCl$_3$): δ1.11 (s, 9H), 1.41 (s, 9H), 4.27 (d, 6 Hz, 2H), 4.45 (m, 1H), 4.81 (s, 2H), 7.20–7.49 (m, 14H), 8.72 (m, 4H). FAB-MS: calculated for C$_{35}$H$_{41}$NO$_3$Si 551; found 552 (M+H).

Step E: 2'-[(t-Butoxycarbonylamino)methyl]-1,1'-biphenyl-4-methanol

To a solution of 3.85 g (7.00 mmol) of 2'-[(t-butoxycarbonylamino)methyl]-4-[(t-butyldiphenylsiloxy)methyl]-1,1'-biphenyl (Step D) in 25 mL of dry tetrahydrofuran under a nitrogen atmosphere was added by syringe 10.5 mL (0.530 mmol) of a 1.0M solution of tetra-n-butylammonium fluoride in tetrahydrofuran. The reaction mixture was stirred for two hours then diluted with 700 mL of diethyl ether. The mixture was washed with water (3×150 mL), saturated aqueous sodium bicarbonate (50 mL), saturated aqueous sodium chloride (50 mL), then dried over magnesium sulfate and filtered. The solvent was removed under vacuum to give an oil which was purified by column chromatography on silica gel eluting with hexanes/ethyl acetate (55:45) to afford 2.02 g (92%) of the product as a white solid (mp 89°–93° C.). $^1$H NMR (200 MHz, CDCl$_3$): δ1.40 (s, 9H), 2.50 (s, 2H), 4.20 (s, 2H), 4.70 (s, 2H), 7.18–7.45 (m, 8H). FAB-MS: calculated for C$_{19}$H$_{23}$NO$_3$ 313; found 314 (M+H).

Step F: 2'-[(t-Butoxycarbonylamino)methyl]-1,1'-biphenyl-4-methanol, methanesulfonate ester To solution of 53 mg (0.17 mmol) of 2'-[(t-butoxycarbonylamino)methyl]-1,1'-biphenyl-4-methanol (Step E) in 1 mL of dry methylene chloride under nitrogen atmosphere at 0° C. was added by syringe 0.035 mL (0.25 mmol) of triethylamine followed by 0.016 mL (0.20 mmol) of methanesulfonyl chloride. The reaction mixture was stirred for 2 hours at 0° C. then diluted with 75 mL of methylene chloride, washed with water, saturated aqueous sodium bicarbonate, saturated aqueous sodium chloride, dried over sodium sulfate and filtered. The solvent was removed under vacuum to give 61 mg (97%) of the product as a white solid which was used in the next step without further purification. $^1$H NMR (200 MHz, CDCl$_3$): δ1.38 (s, 9H), 2.95 (s, 3H), 4.20 (d, 5 Hz, 2H), 4.65 (s, 1H), 5.25 (s, 2H), 7.18–7.50 (m, 8H). FAB- MS: calculated for $C_{20}H_{25}NO_5S$ 391; found 392 (M+H).

Step G:
3-Benzyloxycarbonylamino-3-methyl-N-[2,3,4,5-tetrahydro-2-oxo-1-[[2'-[(t-butoxycarbonylamino)methyl][1,1'-biphenyl]-4-yl]methyl]-1H-benzazepin-3(R)-yl]butanamide Prepared from 3-benzyloxycarbonylamino-3-methyl-N[2,3,4,5-tetrahydro-2-oxo-1H-1-benzazepin-3(R )-yl]-butanamide (prepared by the method of Fisher et. al., U.S. Pat. No. 5,206,235) and 2'-(t-butoxycarbonylamino)methyl]-1,1'-biphenyl-4-methanol, methanesulfonate ester (Step F) according to the procedure described in Example 1, Step D. $^1H$ NMR (200 MHz, $CDCl_3$): δ1.38 (m, 15H), 2.36–2.58 (m, 6H), 4.19 (d, 6 Hz, 2H), 4.40–4.62 (m, 2H), 4.87 (d, 15 Hz, 1H), 5.01 (d, 12 Hz, 1H) 5.07 (d, 12 Hz, 1H), 5.20 (d, 15 Hz, 1H), 5.63 (s, 1H), 6.67 (d, 8 Hz, 1H), 7.10–7.42 (m, 17H). FAB-MS: calculated for $C_{42}H_{48}N_4O_6$ 704; found 705 (M+H).

Step H:
3-Benzyloxycarbonylamino-3-methyl-N-[2,3,4,5-tetrahydro-2-oxo-1-[[2'-aminomethyl[1,1'-biphenyl]-4-yl]methyl]-1H-benzazepin-3(R )-yl]butanamide, trifluoroacetate Prepared from the intermediate obtained in Step G by the procedure described in Example 1, Step E. $^1H$ NMR (200MHz, $CD_3OD$): δ1.40 (s, 6H), 2.04 (m, 1H), 2.31 (m, 2H), 2.55 (d, 12 Hz, 1H), 2.62 (m, 2H), 4.08 (s, 2H), 4.42 (dd; 12, 8 Hz; 1H), 5.01 (d, 12 Hz, 1H), 5.07 (d, 14 Hz, 1H), 5.10 (d, 12 Hz, 1H), 5.15 (d, 14 Hz, 1H), 7.20–7.60 (m, 17H). FAB-MS: calculated for $C_{37}H_{40}N_4O_4$ 604; found 605 (M+H).

Step I:
3-Benzyloxycarbonylamino-3-methyl-N-[2,3,4,5-tetrahydro-2-oxo-1-[[[[[2-(t-butoxycarbonyl)ethyl]amino]-carbonyl]amino]methyl][1,1'-biphenyl]-4-yl]methyl]-1H-benzazepin-3(R)-yl]butanamide To a slurry of 500 mg (0.696 mmol) of the intermediate obtained in Step H in 1.0 mL of dry methylene chloride under a nitrogen atmosphere was added 0.194 mL (1.39 mmol) of triethylamine. The mixture was stirred at room temperature for 30 minutes (Mixture A). In a separate flask was placed 182 mg (1.39 mmol) of β-alanine t-butyl ester hydrochloride in 4.0 mL of dry methylene chloride under a nitrogen atmosphere. To this slurry was added 0.194 mL (1.39 mmol) of triethylamine. After 15 minutes, 162 mg (1.39 mmol) of 1,1'-carbonyldiimidazole was added. The resulting mixture was stirred at room temperature for 30 minutes, then the previously prepared amine solution (Mixture A) was added via cannula to the reaction mixture. After stirring for 24 hours at room temperature, the reaction mixture was diluted with 200 mL of ethyl acetate, washed with 75 mL of water, 75 mL of saturated sodium bicarbonate and 75 mL of brine. The organic layer was removed, dried over magnesium sulfate, filtered and the solvent removed under vacuum. The resulting material was purified by flash column chromatography on silica gel, eluting with ethyl acetate/hexanes (80:20), to afford 452 mg (84%) of the product as a white foam. $^1H$ NMR (200 MHz, $CDCl_3$): δ1.30–1.50 (m, 15H), 2.30–2.60 (m, 8H), 3.32 (q, 6 Hz, 2H), 4.20 (d, 6 Hz, 2H), 4.46 (m, 1H), 4.87 (d, 15 Hz, 1H), 5.01 (d, 12 Hz, 1H) 5.07 (d, 12 Hz, 1H), 5.20 (d, 15 Hz, 1H), 5.71 (s, 1H), 6.7 (d, 8 Hz, 1H), 7.1–7.45 (m, 19H). FAB-MS: calculated for $C_{45}H_{53}N_5O_7$ 775; found 776 (M+H).

Step J:
3-Amino-3-methyl-N-[2,3,4,5-tetrahydro-2-oxo-1-[[[[[2-(t-butoxycarbonyl)ethyl]amino]carbonyl]amino]methyl][1,1'-biphenyl]-4-yl]methyl]-1H-benzazepin-3(R)-yl]butanamide.

To a solution of 452 mg (0.582 mmol) of the intermediate obtained in Step I in 5 mL of methanol was added 40 mg (20% w/w) of palladium hydroxide. The resulting mixture was stirred under a hydrogen atmosphere for 24 hours. The catalyst was removed by filtration through Celite and the solvent removed under vacuum to afford 373 mg(100% ) of the product as a white solid. $^1H$ NMR (400 MHz, $CD_3OD$): δ1.32 (s, 3H), 1.33 (s, 3H), 1.42 (s, 9H), 2.28–2.70 (m, 8H), 3.29–3.32 (m, 2H), 4.12 (d, 16 Hz, 1H), 4.17 (d, 16 Hz, 1H), 4.41 (dd; 12, 8 Hz; 1H), 5.00 (d, 15 Hz, 1H), 5.22 (d, 15 Hz, 1H), 7.10–7.42 (m, 12 H). FAB-MS: calculated for $C_{37}H_{47}N_5O_5$ 641; found 642 (M+H).

Step K:
3-[2(R)-[(Tetrahydropyran-2-yl)oxy]propyl]amino-3-methyl-N-[2,3,4,5-tetrahydro-2-oxo-1-[[[[[2-(t-butoxycarbonyl)ethyl]amino]carbonyl]amino]methyl][1,1-biphenyl]-4-yl]methyl]-1H-benzazepin-3(R)-yl]butanamide To a solution of 418 mg (0.65 mmol) of the intermediate obtained in Step J in 12 mL of dry methanol was added 2.0 g of dry powdered 3 Å molecular sieves followed by a solution of 466 mg (2.95 mmol) of (R)-2-[(tetrahydropyran-2-yl)oxy]propanal (prepared from methyl (R)-lactate according to the procedure of Okay, *Synthetic Comm.* 1989, 19, 2125–2132) in 3 mL of dry methanol. The pH of the mixture was carefully adjusted to 6 by the addition of acetic acid. The reaction was stirred for 2 hours at room temperature at which time 2.0 mL (2.0 mmol) of a 1.0M solution of sodium cyanoborohydride in tetrahydrofuran was added by syringe. The reaction was stirred for 16 hours then filtered through a pad of Celite. The filtrate was dissolved in 300 mL of ethyl acetate. The resulting solution was washed with 100 mL of water and 100 mL of saturated aqueous sodium chloride; the organic layer was removed and dried over magnesium sulfate, filtered and the solvent removed under vacuum. The residue was purified by column flash chromatography on silica gel eluting with chloroform/10% ammonium hydroxide in methanol (95/5–91/9)) to give 335 mg (66%) of the product. $^1H$ NMR (200 MHz, $CDCl_3$): δ1.10–1.30 (m, 9H), 1.4 (s, 9H), 1.45–60 (m, 3H), 1.70–2.05 (m, 7H), 2.18–2.26 (m, 1H), 2.37 (t, 7 Hz, 2H), 2.41–2.70 (m, 4H), 3.32 (q, 6 Hz, 2H), 3.40–3.54 (m, 1H), 3.78–4.04 (m, 3H), 4.21 (d, 6 Hz, 2H), 4.48–4.78 (m, 2H), 4.82–4.92 (m, 1H), 4.93–5.18 (m, 2H), 7.1–7.5 (m, 12H), 9.05–9.35 (m, 1H). FAB-MS: calculated for $C_{45}H_{61}N_5O_7$ 783; found 784 (M+H).

Step L:
3-[2(R)-Hydroxypropyl]amino-3-methyl-N-[2,3,4,5-tetrahydro-2-oxo-1-[[[[[2-(t-butoxycarbonyl)ethyl]amino]-carbonyl]amino]methyl][1,1'-biphenyl]-4-yl]methyl]-1H-benzazepin-3(R)-yl]butanamide, hydrochloride To a solution of 335 mg (0.43 mmol) of the intermediate obtained in Step K in 10 mL of dry methylene chloride was added 6 drops of anisole followed by 5 mL of trifluoroacetic acid. The reaction mixture was stirred for 3 hours at room temperature at which time the solvent was removed under vacuum. The residue was purified by reverse phase medium pressure liquid chromatography on C-18, eluting with 0.1% trifluoroacetic acid in acetonitrile/0.1% aqueous trifluoroacetic acid (40:60), to give 238 mg (0.359 mmol, 83%) of the product as a white solid. The compound was dissolved in 5 mL of 6N hydrochloric acid and the solvent was removed under high vacuum, and this process was repeated with 5 mL more hydrochloric acid to give 126.5 mg of the hydrochloride salt for use in the next step. $^1$H NMR (400 MHz, CD$_3$OD): δ1.20 (d, 7 Hz, 3H), 1.37 (s, 3H), 1.39 (s, 3H), 2.10–2.20 (m, 1H), 2.28–2.38 (m, 1H), 2.47 (t, 8 Hz, 2H), 2.55–2.71 (m, 4H), 2.80 (dd; 14, 10 Hz; 1H), 3.09 (dd; 12, 4 Hz; 1H), 3.35 (t, 8 Hz, 2H), 3.90–3.98 (m, 1H), 4.18 (d, 4 Hz, 2H), 4.39 (dd; 12, 8 Hz; 1H), 5.05 (d, 15 Hz, 1H), 5.16 (d, 15 Hz, 1H), 7.40 (m, 12H). FAB-MS: calculated for C$_{36}$H$_{45}$N$_5$O$_6$643; found 644 (M+H).

Step M:
(13R,20R)-5,9,10,14,15,16,17,19,20,21,22,28-Dodecahydro-13,16,16-trimethyl-29,32-etheno-20,27-methano-27H-dibenz
[1,t][1,4,8,14,23,25]oxapentaazacyclooctacosine-7,11,18,35(6H,8H,13H)-tetrone, trifluoroacetate.

The title compound was prepared from the intermediate obtained in Step L by the procedure described in Example 1, Step I, substituting 1-(3-dimethylaminopropyl)-3-ethylcarbodiimide hydrochloride for dicyclohexylcarbodiimide. $^1$H NMR (400 MHz, CD$_3$OD): 1.22 (d, 4 Hz, 3H), 1.26 (s, 3H), 1.28 (s, 3H), 2.15–2.40 (m, 4H), 2.60 (d, 16 Hz, 1H), 2.68 (d, 16 Hz, 1H), 2.77–2.82 (m, 1H), 2.85–3.01 (m, 1H), 3.12–3.30 (m, 4H), 4.03 (d, 15 Hz, 1H), 4.22 (d, 17 Hz, 1H), 4.57 (d, 17 Hz, 1H), 4.59 (dd; 8, 4 Hz; 1H), 4.95–5.10 (m, 1H), 5.82 (d, 15 Hz, 1H), 7.10–7.50 (m, 12 H). FAB-MS: calculated for C$_{36}$H$_{43}$N$_5$O$_5$625; found 626 (M+H).

EXAMPLE 9

(12R,19R)-5,8,9,13,14,15,16,18,19,20,21,27-Dodecahydro-12,15,15-trimethyl-6H-28,31-etheno-19,26-methanodibenz[1,t][1,4,8,14,23,25]oxapentaazacycloheptacosine-7,10,17,34(7H,12H)-tetrone, trifluoroacetate Step A:
3-[2(R)-Benzyloxypropyl]amino-3-methyl-N-[2,3,4,5-tetrahydro-2-oxo-1-[[2'-[(t-butoxycarbonylamino)methyl][1,1'-biphenyl]-4-yl]methyl]-1H-benzazepin-3(R)-yl]butanamide Prepared from 3-[2(R)-benzyloxypropyl]amino-3-methyl-N-[2,3,4,5-tetrahydro-2-oxo-1H-1-benzazepin-3(R )-yl]butanamide (Example 1, Step C) and 2'-[(t-butoxycarbonylamino)methyl]-1,1'-biphenyl-4-methanol, methanesulfonate ester (Example 8, Step F) by the procedure described in Example 1, Step D. $^1$H NMR (200 MHz, CDCl$_3$): δ1.14 (s, 3H), 1.19 (s, 3H), 1.23 (d, 6 Hz, 3H), 1.39 (s, 9H), 1.86 (m, 1H), 2.20–2.75 (m, 7H), 3.88 (m, 1H), 4.18 (d, 6 Hz, 2H), 4.48–4.66 (m, 3H), 4.92 (d, 15 Hz, 1H), 5.13 (d, 15 Hz, 1H), 7.10–7.43 (m, 20 H). CI-MS: calculated for C$_{44}$H$_{54}$N$_4$O$_5$ 718; found 719 (M+H).

Step B:
3-[2(R)-Hydroxypropyl]amino-3-methyl-N-[2,3,4,5-tetrahydro-2-oxo-1-[[2'-[(t-butoxycarbonylamino)methyl][1,1'-biphenyl]-4-yl]methyl]-1H-benzazepin-3(R)-yl]butanamide To a solution of 525 mg (0.695 mmol) of the intermediate prepared in Step A in 6 mL of methanol was added 0.350 mL (0.700 mmol) of 2N hydrochloric acid and 100 mg (20% w/w) of 30% palladium on carbon. The resulting mixture was shaken under a hydrogen atmosphere at 40 psi for 24 hours. The catalyst was removed by filtration through Celite and the solvent removed under vacuum. The residue was purified by column flash chromatography on silica gel, eluting with chloroform/10% ammonium hydroxide in methanol (95/5), to give 415 mg (95%) of the product as a white solid. $^1$H NMR (400 MHz, CD$_3$OD): δ1.12–1.21 (m, 9H), 1.42 (s, 9H), 2.04–2.13 (m, 1H), 2.22–2.41 (m, 3H), 2.49–2.62 (m, 4H), 3.80–3.88 (m, 1H), 4.09 (s, 2H), 4.42 (dd; 12, 4 Hz; 1H), 4.97 (d, 15 Hz, 1H), 5.30 (d, 15 Hz, 1H), 7.11–7.42 (m, 12 H). FAB-MS: calculated for C$_{37}$H$_{48}$N$_4$O$_5$ 628; found 629 (M+H).

Step C:
3-[2(R)-[[(t-Butoxycarbonylamino)methyl]carbonyloxy]propyl]amino-3-methyl-N-[2,3,4,5-tetrahydro-2-oxo-1-[[2-[(t-butoxycarbonylamino)methyl][1,1'-biphenyl]-4-yl]methyl]-1H-benzazepin-3(R)-yl]butanamide To a solution of 200 mg of the intermediate obtained in Step B in 3 mL of dry deutero-chloroform was added by syringe 0.098 mL (0.70 mmol) of triethylamine followed by 61.3 mg (0.35 mmol) of N-t-butoxycarbonyl glycine, 184 mg (0.96 mmol) of 1-(3-dimethylaminopropyl)-3-ethylcarbodiimide hydrochloride and 117 mg (0.96 mmol) of 4-dimethylaminopyridine. The resulting mixture was heated to reflux and stirred for 45 min then cooled to room temperature. The solvent was removed under vacuum and the residue was dissolved in 200 mL of ethyl acetate. The resulting solution was washed with 75 mL of water and 75 mL of saturated aqueous sodium chloride; the organic layer was removed and dried over magnesium sulfate, filtered and the solvent removed under vacuum. The residue was purified by column flash chromatography on silica gel, eluting with chloroform/10% ammonium hydroxide in methanol (95/5), to give 200 mg (80%) of the product. $^1$H NMR (200 MHz, CDCl$_3$): δ1.11 (s, 3H) 1.14 (s, 3H), 1.28 (d, 7 Hz, 3H), 1.38 (s, 18H), 1.82–2.02 (m, 1H), 2.21 (s, 2H), 2.40–2.55 (m, 3H), 2.69 (d, 6 Hz, 2H), 3.89 (d, 6 Hz, 2H), 4.19 (d, 6 Hz, 2H), 4.50–4.67 (m, 1H), 4.94 (d, 15 Hz, 1H), 5.02–5.20 (m, 3H), 7.1–7.43 (m, 15H). FAB-MS: calculated for C$_{44}$H$_{59}$N$_5$O$_8$ 785; found 786 (M+H).

Step D: 3-[2(R )-[(Aminomethyl)carbonyloxy]propyl]amino-3-methyl-N-[2,3,4,5-tetrahydro-2-oxo-1-[[2'-aminomethyl-[1,1'-biphenyl]-4-yl]methyl]-1H-benzazepin-3(R)-yl]butanamide, tris(trifluoroacetate)

Prepared from the intermediate obtained in Step C by the procedure described in Example 1, Step E. $^1$H NMR (200 MHz, CD$_3$OD): δ1.20–1.50 (m, 9H), 2.00–2.20 (m, 1H), 2.20–2.48 (m, 1H), 2.49–2.72 (m, 4H), 3.10–3.40 (m, 2H), 3.84 (s, 2H), 4.01 (s, 2H), 4.38 (dd; 12, 8 Hz; 1H), 4.85 (d, 15 Hz, 1H), 5.15–5.30 (m, 1H), 5.45 (d, 15 Hz, 1H), 7.18–7.68 (m, 12H). FAB-MS: calculated for C$_{34}$H$_{43}$N$_5$O$_4$ 585; found 586 (M+H).

Step E:
(12R,19R)-5,8,9,13,14,15,16,18,19,20,21,27-Dodecahydro-12,15,15-trimethyl-6H-28,31-etheno-19,26-methanodibenz[1,t][1,4,8,14,23,25]oxapentaazacycloheptacosine-7,10,17,34(7H,12H)-tetrone, trifluoroacetate To a solution of 20 mg (0.022 mmol) of the intermediate obtained in Step D in 2 mL of dry tetrahydrofuran at room temperature was added by syringe 0.031 mL (0.220 mmol) of triethylamine. The resulting mixture was stirred for 15 min. In a separate flask, 4 mg (0.025 mmol) of 1,1'-carbonyldiimidazole was dissolved in 1 mL of tetrahydrofuran. This solution was placed in a 5 mL gas-tight syringe and added to the original stirred reaction mixture at room temperature by syringe pump over 20 hours. The reaction mixture was stirred at room temperature 4 hours more, and the solvent was removed under vacuum. The residue was dissolved in 75 mL of ethyl acetate, and the resulting solution was washed with 30 mL of water and 30 mL of saturated aqueous sodium chloride. The organic layer was dried over sodium sulfate, filtered and the solvent removed under vacuum. The residue was purified by reverse phase medium pressure liquid chromatography on C-18, eluting with acetonitrile/0.1% aqueous trifluoroacetic acid (40:60), to give 7 mg (44%) of the title compound as a white solid. $^1$H NMR (400 MHz, CD$_3$OD): $\delta$1.31 (d, 6 Hz, 3H), 1.36 (s, 3H), 1.44 (s, 3H), 2.20–2.40 (m, 2H), 2.58 (d, 16 Hz, 1H), 2.70 (d, 15 Hz, 1H), 2.70–2.80 (m, 1H), 2.80–2.92 (m, 1H), 3.17 (t, 12 Hz, 1H), 3.30–3.37 (m, 1H), 3.67 (d, 18 Hz, 1H), 3.97 (d, 18 Hz, 1H), 4.12 (d, 15 Hz, 1H), 4.28 (d, 15 Hz, 1H), 4.32 (d, 16 Hz, 1H), 4.52 (dd; 8, 4 Hz; 1H), 5.16–5.25 (m, 1H), 5.72 (d, 16 Hz, 1H), 7.10–7.49 (m, 12H). FAB-MS: calculated for C$_{35}$H$_{41}$N$_5$O$_5$611; found 612 (M+H).

EXAMPLE 10

(12R,19S)-8,9,13,14,15,16,19,20-Octahydro-12,15,15-trimethyl-6H,12H-28,31-etheno-19,26-methanodibenz[1,t][1,11,4,8,14,23]oxathiatetra-azacycloheptacosine-5,10,17,34(7H,18H,27H)-tetrone

Step A:
3-Amino-3-methyl-N-[3,4-dihydro-4-oxo-1,5-benzothiazepin-3(S)-yl]butanamide, trifluoroacetate This intermediate is prepared from 3-t-butoxycarbonylamino-3-methyl-N-[3,4-dihydro-4-oxo-1,5-benzothiazepin-3(S)-yl]butanamide (prepared by the method of Fisher et. al., U.S. Pat. No. 5,206,235) according to the procedure described in Example 1, Step A.

Step B: 3-[2(R)-Benzyloxypropyl]amino-3-methyl-N-[3,4-dihydro-4-oxo-1,5-benzothiazepin-3(S)-yl]butanamide, trifluoroacetate This intermediate is prepared from the intermediate obtained in Step A according to the procedure described in Example 1, Step B.

Step C:
3-[2(R)-Benzyloxypropyl]amino-3-methyl-N-[3,4-dihydro-4-oxo-1,5-benzothiazepin-3(S)-yl]butanamide This intermediate is prepared from the intermediate obtained in Step B by the procedure described in Example 1, Step C.

Step D: t-Butyl 4'-[[3(S)-[[3-[2(R)-benzyloxypropyl]amino-3-methyl-1-oxobutyl]amino]-3,4-dihydro-4-oxo-1,5-benzothiazepin-5-yl]methyl][1,1'-biphenyl]-2-carboxylate This intermediate is prepared from the intermediate obtained in Step C and t-butyl 4-bromomethyl-1,1'-biphenyl-2-carboxylate (prepared according to the procedure of D. J. Carini, et. al. EPO publication 324,377) by the procedure described in Example 1, Step D.

Step E:
4'-[[3(S)-[[3-[2(R)-benzyloxypropyl]amino-3-methyl-1-oxobutyl]amino]-3,4-dihydro-4-oxo-1,5-benzothiazepin-5-yl]methyl][1,1'-biphenyl]-2-carboxylic acid This intermediate is prepared from the intermediate obtained in Step D according to the procedure described in Example 1, Step E.

Step F:
N-(3-Benzyloxycarbonyl)propyl-4'-[[3(S)-[[3-[2(R)-benzyloxypropyl]amino-3-methyl-1-oxobutyl]amino]-3,4-dihydro-4-oxo-1,5-benzothiazepin-5-yl]methyl][1,1'-biphenyl]-2-carboxamide, hydrochloride This intermediate is prepared from the intermediate obtained in Step E and benzyl 4-aminobutanoate hydrochloride (Example 1, Step F) according to the procedure described in Example 1, Step G.

Step G:
N-(3-Carboxypropyl)-4'-[[3(S)-[[3-[2(R)-hydroxypropyl]amino-3-methyl-1-oxobutyl]amino]-3,4-dihydro-4-oxo-1,5-benzothiazepin-5-yl]methyl][1,1'-biphenyl]-2-carboxamide, hydrochloride This intermediate is prepared from the intermediate obtained in Step F according to the procedure described in Example 1, Step H.

Step H:
(12R,19S)-8,9,13,14,15,16,19,20-Octahydro-12,15,15-trimethyl-6H,12H-28,31-etheno-19,26-methanodibenz[1,t][1,11,4,8,14,23]oxathiatetraazacycloheptacosine-5,10,17,34(7H,18H,27H)-tetrone, trifluoroacetate The title compound is prepared from the intermediate obtained in Step G according to the procedure described in Example 1, Step I.

EXAMPLE 11

(12R,19S)-5,8,9,13,14,15,16,19,20,27-Decahydro-12,15,15-trimethyl-6H,12H-28,31-etheno-19,26-methanodibenz[1,t][1,11,4,8,14,23,25]-oxathiapentaazacycloheptacosine-7,10,17,34(7H,18H)-tetrone

Step A:
3-[2(R)-Benzyloxypropyl]amino-3-methyl-N-[3,4-dihydro-4-oxo-5-[[2'-[(t-butoxycarbonylamino)methyl]][1,1'-biphenyl]-4-yl]methyl]-1,5-benzothiazepin-3(S)-yl]butanamide This intermediate is prepared from 3-[2(R)-benzyloxypropyl]amino-3-methyl-N-[3,4-dihydro-4-oxo-1,5-benzothiazepin-3 (S)yl]butanamide (Example 10, Step C) and 2'-[(t-butoxycarbonylamino)methyl]-1,1'-biphenyl-4-methanol, methanesulfonate ester (Example 8, Step F) by the procedure described in Example 1, Step D.

Step B:
3-[2(R)-Hydroxypropyl]amino-3-methyl-N-[3,4-dihydro-4-oxo-5-[[2'-[(t-butoxycarbonylamino)methyl][1,1'-biphenyl]-4-yl]methyl]-1,5-benzothiazepin-3(S)-yl]butanamide This intermediate is prepared from the intermediate obtained in Step A, according to the procedure described in Example 9, Step B.

Step C:
3-[2(R)-[[(t-Butoxycarbonylamino)methyl]carbonyloxy]propyl]amino-3-methyl-N-[3,4-dihydro-4-oxo-5-[[2'-[(t-butoxycarbonylamino)methyl][1,1'-biphenyl]-4-yl]methyl]-1,5-benzothiazepin-3(S)-yl]butanamide This intermediate is prepared from the intermediate obtained in Step B and N-t-butoxycarbonyl glycine according to the procedure described in Example 9, Step C.

Step D: 3-[2(R)-[(Aminomethyl)carbonyloxy]propyl]amino-3-methyl-N-[3,4-dihydro-4-oxo-5-[[2'-aminomethyl[1,1'-biphenyl]-4-yl]methyl]-1,5-benzothiazepin-3(S)-yl]butanamide, tris(trifluoroacetate)

This intermediate is prepared from the intermediate obtained in Step C by the procedure described in Example 1, Step E.

Step E:
(12R,19S)-5,8,9,13,14,15,16,19,20,27-Decahydro-12,15,15-trimethyl-6H,12H-28,31-etheno-19,26-methanodibenz[1,t][1,11,4,8,14,23,25]oxathiapentaazacycloheptacosine-7,10,17,34(7H,18H)-tetrone, trifluoroacetate The title compound is prepared from the intermediate obtained in Step D according to the procedure described in Example 9, Step E.

What is claimed is:
1. A compound having the formula:

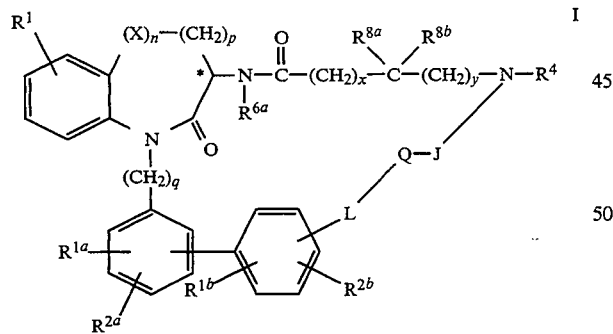

n is 0 or 1;
p is 0 to 3;
q is 0 to 4;
x is 0 to 3;
y is 0 to 3;

X is C=O, O, S(O)$_m$, —CH$\underset{\underset{OH}{|}}{}$—, —N$\underset{\underset{R^{10}}{|}}{}$— or —CH=CH—;

m is 0 to 2;
$R^1$, $R^2$, $R^{1a}$, $R^{2a}$, $R^{1b}$ and $R^{2b}$ are independently hydrogen, halogen, $C_1$–$C_7$ alkyl, $C_1$–$C_3$ perfluoroalkyl, $C_1$–$C_3$ perfluoroalkoxy, —S(O)$_m$R$^{7a}$, cyano, nitro, R$^{7b}$O(CH$_2$)$_v$—, R$^{7b}$COO(CH$_2$)$_v$—, R$^{7b}$OCO(CH$_2$)$_v$—, R$^{4a}$R$^{4b}$N(CH$_2$)$_v$—, R$^{7b}$CON(R$^{4b}$)(CH$_2$)$_v$—, R$^{4a}$R$^{4b}$NCO(CH$_2$)$_v$—, phenyl or substituted phenyl where the phenyl substituents are from 1 to 3 of halogen, $C_1$–$C_6$ alkyl, $C_1$–$C_6$ alkoxy, or hydroxy; and v is 0 to 3;

$R^{7a}$ and $R^{7b}$ are independently hydrogen, $C_1$–$C_3$ perfluoroalkyl, $C_1$–$C_6$ alkyl, substituted $C_1$–$C_6$ alkyl where the substituents are phenyl or substituted phenyl; phenyl or substituted phenyl where the phenyl substituents are from 1 to 3 of halogen, $C_1$–$C_6$ alkyl, $C_1$–$C_6$ alkoxy or hydroxy;

$R^4$, $R^{4a}$ and $R^{4b}$ are independently hydrogen, phenyl, substituted phenyl, $C_1$–$C_{10}$ alkyl, substituted $C_1$–$C_{10}$ alkyl, $C_3$–$C_{10}$ alkenyl, substituted $C_3$–$C_{10}$ alkenyl, $C_3$–$C_{10}$ alkynyl or substituted $C_3$–$C_{10}$ alkynyl where the substituents on the phenyl, alkyl, alkenyl or alkynyl are from 1 to 5 of hydroxy, $C_1$–$C_6$ alkoxy, $C_3$–$C_7$ cycloalkyl, fluoro, $R^1$, $R^2$ independently disubstituted phenyl, $R^1$, $R^2$ independently disubstimted phenyl $C_1$–$C_3$ alkoxy, $C_1$–$C_{20}$ alkanoyloxy, $C_1$–$C_5$ alkoxycarbonyl, carboxy, formyl or —NR$^{10}$R$^{11}$ where $R^1$ and $R^2$ are as defined above and $R^{10}$ and $R^{11}$ are independently hydrogen, $C_1$–$C_6$ alkyl, phenyl, phenyl $C_1$–$C_6$ alkyl, $C_1$–$C_5$ alkoxycarbonyl or $C_1$–$C_5$ alkanoyl-$C_1$–$C_6$ alkyl; or $R^{4a}$ and $R^{4b}$, or $R^{4b}$ and $R^{7b}$ can be taken together to form —(CH$_2$)$_r$—B—(CH$_2$)$_s$— where B is CHR$^1$, O, S(O)$_m$ or NR$^{10}$, m is 0, 1 or 2, r and s are independently 0 to 3 and $R^1$ and $R^{10}$ are as defined;

L is A or $C_1$–$C_6$ alkylene substituted with A;
A is

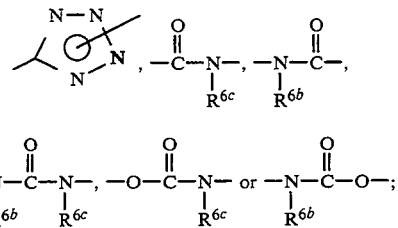

Q is a single bond or

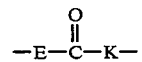

where K is O, S or N—R$^{6d}$;

E and J are independently $C_1$–$C_6$ alkylene or substituted $C_1$–$C_6$ alkylene where the substituents are from 1 to 5 of hydroxy, $C_1$–$C_6$ alkoxy, $C_3$–$C_7$ cycloalkyl, fluoro, $R^1$, $R^2$ independently disubstituted phenyl, $R^1$, $R^2$ independently disubstituted phenyl $C_1$–$C_3$ alkoxy, $C_1$–$C_{20}$ alkanoyloxy, $C_1$–$C_5$ alkoxycarbonyl, carboxy, formyl or —NR$^{10}$R$^{11}$ where $R^1$, $R^2$, $R^{10}$ and $R^{11}$ are as defined;

$R^{6a}$, $R^{6b}$, $R^{6c}$ and $R^{6d}$ are independently hydrogen, $C_1$–$C_{10}$ alkyl, phenyl or phenyl $C_1$–$C_{10}$ alkyl; and $R^{6b}$ and $R^{6c}$ can be taken together to form —(CH$_2$)$_t$— where t is 2 to 6;

$R^{8a}$ and $R^{8b}$ are independently hydrogen, trifluoromethyl, $R^1$, $R^2$ independently disubstituted phenyl, $C_1$–$C_{10}$ alkyl, substituted $C_1$–$C_{10}$ alkyl where the substituents are from 1 to 3 of imidazolyl, indolyl, hydroxy, fluoro, $S(O)_mR^{7a}$, $C_1$-$C_6$ alkoxy, $C_3$-$C_7$ cycloalkyl, $R^1$, $R^2$ independently disubstituted phenyl, $R^1$, $R^2$ independently disubstituted phenyl $C_1$-$C_3$ alkoxy, $C_1$-$C_5$ alkanoyloxy, $C_1$-$C_5$ alkoxycarbonyl, carboxy, formyl or —$NR^{10}R^{11}$ where $R^1$, $R^2$, $R^{7a}$, $R^{10}$, $R^{11}$ and m are as defined above; or $R^{8a}$ and $R^{8b}$ can be taken together to form —$(CH_2)_t$— where t is 2 to 6; and $R^{8a}$ and $R^{8b}$ can independently be joined to $R^4$ to form alkylene bridges wherein the bridge contains from one to five carbon atoms; and pharmaceutically acceptable salts thereof.

2. A compound of claim 1 wherein:

n is 0 or 1;
p is 0 to 3;
q is 0 to 2;
x is 0 to 2;
y is 0 to 2;

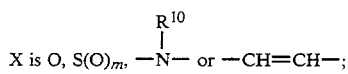

X is O, $S(O)_m$, —$\overset{R^{10}}{\underset{|}{N}}$— or —CH=CH—;

m is 0 to 2;
$R^1$, $R^2$, $R^{1a}$, $R^{2a}$, $R^{1b}$ and $R^{2b}$ are independently hydrogen, halogen, $C_1$-$C_7$ alkyl, $C_1$-$C_3$ perfluoroalkyl, —$S(O)_mR^{7a}$, $R^{7b}O(CH_2)_v$—, $R^{7b}COO(CH_2)_v$—, $R^{7b}OCO(CH_2)_v$—, phenyl or substituted phenyl where the phenyl substituents are from 1 to 3 of halogen, $C_1$-$C_6$ alkyl, $C_1$-$C_6$ alkoxy, or hydroxy; and v is 0 to 2;
$R^{7a}$ and $R^{7b}$ are independently hydrogen, $C_1$-$C_3$ perfluoroalkyl, $C_1$-$C_6$ alkyl, substituted $C_1$-$C_6$ alkyl where the substituents are phenyl; phenyl; $R^4$, $R^{4a}$, and $R^{4b}$ are independently hydrogen, phenyl, substituted phenyl, $C_1$-$C_{10}$ alkyl or substituted $C_1$-$C_{10}$ alkyl where the substituents on the phenyl or alkyl are from 1 to 5 of hydroxy, $C_1$-$C_6$ alkoxy, $C_3$-$C_7$ cycloalkyl, fluoro, $R^1$, $R^2$ independently disubstimted phenyl, $R^1$, $R^2$ independently disubstituted phenyl $C_1$-$C_3$ alkoxy, $C_1$-$C_{20}$ alkanoyloxy, $C_1$-$C_5$ alkoxycarbonyl, carboxy or formyl where $R^1$ and $R^2$ are as defined above;
L is A or $C_1$-$C_6$ alkylene substituted with A;
A is

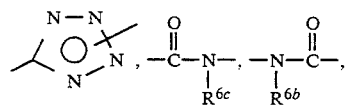

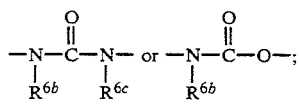

Q is a single bond or

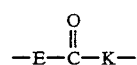

where K is O or N—$R^{6d}$;
E and J are independently $C_1$-$C_6$ alkylene or substituted $C_1$-$C_6$ alkylene where the substituents are from 1 to 3 of hydroxy, $C_1$-$C_3$ alkoxy, fluoro, $R^1$, $R^2$ independently disubstituted phenyl, $C_1$-$C_{10}$ alkanoyloxy, $C_1$-$C_5$ alkoxycarbonyl, carboxy or formyl where $R^1$ and $R^2$ are as defined;
$R^{6a}$, $R^{6b}$, $R^{6c}$ and $R^{6d}$ are independently hydrogen, $C_1$-$C_{10}$ alkyl or phenyl $C_1$-$C_{10}$ alkyl; and $R^{6b}$ and $R^{6c}$ can be taken together to form —$(CH_2)_t$— where t is 2 to 4;
$R^{8a}$ and $R^{8b}$ are independently hydrogen, $C_1$-$C_{10}$ alkyl, substituted $C_1$-$C_{10}$ alkyl where the substituents are from 1 to 3 of imidazolyl, indolyl, hydroxy, fluoro, —$S(O)_mR^{7a}$, $C_1$-$C_6$ alkoxy, $C_3$-$C_7$ cycloalkyl, $R^1$, $R^2$ independently disubstituted phenyl, $R^1$, $R^2$ independently disubstituted phenyl $C_1$-$C_3$ alkoxy, $C_1$-$C_5$ alkanoyloxy, $C_1$-$C_5$ alkoxycarbonyl, carboxy, formyl, —$NR^{10}R^{11}$ where $R^1$, $R^2$, $R^{7a}$, $R^{10}$, $R^{11}$ and m are as defined above; or $R^{8a}$ and $R^{8b}$ can be taken together to form —$(CH_2)_t$— where t is 2 to 4; and $R^{8a}$ and $R^{8b}$ can independently be joined to $R^4$ to form alkylene bridges wherein the bridge contains from one to five carbon atoms; and pharmaceutically acceptable salts thereof.

3. A compound of claim 2 wherein:

n is 0 or 1;
p is 0 to 2;
q is 0 to 2;
x is 0 to 2;
y is 0 to 2;
X is $S(O)_m$ or —CH=CH—; m is 0 or 1;
$R^1$, $R^2$, $R^{1a}$, $R^{2a}$, $R^{1b}$ and $R^{2b}$ are independently hydrogen, halogen, $C_1$-$C_7$ alkyl, $C_1$-$C_3$ perfluoroalkyl, —$S(O)_mR^{7a}$, $R^{7b}O(CH_2)_v$—, $R^{7b}COO(CH_2)_v$—, $R^{7b}OCO(CH_2)_v$—, phenyl or substituted phenyl where the phenyl substituents are from 1 to 3 of halogen, $C_1$-$C_6$ alkyl, $C_1$-$C_6$ alkoxy, or hydroxy; and v is 0 to 2;
$R^{7a}$ and $R^{7b}$ are independently hydrogen, $C_1$-$C_6$ alkyl or substituted $C_1$-$C_6$ alkyl where the substituents are phenyl;
$R^4$, $R^{4a}$ and $R^{4b}$ are independently hydrogen, $C_1$-$C_{10}$ alkyl or substituted $C_1$-$C_{10}$ alkyl where the substituents are from 1 to 5 of hydroxy, $C_1$-$C_6$ alkoxy, fluoro, $R^1$, $R^2$ independently disubstituted phenyl, $C_1$-$C_{20}$ alkanoyloxy, $C_1$-$C_5$ alkoxycarbonyl or carboxy where $R^1$ and $R^2$ are as defined above;
L is A or $C_1$-$C_6$ alkylene substituted with A;
A is

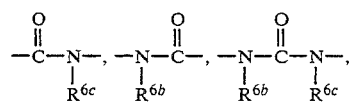

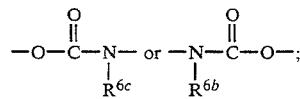

Q is a single bond or

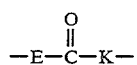

where K is O or N—$R^{6d}$;
E and J are independently $C_1$-$C_6$ alkylene or substituted $C_1$-$C_6$ alkylene where the substituents are from 1 to 3 of hydroxy, fluoro, $R^1$, $R^2$ independently disubstituted phenyl, $C_1$-$C_5$ alkanoyloxy, $C_1$-$C_5$ alkoxycarbonyl or carboxy where $R^1$ and $R^2$ are as defined;

$R^{6a}$, $R^{6b}$, $R^{6c}$ and $R^{6d}$ are independently hydrogen or $C_1$-$C_{10}$ alkyl;

$R^{8a}$ and $R^{8b}$ are independently hydrogen, $C_1$-$C_{10}$ alkyl, substituted $C_1$-$C_{10}$ alkyl where the substituents are from 1 to 3 of imidazolyl, indolyl, hydroxy, fluoro, —S(O)$_m$R$^{7a}$, $C_1$-$C_6$ alkoxy, $C_3$-$C_7$ cycloalkyl, $R^1$, $R^2$ independently disubstituted phenyl, $R^1$, $R^2$ independently disubstituted phenyl $C_1$-$C_3$ alkoxy, $C_1$-$C_5$ alkanoyloxy, $C_1$-$C_5$ alkoxycarbonyl, carboxy, formyl or —NR$^{10}$R$^{11}$ where $R^1$, $R^2$, $R^{7a}$, $R^{10}$, $R^{11}$ and m are as defined above; or $R^{8a}$ and $R^{8b}$ can be taken together to form —(CH$_2$)$_t$— where t is 2; and $R^{8a}$ and $R^{8b}$ can independently be joined to $R^4$ to form alkylene bridges wherein the bridge contains from one to five carbon atoms; and pharmaceutically acceptable salts thereof.

4. A compound of claim 3 wherein:
n is 0 or 1;
p is 0 to 2;
q is 1;
x is 0 or 1;
y is 0 or 1;
X is S(O)m or —CH=CH—; m is 0 or 1;
$R^1$, $R^2$, $R^{1a}$, $R^{2a}$, $R^{1b}$ and $R^{2b}$ are independently hydrogen, halogen, $C_1$-$C_7$ alkyl, $C_1$-$C_3$ perfluoroalkyl, —S(O)$_m$R$^{7a}$, $R^{7b}$O(CH$_2$)$_v$—, $R^{7b}$COO(CH$_2$)$_v$—, phenyl or , substituted phenyl where the substituents are from 1 to 3 of halogen, $C_1$-$C_6$ alkyl, $C_1$-$C_6$ alkoxy or hydroxy and v is 0 or 1;

$R^{7a}$ and $R^{7b}$ are independently hydrogen, $C_1$-$C_6$ alkyl or substituted $C_1$-$C_6$ alkyl where the substituents are phenyl;

$R^4$, $R^{4a}$ and $R^{4b}$ are independently hydrogen, $C_1$-$C_{10}$ alkyl or substituted $C_1$-$C_{10}$ alkyl where the substituents are from 1 to 3 of hydroxy, $C_1$-$C_3$ alkoxy, fluoro, $R^1$, $R^2$ independently disubstimted phenyl, $C_1$-$C_{10}$ alkanoyloxy, $C_1$-$C_5$ alkoxycarbonyl or carboxy where $R^1$ and $R^2$ are as defined above;

L is A or $C_1$-$C_4$ alkylene substituted with A;

A is

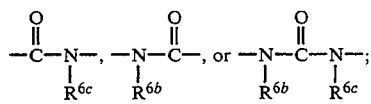

Q is

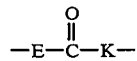

where K is O;

E and J are independently $C_1$-$C_4$ alkylene or substituted $C_1$-$C_4$ alkylene where the substituents are from 1 to 3 of hydroxy, fluoro, $R^1$, $R^2$ independently disubstituted phenyl, $C_1$-$C_5$ alkanoyloxy, $C_1$-$C_5$ alkoxycarbonyl or carboxy where $R^1$ and $R^2$ are as defined;

$R^{6a}$, $R^{6b}$, $R^{6c}$ and $R^{6d}$ are hydrogen;

$R^{8a}$ and $R^{8b}$ are independently hydrogen, $C_1$-$C_{10}$ alkyl, substituted $C_1$-$C_{10}$ alkyl where the substituents are from 1 to 3 of imidazolyl, indolyl, hydroxy, fluoro, —S(O)$_m$R$^{7a}$, $C_1$-$C_6$ alkoxy, $C_3$-$C_7$ cycloalkyl, $R^1$, $R^2$ independently disubstituted phenyl, $C_1$-$C_5$ alkanoyloxy, $C_1$-$C_5$ alkoxycarbonyl or carboxy, where $R^1$, $R^2$, $R^{7a}$, and m are as defined; or $R^{8a}$ and $R^{8b}$ can be taken together to form —(CH$_2$)$_t$— where t is 2; and $R^{8a}$ and $R^{8b}$ can independently be joined to $R^4$ to form alkylene bridges wherein the bridge contains from one to five carbon atoms; and pharmaceutically acceptable salts thereof.

5. A stereospecific compound of claim 1 having the following structural formula:

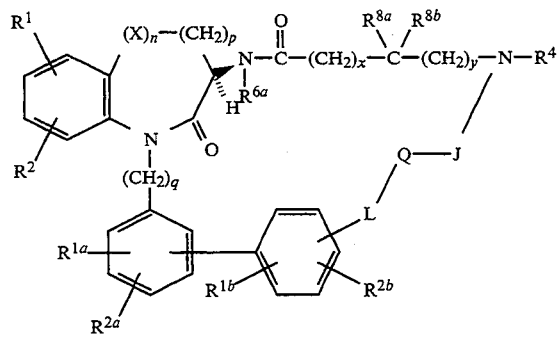

where $R^1$, $R^2$, $R^{1a}$, $R^{2a}$, $R^{1b}$, $R^{2b}$, $R^4$, $R^{6a}$, $R^{8a}$, $R^{8b}$, J, L, Q, X, n, p, q, x and y are as defined in claim 1.

6. A compound of claim 1 which is:
(R)-8,9,10,11,13,14,15,16-Octahydro-10,10-dimethyl-6H-23,26-etheno-14,21-methanodibenzo[1,t][1,4,8,14]tetraazacyclodocosine-5,12,29(7H,22H)-trione;

(R)-8,9,10,11,13,14,15,16-Octahydro-10,10-dimethyl-18-fluoro-6H-23,26-etheno-14,21-methanodibenzo[1,t][1,4,8,14]tetraazacyclodocosine-5,12,29(7H,22H)-trione;

(R)-8,9,10,11,13,14,15,16-Octahydro-10,10-dimethyl-18-trifluoromethyl-H-23,26-etheno-14,21-methanodibenzo[1,t][1,4,8,14]tetraazacyclodocosine-5,12,29(7H,22H)-trione;

(R)-8,9,10,11,13,14,15,16-Octahydro-10,10-dimethyl-18-methoxy-6H-23,26-etheno-14,21-methanodibenzo[1,t][1,4,8,14]tetraazacyclodocosine-5,12,29(7H,22H)-trione;

(R)-8,9,10,11,13,14,15,16-Octahydro-10,10-dimethyl-18-methylthio-6H-23,26-etheno-14,21-methanodibenzo[1,t][1,4,8,14]tetraazacyclodocosine-5,12,29(7H,22H)-trione;

(10R,17R)-11,12,13,14,16,17,18,19-Octahydro-10,13,13-trimethyl-6H-26,29-etheno-17,24-methanodibenz[1,t][1,4,8,14,23]-oxatetraazacyclopentacosine-5,8,15,32(7H,10H,25H)-tetrone;

(10R,17R)-11,12,13,14,16,17,18,19-Octahydro-10,13,13-trimethyl-21-methylthio-6H-26,29-etheno-17,24-methanodibenz[1,t][1 „4,8,14,23]oxatetraazacyclopentacosine-5,8,15,32(7H,10H,25H)-tetrone;

(10R,17R)-11,12,13,14,16,17,18,19-Octahydro-10,13,13-trimethyl-21-methoxy-6H-26,29-etheno-17,24-methanodibenz[1,t][1,4,8,14,23]oxatetraazacyclopentacosine-5,8,15,32(7H,10H,25H)-tetrone;

(10R,17R)-11,12,13,14,16,17,18,19-Octahydro-10,13,13-trimethyl-21-fluoro-6H-26,29-etheno-17,24-methanodibenz[1,t][1,4,8,14,23]oxatetraazacyclopentacosine-5,8,15,3 2(7H,10H,25H)-tetrone;

(10R,17R)-11,12,13,14,16,17,18,19-Octahydro-10,13,13-trimethyl-21-trifluoromethyl-6H-26,29-etheno-17,24-methanodibenz[1,t][1,4,8,14,23]oxatetraazacyclopentacosine-5,8,15,32(7H,10H,25H)-tetrone;

(10R,17R)-11,12,13,14,16,17;18,19-Octahydro-13,13-dimethyl-6H-26,29-etheno-17,24-methanodibenz[1,t][1,4,8,14,23]oxatetraazacyclopentacosine-5,8,15,32(7H,10H,25H)-tetrone;

(10R,17R)-11,12,13,14,16,17,18,19-Octahydro-13,13-dimethyl-21-methylthio-6H-26,29-etheno-17,24-methanodibenz[1t][1,4,8,14,23]oxatetraazacyclopentacosine-5,8,15,32(7H,10H,25H)-tetrone;

(10R,17R)-11,12,13,14,16,17,18,19-Octahydro-13,13-dimethyl-21-methoxy-6H-26,29-etheno-17,24-methanodibenz[1,t][1,4,8,14,23]oxatetraazacyclopentacosine-5,8,15,32(7H,10H,25H,)-tetrone;

(10R, 17R )-11,12,13,14,16,17,18,19-Octahydro-13,13-dimethyl-21-fluoro-6H-26,29-etheno-17,24-methanodibenz[1,t[1,4,8,14,23]-oxatetraazacyclopentacosine-5,8,15,32(7H,10H,25H)-tetrone;

(10R,17R)-11,12,13,14,16,17,18,19-Octahydro-13,13-dimethyl-21-trifluoromethyl-6H-26,29-etheno-17,24-methanodibenz[1,t][1,4,8,14,23]oxatetraazacyclopentacosine-5,8,15,32(7H,10H,25H)-tetrone;

(11R,18R)-7,8,12,13,14,15,17,18,19,20-Decahydro-11,14,14-trimethyl-27,30-etheno-18,25-methano-25H-dibenz[1,t][1,4,8,14,23]oxatetraazacyclohexacosine-5,9,16,33(6H,11H,26H)-tetrone;

(11R,18R)-7,8,12,13,14,15,17,18,19,20-Decahydro-22-methoxy-11,14,14-trimethyl-27,30-etheno-18,25-methano-25H-dibenz[1,t][1,4,8,14,23]oxatetraazacyclohexacosine-5,9,16,33(6H,11H,26H)-tetrone;

(11R,18R)-7,8,12,13,14,15,17,18,19,20-Decahydro-22-methylthio-11,14,14-trimethyl-27,30-etheno-18,25-methano-25H-dibenz[1,t][1,4,8,14,23]oxatetraazacyclohexacosine-5,9,16,33(6H,11H,26H)-tetrone;

(11R,18R)-7,8,12,13,14,15,17,18,19,20-Decahydro-22-fluoro-11,14,14-trimethyl-27,30-etheno-18,25-methano-25H-dibenz[1,t][1,4,8,14,23]-oxatetraazacyclohexacosine-5,9,16,33(6H,11H,26H)-tetrone;

(11R,18R)-7,8,12,13,14,15,17,18,19,20-Decahydro-22-trifluoromethyl-11,14,14-trimethyl-27,30-etheno-18,25-methano-25H-dibenz[1,t][1,4,8,14,2-3]oxatetraazacyclohexacosine-5,9,16,33(6H,11H,26H)-tetrone;

(11R,18R)-7,8,12,13,14,15,17,18,19,20-Decahydro-14,14-dimethyl-27,30-etheno-18,25-methano-25H-dibenz[1,t][1,4,8,14,23]oxatetraazacyclohexacosine-5,9,16,33(6H,11H,26H)-tetrone;

(11R,18R)-7,8,12,13,14,15,17,18,19,20-Decahydro-22-methoxy-14,14-dimethyl-27,30-etheno-18,25-methano-25H-dibenz[1,t][1,4,8,14,23]oxatetraazacyclohexacosine-5,9,16,33(6H,11H,26H)-tetrone;

(11R,18R)-7,8,12,13,14,15,17,18,19,20-Decahydro-22-methylthio-14,14-dimethyl-27,30-etheno-18,25-methano-25H-dibenz[1,t][1,4,8,14,23]oxatetraazacyclohexacosine-5,9,16,33(6H,11H,26H)-tetrone;

(11R,18R)-7,8,12,13,14,15,17,18,19,20-Decahydro-22-fluoro-14,14-dimethyl-27,30-etheno-18,25-methano-25H-dibenz[1,t][1,4,8,14,23]-oxatetraazacyclohexacosine-5,9,16,33(6H,11H,26H)-tetrone;

(11R,18R)-7,8,12,13,14,15,17,18,19,20-Decahydro-22-trifluoromethyl-14,14-dimethyl-27,30-etheno-18,25-methano-25H-dibenz[1,t][1,4,8,14,23]oxatetraazacyclohexacosine-5,9,16,33(6H,11H,26H)-tetrone;

(12R,19R)-8,9,13,14,15,16,18,19,20,21-Decahydro-12,15,15-trimethyl, 6H-28,31-etheno-19,26-methanodibenz[1,t][1,4,8,14,23]-oxatetraazacycloheptacosine-5,10,17,34(7H,12H,27H)-tetrone;

(12R,19R)-8,9,13,14,15,16,18,19,20,21-Decahydro-23-fluoro-12,15,15-trimethyl-6H-28,31-etheno-19,26-methanodibenz[1,t][1,4,8,14,23]-oxatetraazacycloheptacosine-5,10,17,34(7 H,12H,27H)-tetrone;

(12R,19R)-8,9,13,14,15,16,18,19,20,21-Decahydro-23-trifluoromethyl-12,15,15-trimethyl-6H-28,31-etheno-19,26-methanodibenz[1,t][1,4,8,14,23]oxatetraazacycloheptacosine-5,10,17,34(7H,12H,27H)-tetrone;

(12R,19R)-8,9,13,14,15,16,18,19,20,21-Decahydro-23-methoxy-12,15,15-trimethyl-6H-28,31-etheno-19,26-methanodibenz[1,t][1,4,8,14,23]oxatetraazacycloheptacosine-5,10,17,34(7H,12H,27H)-tetrone;

(12R,19R)-8,9,13,14,15,16,18,19,20,21-Decahydro-23-methylthio-12,15,15-trimethyl-6H-28,31-etheno-19,26-methanodibenz[1,t[1,4,8,14,23]oxatetraazacycloheptacosine-5,10,17,34(7H,12H,27H)-tetrone;

(12R,19R)-8,9,13,14,15,16,18,19,20,21-Decahydro-15,15-dimethyl-6H-28,31-etheno-19,26-methanodibenz[1,t][1,4,8,14,23]oxatetraazacycloheptacosine-5,10,17,34(7H,12H,27H)-tetrone;

(12R, 19R )-8,9,13,14,15,16,18, 19,20,21-Decahydro-23-fluoro-15,15-dimethyl-6H-28,31-etheno-19,26-methanodibenz[1,t][1,4,8,14,23]oxatetraazacycloheptacosine-5,10,17,34(7H,12H,27H)-tetrone;

(12R,19R)-8,9,13,14,15,16,18,19,20,21-Decahydro-23-trifluoromethyl-15,15-dimethyl-6H-28,31-etheno-19,26-methanodibenz[1,t][1,4,8,14,23]oxatetraazacycloheptacosine-5,10,17,34(7H,12H,27H)-tetrone;

(12R, 19R )-8,9,13,14,15,16,18,19,20,21-Decahydro-23-methoxy-15,15-dimethyl-6H-28,31-etheno-19,26-methanodibenz[1,t][1,4,8,14,23]oxatetraazacycloheptacosine-5,10,17,34(7H,12H,27H)-tetrone;

(12R, 19R )-8,9,13,14,15,16,18,19,20,21-Decahydro-23-methylthio-15,15-dimethyl-6H-28,31-etheno-19,26-methanodibenz[1,t][1,4,8,14,23]oxatetraazacycloheptacosine-5,10,17,34(7H,12H,27H)-tetrone;

(R)-11,12,13,14,15,16,18,19,20,21-Decahydro-15,15-dimethyl-9H,27H-28,3.1-etheno-19,26-methano-8,5-nitrilo-5H-dibenzo[1,t][1,2,3,6,9,13,19]heptaazacycloheptacosine-10,17,34-trione;

(R)-11,12,13,14,15,16,18,19,20,21-Decahydro-15,15-dimethyl-23-fluoro9H,27H-28,31-etheno-19,26-methano-8,5-nitrilo-5H-dibenzo[q,y][1,2,3,6,9,13,19]heptaazacycloheptacosine-10,17,34-trione;

(R)-11,12,13,14,15,16,18,19,20,21-Decahydro-15,15-dimethyl-23-trifluoromethyl-9H,27H-28,31-etheno-19,26-methano-8,5-nitrilo-5H-dibenzo[q,y][1,2,3,6,9,13,19]heptaazacycloheptacosine-10,17,34-trione;

(R)-11,12,13,14,15,16,18, 19,20,21-Decahydro-15,15-dimethyl-23-methoxy-9H,27H-28,31-etheno-19,26-methano-8,5-nitrilo-5H-dibenzo[q-

,y][1,2,3,6,9,13,19]heptaazacycloheptacosine-10,17,34-trione;

(R)-11,12,13,14,15,16,18,19,20,21-Decahydro-15,15-dimethyl-23-methylthio-9H,27H-28,31-etheno-19,26-methano-8,5-nitrilo-5H-dibenzo[q,y][1,2,3,6,9,13,19]heptaazacycloheptacosine-10,17,34-trione;

(12R,19R)-5,8,9,13,14,15,16,18,19,20,21,27-Dodecahydro-12,15,15-trimethyl-6H-28,31-etheno-19,26-methanodibenz[1,t][1,4,8,14,23,25]-oxapentaazacycloheptacosine-7,10,17,34(7H,12H)-tetrone;

(12R,19R)-5,8,9,13,14,15,16,18,19,20,21,27-Dodecahydro-23-methylthio-12,15,15-trimethyl-6H-28,31-etheno-19,26-methanodibenz[1,t][1,4,8,14,23,25]oxapentaazacycloheptacosine-7,10,17,34(7H,12H)-tetrone;

(12R,19R)-5,8,9,13,14,15,16,18,19,20,21,27-Dodecahydro-23-methoxy-12,15,15-trimethyl-6H-28,31-etheno-19,26-methanodibenz[1,t][1,4,8,14,23,25]oxapentaazacycloheptacosine-7,10,17,34(7H,12H)-tetrone;

(12R, 19R)-5,8,9,13,14,15,16,18,19,20,21,27-Dodecahydro-23-trifluoromethyl-12,15,15-trimethyl-6H-28,31-etheno-19,26-methanodibenz[1,t][1,4,8,14,23,25]oxapentaazacycloheptacosine-7,10,17,34(7H,12H)-tetrone;

(12R,19R)-5,8,9,13,14,15,16,18,19,20,21,27-Dodecahydro-15,15-dimethyl-6H-28,31-etheno-19,26-methanodibenz[1,t][1,4,8,14,23,25]oxapentaazacycloheptacosine-7,10,17,34(7H,12H)-tetrone;

(12R,19R)-5,8,9,13,14,15,16,18,19,20,21,27-Dodecahydro-23-methylthio-15,15-dimethyl-6H-28,31-etheno-19,26-methanodibenz[1,t][1,4,8,14,23,25]oxapentaazacycloheptacosine-7,10,17,34(7H,12H)-tetrone;

(12R,19R)-5,8,9,13,14,15,16,18,19,20,21,27-Dodecahydro-23-methoxy-15,15-dimethyl-6H-28,31-etheno-19,26-methanodibenz[1,t][1,4,8,14,23,25]oxapentaazacycloheptacosine-7,10,17,34(7 H,12H)-tetrone;

(12R,19R)-5,8,9,13,14,15,16,18,19,20,21,27-Dodecahydro-23-fluoro15,15-dimethyl-6H-28,31-etheno-19,26-methanodibenz[1,t][1,4,8,14,23,25]oxapentaazacycloheptacosine-7,10,17,34(7H,12H)-tetrone;

(13R,20R)-5,9,10,14,15,16,17,19,20,21,22,28-Dodecahydro-13,16,16-trimethyl-29,32-etheno-20,27-methano-27H-dibenz[1,t][1,4,8,14,23,25]oxapentaazacyclooctacosine-7,11,18,35(6H,8H,13H)-tetrone;

(13R,20R )-5,9,10,14,15,16,17,19,20,21,22,28-Dodecahydro-24-fluoro13,16,16-trimethyl-29,32-etheno-20,27-methano-27H-dibenz[1,t][1,4,8,14,23,25]oxapentaazacyclooctacosine-7,11,18,35(6H,8H,13H)-tetrone;

(13R,20R)-5,9,10,14,15,16,17,19,20,21,22,28-Dodecahydro-24-trifluoromethyl-13,1 6,16-trimethyl-29,32-etheno-20,27-methano-27H-dibenz[1,t][1,4,8,14,23,25]oxapentaazacyclooctacosine-7,11,18,35(6H,8H,13H)-tetrone;

(13R,20R)-5,9,10,14,15,16,17,19,20,21,22,28-Dodecahydro-24-methoxy-13,16,16-trimethyl-29,32-etheno-20,27-methano-27H-dibenz[1,t][1,4,8,14,23,25]oxapentaazacyclooctacosine-7,11,18,35(6H,8H,13H)-tetrone;

(13R,20R)-5,9,10,14,15,16,17,19,20,21,22,28-Dodecahydro-24-methylthio-13,16,16-trimethyl-29,32-etheno-20,27-methano-27H-dibenz[1,t][1,4,8,14,23,25]oxapentaazacyclooctacosine-7,11,18,35(6H,8H,13H)-tetrone;

(13R,20R)-5,9,10,14,15,16,17,19,20,21,22,28-Dodecahydro-16,16-dimethyl-29,32-etheno-20,27-methano-27H-dibenz[1,t][1,4,8,14,23,25]oxapentaazacyclooctacosine-7,11,18,35(6H,8H,13H)-tetrone;

(13R,20R)-5,9,10,14,15,16,17,19,20,21,22,28-Dodecahydro-24-fluoro16,16-dimethyl-29,32-etheno-20,27-methano-27H-dibenz[1,t][1,4,8,14,23,25]oxapentaazacyclooctacosine-7,11,18,35(6H,8H,13H)-tetrone;

(13R,20R)-5,9,10,14,15,16,17,19,20,21,22,28-Dodecahydro-24-trifluoromethyl-16,16-dimethyl-29,32-etheno-20,27-methano-27H-dibenz[1,t][1,4,8,14,23,25]oxapentaazacyclooctacosine-7,11,18,35(6H,8H,13H)-tetrone;

(13R,20R )-5,9,10,14,15,16,17,19,20,21,22,28-Dodecahydro-24-methoxy-16,16-dimethyl-29,32-etheno-20,27-methano-27H-dibenz[1,t][1,4,8,14,23,25]oxapentaazacyclooctacosine-7,11,18,35(6H,8H,13H)-tetrone;

(13R,20R )-5,9,10,14,15,16 ,,17,19,20,21,22,28-Dodecahydro-24-methylthio-16,16-dimethyl-29,32-etheno-20,27-methano-27H-dibenz[1,t][1,4,8,14,23,25]oxapentaazacyclooctacosine-7,11,18,35(6H,8H,13H)-tetrone;

(12R, 19R )-8,9,13,14,15,16,19,20-Octahydro-12,15,15-trimethyl-6H,12H-28,31-etheno-19,26-methanodibenz[1,t][1,11,4,8,14,23]oxathiatetraazacycloheptacosine-5,10,17,34(7H,18H,27H)-tetrone;

(12R,19R)-8,9,13,14,15,16,19,20-Octahydro-23-methoxy-12,15,15-trimethyl-6H,12H-28,31-etheno-19,26-methanodibenz[1,t][1,11,4,8,14,23]oxathiatetraazacycloheptacosine-5,10,17,34(7H,18H,27H)-tetrone;

(12R, 19R)-8,9,13,14,15,16,19,20-Octahydro-23-trifluoromethyl-12,15,15-trimethyl-6H,12H-28,31-etheno-19,26-methanodibenz[1,t][1,11,4,8,14,23]oxathiatetraazacycloheptacosine-5,10,17,34(7H,18H,27H)-tetrone;

(12R,19R)-8,9,13,14,15,16,19,20-Octahydro-23-methylthio-12,15,15-trimethyl-6H,12H-28,31-etheno-19,26-methanodibenz[1,t][1,11,4,8,14,23]oxathiatetraazacycloheptacosine-5,10,17,34(7H,18H,27H)-tetrone;

(12R,19R)-8,9,13,14,15,16,19,20-Octahydro-15,15-dimethyl-6H,12H-28,31-etheno-19,26-methanodibenz[1,t][1,11,4,8,14,23]oxathiatetraazacycloheptacosine-5,10,17,34(7H,18H,27H)-tetrone;

(12R,19R)-8,9,13,14,15,16,19,20-Octahydro-23-fluoro-15,15-dimethyl-6H,12H-28,31-etheno-19,26-methanodibenz[1,t][1,11,4,8,14,23]oxathiatetraazacycloheptacosine-5,10,17,34(7H,18H,27H)-tetrone;

(12R,19R)-8,9,13,14,15,1. 6,19,20-Octahydro-23-methoxy-15,15-dimethyl-6H,12H-28,31-etheno-19,26-methanodibenz[1,t][1,11,4,8,14,23]oxathiatetraazacycloheptacosine-5,10,17,34(7H,18H,27H)-tetrone;

(12R, 19R)-8,9,13,14,15,16,19,20-Octahydro-23-methylthio-15,15-dimethyl-6H,1,2H-28,31-etheno-19,26-methanodibenz[1,t ][1,11,4,8,14,23]oxathiatetraazacycloheptacosine-5,10,17,34(7H,18H,27H)-tetrone;

(12R,19R)-5,8,9,13,14,15,16,19,20,27-Decahydro-12,15,15-trimethyl-6H,12H-28,31-etheno-19,26-methanodibenz[1,t][1,11,4,8,14,23,25]oxathiapentaazacycloheptacosine-7,10,17,34(7H,18H)-tetrone;

(12R,19R)-5,8,9,13,14,15,16,19,20,27-Decahydro-23-trifluoromethyl-12,15,15-trimethyl-6H,12H-28,31-etheno-19,26-methanodibenz[1,t][1,11,4,8,14,23,25]oxathiapentaazacycloheptacosine-7,10,17,34(7H,18H)-tetrone;

(12R,19R)-5,8,9,13,14,15,16,19,20,27-Decahydro-23-methoxy-12,15,15-trimethyl-6H,12H-28,31-etheno-19,26-methanodibenz[1,t][1,11,4,8,14,23,25]oxathiapentaazacycloheptacosine-7,10,17,34(7H,18H)-tetrone;

(12R,19R)-5,8,9,13,14,15,16,19,20,27-Decahydro-23-methylthio-12,15,15-trimethyl-6H,12H-28,31-etheno-19,26-methanodibenz[1,t][1,11,4,8,14,23,25]oxathiapentaazacycloheptacosine-7,10,17,34(7H,18H)-tetrone;

(12R,19R)-5,8,9,13,14,15,16,19,20,27-Decahydro-15,15-dimethyl-6H,12H-28,31-etheno-19,26-methanodibenz[1,t][1,11,4,8,14,23,25]oxathiapentaazacycloheptacosine-7,10,17,34(7H,18H)-tetrone;

(12R,19R)-5,8,9,13,14,15,16,19,20,27-Decahydro-23-fluoro-15,15-dimethyl-6H,12H-28,31-etheno-19,26-methanodibenz[1,t][1,11,4,8,14,23,25]oxathiapentaazacycloheptacosine-7,10,17,34(7H,18H)-tetrone;

(12R,19R)-5,8,9,13,14,15,16,19,20,27-Decahydro-23-methoxy-15,15-dimethyl-6H,12H-28,31-etheno-19,26-methanodibenz[1,t][1,11,4,8,14,23,25]oxathiapentaazacycloheptacosine-7,10,17,34(7H,18H)-tetrone; or (12R,19R)-5,8,9,13,14,15,16,19,20,27-Decahydro-23-methylthio-15,15-dimethyl-6H,12H-28,31-etheno-19,26-methanodibenz[1,t][1,11,4,8,14,23,25]-oxathiapentaazacycloheptacosine-7,10,17,34(7H,18H)-tetrone.

* * * * *